(12) United States Patent
Grandea, III et al.

(10) Patent No.: US 8,114,402 B2
(45) Date of Patent: *Feb. 14, 2012

(54) COMPOSITIONS AND METHODS FOR THE THERAPY AND DIAGNOSIS OF INFLUENZA

(75) Inventors: Andres Grandea, III, Shoreline, WA (US); Gordon King, Shoreline, WA (US); Thomas Cox, Redmond, WA (US); Ole Olsen, Everett, WA (US); Jennifer Mitcham, Redmond, WA (US); Matthew Moyle, Redmond, WA (US)

(73) Assignee: Theraclone Sciences, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/726,297

(22) Filed: Mar. 17, 2010

(65) Prior Publication Data

US 2010/0178295 A1 Jul. 15, 2010

Related U.S. Application Data

(62) Division of application No. 12/269,781, filed on Nov. 12, 2008.

(51) Int. Cl.
*A61K 39/42* (2006.01)
*C07K 16/08* (2006.01)
*C12Q 1/70* (2006.01)

(52) U.S. Cl. ............. 424/147.1; 424/204.1; 530/388.15; 530/388.3; 435/5

(58) Field of Classification Search .................. None
See application file for complete search history.

(56) References Cited

U.S. PATENT DOCUMENTS

| | | | |
|---|---|---|---|
| 3,773,919 A | 11/1973 | Boswell et al. |
| 3,896,111 A | 7/1975 | Kupchan et al. |
| 4,137,230 A | 1/1979 | Hashimoto et al. |
| 4,151,042 A | 4/1979 | Higashide et al. |
| 4,248,870 A | 2/1981 | Miyashita et al. |
| 4,256,746 A | 3/1981 | Miyashita et al. |
| 4,260,608 A | 4/1981 | Miyashita et al. |
| 4,265,814 A | 5/1981 | Hashimoto et al. |
| 4,294,757 A | 10/1981 | Asai |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,946 A | 2/1982 | Powell et al. |
| 4,315,929 A | 2/1982 | Freedman et al. |
| 4,317,821 A | 3/1982 | Miyashita et al. |
| 4,322,348 A | 3/1982 | Asai et al. |
| 4,331,598 A | 5/1982 | Hasegawa et al. |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,424,219 A | 1/1984 | Hashimoto et al. |
| 4,450,254 A | 5/1984 | Isley et al. |
| 4,485,045 A | 11/1984 | Regen |
| 4,544,545 A | 10/1985 | Ryan et al. |
| 4,554,101 A | 11/1985 | Hopp |
| 4,676,980 A | 6/1987 | Segal et al. |
| 4,683,202 A | 7/1987 | Mullis |
| 4,816,567 A | 3/1989 | Cabilly et al. |
| 4,975,278 A | 12/1990 | Senter et al. |
| 5,013,556 A | 5/1991 | Woodle et al. |
| 5,053,394 A | 10/1991 | Ellestad et al. |
| 5,208,020 A | 5/1993 | Chari et al. |
| 5,229,275 A | 7/1993 | Goroff |
| 5,416,064 A | 5/1995 | Chari et al. |
| 5,500,362 A | 3/1996 | Robinson et al. |
| 5,545,806 A | 8/1996 | Lonberg et al. |
| 5,545,807 A | 8/1996 | Surani et al. |
| 5,567,610 A | 10/1996 | Borrebaeck et al. |
| 5,569,825 A | 10/1996 | Lonberg et al. |
| 5,571,894 A | 11/1996 | Wels et al. |
| 5,587,458 A | 12/1996 | King et al. |
| 5,591,669 A | 1/1997 | Krimpenfort et al. |
| 5,627,052 A | 5/1997 | Schrader |
| 5,641,870 A | 6/1997 | Rinderknecht et al. |
| 5,648,237 A | 7/1997 | Carter |
| 5,712,374 A | 1/1998 | Kuntsmann et al. |
| 5,714,586 A | 2/1998 | Kunstmann et al. |
| 5,739,116 A | 4/1998 | Hamann et al. |
| 5,739,277 A | 4/1998 | Presta et al. |

(Continued)

FOREIGN PATENT DOCUMENTS

EP 73657 A1 3/1983

(Continued)

OTHER PUBLICATIONS

Madec et al., Four IgG Anti-Islet Human Monoclonal Antibodies Isolated from a Type 1 Diabetes Patient Recognize Distinct Epitopes of Glutamic Acid Decarboxylase 65 and are Somatically Mutated, 1996, Journal of Immunology, vol. 156, pp. 3541-3549.*

Vajdos et al., Comprehensive Functional Maps of the Antigen binding Site of an Anti-ErbB2 Antibody Obtained with Shotgun Scanning Mutagenesis, 2002, Journal of Molecular Biology, vol. 320, pp. 415-428.*

U.S. Appl. No. 12/795,618, "Compositions and Methods of the Therapy and Diagnosis of Influenza", filed on Jun. 7, 2010.*

De Filette et al., "An influenza A vaccine based on tetrameric ectodomain of matrix protein 2", *J. Biol. Chem.*, 283(17):11382-11387 (2008).

Feng et al., "Influenza A virus infection engenders a poor antibody response against the ectodomain of matrix protein 2", *Virology J.*, 3(1):102 (2006).

Zhang et al., "Fine specificity and sequence of antibodies directed against the ectodomain of matrix protein 2 of influenza A virus", *Mol. Immunol.*, 43(14):2195-2206 (2006).

(Continued)

*Primary Examiner* — Benjamin P Blumel
(74) *Attorney, Agent, or Firm* — Mintz Levin Cohn Ferris Glovsky and Popeo, P.C.; Ivor R. Elrifi; Katherine J. Miller

(57) ABSTRACT

The present invention provides novel human anti-influenza antibodies and related compositions and methods. These antibodies are used in the diagnosis and treatment of influenza infection.

10 Claims, 19 Drawing Sheets

U.S. PATENT DOCUMENTS

| | | | |
|---|---|---|---|
| 5,767,285 | A | 6/1998 | Hamann et al. |
| 5,770,701 | A | 6/1998 | McGahren et al. |
| 5,770,710 | A | 6/1998 | McGahren et al. |
| 5,773,001 | A | 6/1998 | Hamann et al. |
| 5,789,199 | A | 8/1998 | Joly et al. |
| 5,821,337 | A | 10/1998 | Carter et al. |
| 5,837,234 | A | 11/1998 | Gentile et al. |
| 5,840,523 | A | 11/1998 | Simmons et al. |
| 5,877,296 | A | 3/1999 | Hamann et al. |
| 6,331,415 | B1 | 12/2001 | Cabilly et al. |
| 6,824,780 | B1 | 11/2004 | Devaux et al. |
| 7,112,439 | B2 | 9/2006 | Johnson et al. |
| 2003/0219442 | A1 | 11/2003 | Mikayama et al. ......... 424/159.1 |
| 2005/0170334 | A1 | 8/2005 | Mikayama et al. .............. 435/5 |
| 2009/0226433 | A1* | 9/2009 | Grandea et al. ............ 424/133.1 |

FOREIGN PATENT DOCUMENTS

| | | |
|---|---|---|
| EP | 183070 A2 | 6/1986 |
| EP | 244234 A2 | 11/1987 |
| EP | 402226 A1 | 12/1990 |
| EP | 404097 A2 | 12/1990 |
| EP | 0425235 A2 | 5/1991 |
| WO | WO-8101145 A1 | 4/1981 |
| WO | WO-8807378 A1 | 10/1988 |
| WO | WO-9013646 A1 | 11/1990 |
| WO | WO-9100360 A1 | 1/1991 |
| WO | WO-9202551 A1 | 2/1992 |
| WO | WO-9220373 A1 | 11/1992 |
| WO | WO-9308829 A1 | 5/1993 |
| WO | WO-9311161 A1 | 6/1993 |
| WO | WO-9316185 A2 | 8/1993 |
| WO | WO-9321232 A1 | 10/1993 |
| WO | WO-9404690 A1 | 3/1994 |
| WO | WO 94/09136 * | 4/1994 |
| WO | WO-9411026 A2 | 5/1994 |
| WO | WO-9607321 A1 | 3/1996 |
| WO | WO-9616673 A1 | 6/1996 |
| WO | WO-9717852 A1 | 5/1997 |
| WO | WO-9738731 A1 | 10/1997 |
| WO | WO-9802463 A1 | 1/1998 |
| WO | WO 03/078600 A2 | 9/2003 |
| WO | WO 2006/061723 A2 | 6/2006 |
| WO | WO 2007/031550 A2 | 3/2007 |
| WO | WO-2007031550 A2 | 3/2007 |
| WO | WO 2007/150020 * | 12/2007 |
| WO | WO-2009/064805 A1 | 5/2009 |
| WO | WO-2010/063675 A1 | 6/2010 |

OTHER PUBLICATIONS

International Search Report for PCT/US2008/083265, mailed Mar. 30, 2009.

Ito et al., "Evolutionary analysis of the influenza A virus M gene with comparison of the M1 and M2 proteins", *J. Virol.*, 65(10):5491-5498 (1991).

Lamb et al., "Influenza virus $M_2$ protein is an integral membrane protein expressed on the infected-cell surface", *Cell*, 40:627-633 (1985).

Zebedee et al., "Influenza A virus $M_2$ protein: monoclonal antibody restriction of virus growth and detection of $M_2$ in virions", *J. Virol.*, 62(8):2762-2772 (1988).

Neirynck et al. "A Universal Influenza A Vaccine Based on the Extracellular Domain of the M2 Protein." *Nat. Med.* (May 10, 1999):1157-1163.

Fu, T.M. et al. "Characterizations of four monoclonal antibodies against M2 protein ectodomain of influenza A virus" Virology, Academic Press, Orlando, US LNKD-D01:10.1016/J.VIROL.Nov. 5, 2008. vol. 385, No. 1, Mar. 1, 2009, pp. 218-226.

Wang, Rongfang et al. "Therapeutic potential of a fully human monoclonal antibody against influenza A virus M2 protein" Antiviral Research, vol. 80, No. 2. Nov. 1, 2008, pp. 168-177.

Altschul et al., "Basic Local Alignment Search Tool", *J. Mol. Biol.*, 215:403-410 (1990).

Altschul et al., "Gapped BLAST and PSI-BLAST: a new generation of protein database search programs", *Nucl. Acids Res.*, 25(17):3389-3402 (1977).

Babcook et al., "A novel strategy for generating monoclonal antibodies from single, isolated lymphocytes producing antibodies of defined specificities", *Proc. Natl. Acad. Sci. USA*, 93(15):7843-7848 (1996).

Bird et al., "Single-Chain Antigen-Binding Proteins", *Science*, 242:423426 (1988).

Bitter et al., "Expression and Secretion Vectors for Yeast", *Meth. Enzymol.*, 53:516-544 (1987).

Bolton et al., "The Labelling of Proteins to High Specific Radioactivities by Conjugation to a $^{125}$I-Containing Acylating Agent", *Biochem J.*, 133:529-539 (1973).

Brennan et al., "Preparation of Bispecific Antibodies by Chemical Recombination of Monoclonal Immunoglobulin $G_1$ Fragments", *Science*, 229:81-83 (1985).

Broglie et al., "Light-Regulated Expression of a Pea Ribulose-1,5-Bisposphate Carboxylase Small Subunit Gene in Transformed Plant Cells", *Science*, 224:838-843 (1984).

Bruggemann et al., "Designer Mice: The Production of Human Antibody Repertoires in Transgenic Animals", *Year in Immunol.*, 7:33-40 (1993).

Capel et al., "Heterogeneity of Human IgG Fc Receptors", *Immunomethods*, 4:25-34 (1994).

Carlsson et al., "Protein Thiolation and Reversible Protein-Protein Conjugation", *Biochem. J.*, 173:723-737 (1978).

Caron et al., "Engineered humanized dimeric forms of IgG are more effective antibodies", *J. Exp. Med.*, 176(4):1191-1195 (1992).

Carter et al., "High Level *Escherichia coli* Expression and Production of a Bivalent Humanized Antibody Fragment", *Bio/Tech.*, 10:163-167 (1992).

Casadevall, "Antibodies for defense against biological attack", *Nat. Biotechnol.*, 20:114 (2002).

Chari et al., "Immunoconjugates Containing Novel Maytansinoids: Promising Anticancer Drugs", *Cancer Res.*, 52:127-131 (1992).

Chothia et al., "Canonical Structures for the Hypervariable Regions of Immunoglobulins", *J. Mol. Biol.*, 196:901-917 (1987).

Chothia et al., "Conformations of immunoglobulin hypervariable regions", *Nature*, 342:877-883 (1989).

Clackson et al., "Making antibody fragments using phage display libraries", *Nature*, 352:624-628 (1991).

Clynes et al., "Fc receptors are required in passive and active immunity to melanoma", *Proc. Natl. Acad. Sci. USA*, 95:652-656 (1998).

Colbere-Garapin et al., "A New Dominant Hybrid Selective Marker for Higher Eukaryotic Cells", *J. Mol. Biol.*, 150:1-14 (1981).

Coruzzi et al., "Tissue-specific and light-regulated expression of pea nuclear gene encoding the small subunit of ribulose-1,5-bisphosphate carboxylase", *EMBO J.*, 3(8):1671-1679 (1984).

Cunningham et al., "High-Resolution Epitope Mapping of hGH-Receptor Interactions by Alanine-Scanning Mutagenesis", *Science*, 244:1081-1085 (1989).

Daeron, M., "Fc Receptor Biology", *Ann. Rev. Immunol.*, 15:203-234 (1997).

Dayhoff, M.O., "A model of evolutionary change in proteins—Matrices for detecting distant relationships", in *Atlas of Protein Sequence and Structure*, National Biomedical Research Foundation, Washington, DC, 5(Suppl. 3) pp. 345-358 (1978).

de Haas et al., "Fcγ receptors of phagocytes" *J. Lab. Clin. Med.*, 126:330-341 (1995).

Engelhard et al., "The insect tracheal system: A conduit for the systemic spread of *Autographa califomica* M nuclear polyhedrosis virus", *Proc. Natl. Acad. Sci. USA*, 91:3224-3227 (1994).

Eppstein et al., "Biological activity of liposome-encapsulated murine interferon γ is mediated by a cell membrane receptor", *Proc. Natl. Acad. Sci. USA*, 82:3688-3692 (1985).

Fraker et al., "Protein and Cell Membrane Iodinations with a Sparingly Soluble Chloroamide, 1,3,4,6-Tetrachloro-3a,5a-Diphenylglycoluril", *Biochem. Biophys. Res. Comm.*, 80:849-857 (1978).

Gabizon et al., "Pharmacokinetics and Tissue Distribution of Doxorubicin Encapsulated in Stable Liposomes With Long Circulation Times", *J. Natl. Cancer Inst.*, 81(19):1484-1488 (1989).

Gazzano-Santoro et al., "A non-radioactive complement-dependent cytotoxicity assay for anti-CD20 monoclonal antibody", *J. Immunol. Meth.*, 202:163-171 (1996).

GenBank Accession No. AB019437 dated Jul. 2, 2008.
GenBank Accession No. J00248 dated Apr. 11, 2001.
GenBank Accession No. L10088 dated Nov. 9, 1994.
GenBank Accession No. M29812 dated Feb. 26, 2002.
GenBank Accession No. M95114 dated Apr. 27, 1993.
GenBank Accession No. M95117 dated Apr. 27, 1993.
GenBank Accession No. M99679 dated Oct. 17, 2007.
GenBank Accession No. X56360 dated May 7, 1992.
GenBank Accession No. X59312 dated Nov. 14, 2006.
GenBank Accession No. X59315 dated Nov. 14, 2006.
GenBank Accession No. X59318 dated Nov. 14, 2006.
GenBank Accession No. X70208 dated Nov. 14, 2006.
GenBank Accession No. X92218 dated Oct. 30, 1995.
GenBank Accession No. Y14865 dated Oct. 23, 2008.
GenBank Accession No. Z27504 dated Jun. 21, 1994.
Goodman et al., "Immunoglobulin Proteins", in *Basic and Clinical Immunology*, 8th Ed., Daniel P. Stties, Abba I. Terr and Tristram G. Parslow (eds.), Appleton & Lange, Norwalk, CT, Ch. 6, pp. 66-79 (1994).
Gruber et al., "Efficient Tumor Cell Lysis Mediated by a Bispecific Single Chain Antibody Expressed in *Escherichia coli*", *J. Immunol.*, 152:5368-5374 (1994).
Guss et al., "Structure of the IgG-binding regions of streptococcal protein G", *EMBO J.*, 5(7):1567-1575 (1986).
Guyer et al., "Immunoglobin Binding by Mouse Intestinal Epithelial Cell Receptors", *J. Immunol.*, 117(2):587-593 (1976).
Hartman et al., "Two dominant-acting selectable markers for gene transfer studies in mammalian cells", *Proc. Natl. Acad. Sci. USA*, 85:8047-8051 (1988).
Hein, J., "Unified Approach to Alignment and Phylogenes", *Meth. Enzymol.*, 183:626-645 (1990).
Henikoff et al., "Amino acid substitution matrices from protein blocks", *Proc. Nat'l. Acad. Sci. U.S.A.*, 89:10915-10929 (1989).
Higgins et al., "Fast and sensitive multiple sequence alignments on a microcomputer", *CABIOS*, 5:151-153 (1989).
Hollinger et al., "Diabodies: Small bivalent and bispecific antibody fragments", *Proc. Natl. Acad. Sci. USA*, 90:6444-6448 (1993).
Honneger et al., "Yet Another Numbering Scheme for Immunoglobulin Variable Domains: An Automatic Modeling and Analysis Tool", *J. Mol. Biol.*, 309:657-670 (2001).
Hwang et al., "Hepatic uptake and degradation of unilamellar sphingomyelin/cholesterol liposomes: A kinetic study", *Proc. Natl. Acad. Sci. USA*, 77(7):4030-4034 (1980).
Igarashi et al., "Human immunodeficiency virus type 1 neutralizing antibodies accelerate clearance of cell-free virions from blood plasma", *Nat. Med.*, 5(2):211-216 (1999).
Jakobovits et al., "Analysis of homozygous mutant chimeric mice: Deletion of the immunoglobulin heavy-chain joining region blocks B-cell development and antibody production", *Proc. Natl. Acad. Sci. USA*, 90:2551-2555 (1993).
Jakobovits et al., "Germ-line transmission and expression of a human-derived yeast artificial chromosome", *Nature*, 362:255-258 (1993).
Jones et al., "Replacing the complementarity-determining regions in a human antibody with those from a mouse", *Nature*, 321:522-525 (1986).
Keller et al., "Passive Immunity in Prevention and Treatment of Infectious Diseases", *Clin. Microbiol. Rev.*, 13(4):602-614 (2000).
Kim et al., "Localization of the site of the murine IgG1 molecule that is involved in binding to the murine intestinal Fc receptor", *Eur. J. Immunol.*, 24:2429-2434 (1994).
Kohler et al., "Continuous cultures of fused cells secreting antibody of predefined specificity", *Nature*, 256:495-497 (1975).
Kostelny et at "Formation of a Bispecific Antibody by the Use of Leucine Zippers", *J. Immunol.*, 148(5):1547-1553 (1992).
Kroll et al., "A Multifunctional Prokaryotic Protein Expression System: Overproduction, Affinity Purification, and Selective Detection", *DNA Cell Biol.*, 12(5):441-453 (1993).
Kyte et al., "A simple method for displaying the hydropathic character of a protein", *J. Mol. Biol.*, 157(1):105-132 (1982).
Lefranc et al., "IMGT, the international ImMunoGeneTics database", *Nucl. Acids Res.*, 27(1):209-212 (1999).
Lindmark et al., "Binding of immunoglobulins to Protein A and Immunoglobulin Levels in Mammalian Sera", *J. Immunol. Meth.*, 62:1-13 (1983).
Liu et al., "Eradication of large colon tumor xenografts by targeted delivery of maytansinoids", *Proc. Natl. Acad. Sci. USA*, 93:8618-8623 (1996).
Logan et al., "Adenovirus tripartite leader sequence enhances translation of mRNAs late after infection", *Proc. Natl. Acad. Sci. USA*, 81:3655-3659 (1984).
Lowy et al., "Isolation of Transforming DNA: Cloning the Hamster aprt Gene", *Cell*, 22:817-823 (1980).
Macken et al., The value of a database in surveillance and vaccine selection, in Options for the Control of Influenza IV., A.D.M.E., Osterhaus & Hampson, Eds., Elsevier Science, Amsterdam, pp. 103-106 (2001).
Maddox et al., "Elevated Serum Levels in Human Pregancy of a Molecule Immunochemically Similar to Eosinophil Granule Major Basic Protein", *J. Exp. Med.*, 158:1211-1226 (1983).
Marks et al., By-passing Immunization. Human Antibodies from V-gene Libraries Displayed of Phage, *J. Mol. Biol.*, 222:581-597 (1991).
Martin et al., "Irreversible Coupling of Immunoglobulin Fragments to Preformed Vesicles. An Improved Method for Liposome Targeting", *J. Biol. Chem.*, 257(1):286-288 (1982).
Massey, R. J., "Catalytic antibodies catching on", *Nature*, 328:457-458 (1987).
Mather et al., "Culture of Testicular Cells in Hormone-Supplemented Serum-Free Medium", *Ann. N.Y. Acad. Sci.*, 383:44-68 (1982).
Mather, J. P., "Establishment and Characterization of Two Distinct Mouse Testicular Epithelial Cell lines", *Biol. Reprod.*, 23:243-252 (1980).
Millstein et al., "Hybrid hybridomas and their use in immunohistochemistry", *Nature*, 305:537-540 (1983).
Morimoto et al., "Single-step purification of F(ab')$_2$ fragments of mouse monoclonal antibodies (immunoglobulins G1) by hydrophobic interaction high performance liquid chromatography using TSKgel Phenyl-5PW", *J. Biochem. Biophys. Meth.*, 24:107-117 (1992).
Morrison et al., "Chimeric human antibody molecules: Mouse antigen-binding domains with human constant region domains", *Proc. Natl. Acad. Sci. USA*, 81:6851-6855 (1984).
Morrison, M., "The Determination of the Exposed Proteins on Membranes by the Use of Lactoperoxidase", *Meth. Enzymol.*, 32b:103-109 (1974).
Murakami et al., "Cell cycle regulation, oncogenes, and antineoplastic drugs", in *The Molecular Basis of Cancer*, Mendelsohn and Israel, Eds., W.B. Saunders, Philadelphia, PA, Ch. 1, p. 13 (1995).
Murry, L. E., "Genetic Engineering", in *McGraw Hill Yearbook of Science and Tech.*, McGraw Hill, New York, pp. 191-196 (1992).
Myers et al., "Optimal alignments in linear space", *CABIOS*, 4(1):11-17 (1988).
Needleman et al., "A General Method Applicable to the Search for Similarities in the Amino Acid Sequence of Two Proteins", *J. Mol. Biol.*, 48:443-453 (1970).
Neuberger et al., "Recombinant antibodies possessing novel effector functions", *Nature*, 312:604-608 (1984).
Pearson et al., "Improved tools for biological sequence comparison", *Proc. Natl. Acad. Sci. USA*, 85:2444-2448 (1988).
Pluckthun et al., "Expression of Functional Antibody Fv and Fab Fragments in *Escherichia coli*", *Meth. Enzymol.*, 178:497-515 (1989).
Pluckthun, A., "Antibodies from *Escherichia coli*", in *The Pharmacology of Monoclonal Antibodies*, Rosenburg and Moore Eds., Springer-Verlag, New York, Ch. 11, vol. 113, pp. 269-315 (1994).
Porath, J., "Immobilized Metal Ion Affinity Chromatography", *Prot. Exp. Purif*, 3:263-281 (1992).
Presta, L. G., "Antibody engineering", *Curr. Opin. Struct. Biol.*, 2:593-596 (1992).
Ravetch et al., "Fc Receptors", *Ann. Rev. Immunol.*, 9:457-492 (1991).
Rhodes et al., "Transformation of Maize by Electroporation of Embryos", *Meth. Mol. Biol.*, 55:121-131 (1995).

Riechmann et al., "Reshaping human antibodies for therapy", *Nature*, 332:323-327 (1988).

Robinson, D. F., "Comparison of Labeled Trees with Valency Three", *J. Comb. Theor.*, 11:105-119 (1971).

Ruiz et al., "IMGT, the international ImMunoGeneTics database", *Nucl. Acids Res.*, 28:219-221 (2000).

Saitou et al, "The Neighbor-joining Method: A New Method for Reconstructing Phylogenetic Trees", *Mol. Biol. Evol.*, 4:406-425 (1987).

Sanger et al., "DNA sequencing with chain-terminating inhibitors", *Proc. Natl. Acad. Sci. USA.*, 74(12):5463-5467 (1977).

Scatchard, G., "The Attractions of Proteins for Small Molecules and Ions", *Ann. N.Y. Acad. Sci. U.S.A.*, 51:660-672 (1949).

Shalaby et al., "Development of Humanized Bispecific Antibodies Reactive with Cytotoxic Lymphocytes and Tumor Cells Overexpressing the *HER2* Protooncogene", *J. Exp. Med.*, 175:217-225 (1992).

Shibata et al., "Neutralizing antibody directed against the HIV-1 envelope glycoprotein can completely block HIV-1/SIV chimeric virus infections of macaque monkeys", *Nature Med.*, 5(2):204-210 (1999).

Shopes, B.J., "A Genetically Engineered Human IgG Mutant with Enhanced Cytolytic Activity", *J. Immunol.*, 148:2918-2922 (1992).

Smith et al., "Comparison of Biosequences", Adv. Applied Math., 2:482-489 (1981).

Stevenson et al., "A chimeric antibody with dual Fc regions (*bis*FabFc) prepared by manipulations at the IgG hinge", *Anti-Cancer Drug Des.*, 3:219-230 (1989).

Suresh et al., "Bispecific Monoclonal Antibodies from Hybrid Hybridomas", *Meth. Enzymol.*, 121:210-228 (1986).

Syvanen et al., "Preparation of $^{125}$I-Catalytic Subunit of Aspartate Transcarbamylase and Its Use in Studies of the Regulatory Subunit", *J. Biol. Chem.*, 284(11):3762-3765 (1973).

Takamatsu, N., "Expression of bacterial chloramphenicol acetyltransferase gene in tobacco plants mediated by TMV-RNA", *EMBO J.*, 6(2):307-311 (1987).

Traunecker et al., "Bispecific single chain molecules (Janusins) target cytotoxic lymphocytes on HIV infected cells", *EMBO J.*, 10(12):3655-3659 (1991).

Tutt et al., "Trispecific F(ab$^1$)$_3$ derivatives that use cooperative signaling via the TCR/CD3 complex and CD2 to activate and redirect resting cytotoxic T cells", *J. Immunol.*, 147(1):60-69 (1991).

Urlaub et at "Isolation of Chinese hamster cell mutant deficient in dihydrofolate reductase activity", *Proc. Natl. Acad. Sci. USA*, 77(7):4216-4220 (1980).

Van Heeke et al., "Expression of Human Asparagine Synthetase in *Escherichia coli*", *J. Biol. Chem.*, 264(10):5503-5509 (1989).

Verhoeyen et al., "Reshaping Human Antibodies: Grafting an Antilysozyme Activity", *Science*, 239:1534-1536 (1988).

Vitetta et al., "Redesigning Nature's Poisons to Create Anti-Tumor Reagents", *Science*, 238:1098-1104 (1987).

Wigler et al., "Transfer of Purified Herpes Virus Thymidine Kinase Gene to Cultured Mouse Cells", *Cell*, 11:223-232 (1977).

Wigler et al., "Transformation of mammalian cells with an amplifiable dominant-acting gene", *Proc. Natl. Acad. Sci. USA.*, 77(6):3567-3570 (1980).

Wilbur et al., "Rapid similarity searches of nucleic acid and protein data banks", *Proc. Natl. Acad. Sci. USA*, 80:726-730 (1983).

Winter et al., "The Expression of Heat Shock Protein and Cognate Genes During Plant Development", *Results Probl. Cell Differ.*, 17:85-105 (1991).

Wolff et al., "Monoclonal Antibody Homodimers: Enhanced Antitumor Activity in Nude Mice", *Cancer Res.*, 53:2560-2565 (1993).

Yaniv, M., "Enhancing elements for activation of eukaryotic promoters", *Nature*, 297:17-18 (1982).

Zapata et al., "Engineering linear F(ab')$_2$ fragments for efficient production in *Eschericha coli* and enhanced antiproliferative activity", *Protein Eng.*, 8(10):1057-1062 (1995).

\* cited by examiner

FULL-LENGTH M2 VARIANT BINDING
AMINO ACID SEQUENCES OF EXTRACELLULAR DOMAINS OF M2 VARIANTS.

| # | Strain | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|---|
| 1 | A.Brevig Mission.1.1918.H1N1 | M | S | L | L | T | E | V | E | T | P | T | R | N | E | W | G | C | R | C | N | D | S | S | D |
| 2 | A.Fort Monmouth.1.1947.H1N1 | M | S | L | L | T | E | V | E | T | P | T | K | N | E | W | E | C | R | C | N | D | S | S | D |
| 3 | A.Singapore.02.2005.H3N2 | M | S | L | L | T | E | V | E | T | P | I | R | N | E | W | E | C | R | C | N | D | S | S | D |
| 115 | A.Wisconsin.10.98.H1N1 | M | S | L | L | T | E | V | E | T | P | I | K | N | G | W | E | C | K | C | N | D | S | S | D |
| 5 | A.Wisconsin.301.1976.H1N1 | M | S | L | L | T | E | V | E | T | P | I | R | S | E | W | G | C | R | C | N | D | S | S | D |
| 6 | A.Panama.1.66.H2N2 | M | S | F | L | P | E | V | E | T | P | I | R | N | E | W | G | C | R | C | N | D | S | S | D |
| 7 | A.New York.321.1999.H3N2 | M | S | L | L | T | E | V | E | T | P | I | R | N | E | W | G | C | R | C | N | D | S | S | N |
| 8 | A.Caracas.1.71.H3N2 | M | S | L | L | T | E | V | E | T | P | I | R | K | E | W | G | C | R | C | N | D | S | S | D |
| 9 | A.Taiwan.3.71.H3N2 | M | S | F | L | T | E | V | E | T | P | I | R | N | E | W | G | C | R | C | N | D | S | S | D |
| 10 | A.Wuhan.359.95.H3N2 | M | S | L | P | T | E | V | E | T | P | I | R | S | E | W | G | C | R | C | N | D | S | S | D |
| 11 | A.Hong Kong.1144.99.H3N2 | M | S | L | L | P | E | V | E | T | P | I | R | N | E | W | G | C | R | C | N | D | S | S | D |
| 12 | A.Hong Kong.1180.99.H3N2 | M | S | L | L | P | E | V | E | T | P | I | R | N | G | W | G | C | R | C | N | D | S | S | D |
| 13 | A.Hong Kong.1774.99.H3N2 | M | S | L | L | T | E | V | E | T | P | T | R | N | G | W | E | C | R | C | S | G | S | S | D |
| 14 | A.New York.217.02 H1N2 | M | S | L | L | T | E | V | E | T | P | I | R | N | E | W | E | Y | R | C | N | D | S | S | D |
| 15 | A.New York.300.2003.H1N2 | M | S | L | L | T | E | V | E | T | P | I | R | N | E | W | E | Y | R | C | S | D | S | S | D |
| 16 | A.swine.Spain.54008.2004.H3N2 | M | S | L | L | T | E | V | E | T | P | T | R | N | G | W | E | C | R | Y | S | D | S | S | D |
| 17 | A.Guangzhou.333.99.H9N2 | M | S | F | L | T | E | V | E | T | L | T | R | N | G | W | E | C | R | C | S | D | S | S | D |
| 18 | A.Hong Kong.1073.99.H9N2 | M | S | L | L | T | E | V | E | T | L | T | R | N | G | W | E | C | K | C | R | D | S | S | D |
| 19 | A.Hong Kong.1.68.H3N2 | M | S | L | L | T | E | V | E | T | P | I | R | N | E | W | G | C | R | C | N | D | S | S | D |
| 20 | A.swine.Hong Kong.126.1982.H3N2 | M | S | L | L | T | E | V | E | T | P | I | R | S | E | W | G | C | R | C | N | D | S | G | D |
| 21 | A.New York.703.1995.H3N2 | M | S | L | L | T | E | V | E | T | P | I | R | N | E | W | E | C | R | C | N | G | S | S | D |
| 22 | A.swine.Quebec.192.81 H1N1 | M | S | L | P | T | E | V | E | T | P | I | R | N | E | W | G | C | R | C | N | D | S | S | D |
| 23 | A.Puerto Rico.8.34.H1N1 | M | S | L | L | T | E | V | E | T | P | I | R | N | E | W | G | C | R | C | N | G | S | S | D |
| 24 | A.Hong Kong.485.97.H5N1 | M | S | L | L | T | E | V | D | T | L | T | R | N | G | W | G | C | R | C | S | D | S | S | D |
| 25 | A.Hong Kong.542.97.H5N1 | M | S | L | L | T | E | V | E | T | L | T | K | N | G | W | G | C | R | C | S | D | S | S | D |
| 26 | A.silky chicken.Shantou.1826.2004.H | M | S | L | L | T | E | V | E | T | P | T | R | N | G | W | E | C | K | C | S | D | S | S | D |
| 27 | A.chicken.Taiwan.0305.04.H6N1 | M | S | L | L | T | E | V | E | T | H | T | R | N | G | W | E | C | K | C | S | D | S | S | D |
| 28 | A.Quail.Arkansas.16309-7.94.H7N3 | M | S | L | L | T | E | V | K | T | P | T | R | N | G | W | E | C | K | C | S | D | S | S | D |
| 29 | A.Hong Kong.486.97.H5N1 | M | S | L | L | T | E | V | E | T | L | T | R | N | G | W | G | C | R | C | S | D | S | S | D |
| 30 | A.Chicken.Pennsylvania.13552-1.98 | M | S | L | L | T | E | V | E | T | P | T | R | D | G | W | E | C | K | C | S | D | S | S | D |
| 31 | A.chicken.Heilongjiang.48.01.H9N2 | M | S | L | L | T | E | V | E | T | P | T | R | N | G | W | E | C | R | C | S | D | S | S | D |
| 32 | A.swine.Korea.S5.2005.H1N2 | M | S | L | L | T | E | V | E | T | P | T | R | N | G | W | E | C | K | C | N | D | S | S | D |
| 33 | A.Hong Kong.1073.99.H9N2 | M | S | L | L | T | E | V | E | T | L | T | R | N | G | W | E | C | K | C | S | D | S | S | D |
| 34 | A.Wisconsin.3523.88.H1N1 | M | S | L | L | T | E | V | E | T | P | I | R | N | E | W | G | C | K | C | N | D | S | S | D |
| 35 | A.X-31 Vaccine strain H3N2 | M | S | F | L | T | E | V | E | T | P | I | R | N | E | W | G | C | R | C | N | G | S | S | D |
| 36 | A.Chicken.Rostock.8.1934.H7N1 | M | S | L | L | T | E | V | E | T | P | T | R | N | G | W | E | C | R | C | N | D | S | S | D |
| 37 | A.environment.New York. 16326-1.2 | M | S | L | L | T | E | V | E | T | P | I | R | K | G | W | E | C | N | C | S | D | S | S | D |
| 38 | A.Indonesia.560H.2006.H5N1 | M | S | L | L | T | E | V | E | T | P | T | R | N | E | W | E | C | R | C | S | D | S | S | D |
| 39 | A.Chicken.Hong Kong.SF1.03.H9N2 | M | S | L | L | T | G | V | E | T | H | T | R | N | G | W | G | C | K | C | S | D | S | S | D |
| 40 | A.chicken.Hong Kong YU427.03.H9N | M | S | L | L | P | E | V | E | T | H | T | R | N | G | W | G | C | R | C | S | D | S | S | D |

EXTRACELLULAR SEQUENCE OF D20 IS IDENTICAL
TO #19, HK483 TO #29, AND VN1203 TO #38.

Fig. 3A

CROSS REACTIVITY BINDING OF ANTI-M2 ANTIBODIES TO VARIANT M2 PEPTIDES

| | | | | ELISA (OD 450) | | | |
|---|---|---|---|---|---|---|---|
| seqNo | Name | Size | Description | 14C2 | 8i10 | 23K12 | 2N9 |
| 116 | M2 | 23 aa | SLLTEVETPIRNEWGCRCNDSSD | + | - | - | - |
| 117 | M2SG | 23 aa | SLLTEVETPIRSEWGCRCNDSGD | + | - | - | - |
| 118 | M2EG | 23 aa | SLLTEVETPIRNEWECRCNGSSD | + | - | - | - |
| 119 | M2P | 23 aa | SLPTEVETPIRNEWGCRCNDSSD | + | - | - | - |
| 120 | M2G | 23 aa | SLLTEVETPIRNEWGCRCNGSSD | + | - | - | - |
| 121 | M2DLTGS | 23 aa | SLLTEVDTLTRNGWGCRCSDSSD | - | - | + | - |
| 122 | M2KNS | 23 aa | SLLTEVETPIRKEWGCNCSDSSD | + | - | - | - |
| 123 | M2LGS | 23 aa | SLLTEVETLIRNGWGCRCSDSSD | - | - | - | - |
| 124 | M2LTKGS | 23 aa | SLLTEVETLTKNGWGCRCSDSSD | - | - | - | - |
| 125 | M2SY | 23 aa | SLLTEVETPIRSEWGCRYNDSSD | + | - | - | - |
| 126 | M2TGEKS | 23 aa | SLLTEVETPTRNGWECKCSDSSD | + | - | - | - |
| 127 | M2HTGEKS | 23 aa | SLLTEVETHTRNGWECKCSDSSD | - | - | - | - |
| 128 | M2KTGEKS | 23 aa | SLLTEVKTPTRNGWECKCSDSSD | - | - | - | - |
| 129 | M2LTGS | 23 aa | SLLTEVETLTRNGWGCRCSDSSD | - | - | + | - |
| 130 | M2TDGEKS | 23 aa | SLLTEVETPTRDGWECKCSDSSD | + | - | - | - |
| 131 | M2TGS | 23 aa | SLLTEVETPTRNGWGCRCSDSSD | + | - | W | - |
| 132 | M2TGEK | 23 aa | SLLTEVETPTRNGWECKCNDSSD | + | - | - | - |
| 133 | M2LTGEKS | 23 aa | SLLTEVETLTRNGWECKCSDSSD | - | - | W | - |
| 134 | M2K | 23 aa | SLLTEVETPIRNEWGCKCNDSSD | + | W | + | - |
| 135 | M2FG | 23 aa | SFLTEVETPIRNEWGCRCNGSSD | + | W | - | - |
| 136 | M2TGE | 23 aa | SLLTEVETPTRNGWECRCNDSSD | + | - | - | - |
| 137 | M2KGENS | 23 aa | SLLTEVETPIRKGWECNCSDSSD | + | - | - | - |
| 138 | M2TES | 23 aa | SLLTEVETPTRNEWECRCSDSSD | + | - | - | - |
| 139 | M2GHTGKS | 23 aa | SLLTGVETHTRNGWGCKCSDSSD | - | - | - | - |
| 140 | M2PHTGS | 23 aa | SLLPEVETHTRNGWGCRCSDSSD | - | - | - | - |

PERCENTAGE COMPARED RELATIVE TO BINDING TO WILD-TYPE PEPTIDE (Seq 116) NOTE: mAbs WERE TESTED AT 5 μg/mL

>25 %    -    NO BINDING
    25 - 40 %    W    WEAK BINDING
    > 40 %    +    POSITIVE BINDING

Fig. 6A

BINDING ACTIVITY OF M2 ANTIBODIES TO TRUNCATED M2 PEPTIDES

| seqNo | Name | Size | Description | 14C2 | 8i10 | 23K12 | 2N9 |
|---|---|---|---|---|---|---|---|
| 116 | M2 | 23 aa | SLLTEVETPIRNEWGCRCNDSSD | 3.85 | 0.11 | 0.22 | 0.06 |
| 141 | M16 | 16 aa | LLTEVETPIRNEWGCR | 3.94 | 0.09 | 0.21 | 0.09 |
| 142 | M15 | 15 aa | LTEVETPIRNEWGCR | 3.95 | 0.09 | 0.21 | 0.09 |
| 143 | M12 | 12 aa | VETPIRNEWGCR | 0.15 | 0.09 | 0.20 | 0.09 |
| 144 | CM17 | 17 aa | ETPIRNEWGCRCNDSSD | 0.19 | 0.11 | 0.34 | 0.11 |
| 145 | CM16 | 16 aa | TPIRNEWGCRCNDSSD | 0.23 | 0.13 | 0.35 | 0.12 |
| 146 | CM15 | 15 aa | PIRNEWGCRCNDSSD | 0.19 | 0.12 | 0.34 | 0.11 |
| 147 | CM14 | 14 aa | IRNEWGCRCNDSSD | 0.23 | 0.14 | 0.36 | 0.13 |
| 148 | CM13 | 13 aa | RNEWGCRCNDSSD | 0.22 | 0.14 | 0.34 | 0.13 |
| 149 | CM12 | 12 aa | NEWGCRCNDSSD | 0.27 | 0.14 | 0.39 | 0.14 |
| 150 | NM17 | 17 aa | SLLTEVETPIRNEWGCR | 3.99 | 0.26 | 0.58 | 0.10 |
| 151 | NM16 | 16 aa | SLLTEVETPIRNEWGC | 3.90 | 0.29 | 0.62 | 0.09 |
| 152 | NM15 | 15 aa | SLLTEVETPIRNEWG | 3.97 | 0.12 | 0.30 | 0.11 |
| 153 | NM14 | 14 aa | SLLTEVETPIRNEW | 3.97 | 0.11 | 0.24 | 0.09 |
| 154 | NM13 | 13 aa | SLLTEVETPIRNE | 0.18 | 0.11 | 0.25 | 0.10 |
| 155 | NM12 | 12 aa | SLLTEVETPIRN | 0.20 | 0.10 | 0.24 | 0.09 |
| 156 | NM11 | 11 aa | SLLTEVETPIR | 0.21 | 0.13 | 0.30 | 0.12 |
| 157 | NM10 | 10 aa | SLLTEVETPI | 0.17 | 0.10 | 0.24 | 0.10 |
| 158 | NM8 | 8 aa | SLLTEVET | 0.15 | 0.10 | 0.20 | 0.09 |
| 159 | NM7 | 7 aa | SLLTEVE | 0.14 | 0.10 | 0.20 | 0.08 |
| 160 | NM9 | 9 aa | SLLTEVETP | 0.21 | 0.12 | 0.30 | 0.19 |
| 1 | M2e | 24 aa | MSLLTEVETPIRNEWGCRCNDSSD | 3.98 | 0.13 | 0.43 | 0.10 |
| CMV | HVIR1 | | | 0.16 | 0.11 | 0.21 | 3.99 |

NOTE: mAbs WERE TESTED AT 5 μg/mL

SPDQ M2e mAbs APPEAR TO BIND HIGHLY CONSERVED N-TERMINAL REGION OF M2e

NH22 - M2e SEQUENCE - COOH
M S L L T E V E T P I R N E W G C R C N D S S D

Fig. 8

ANTI-M2 mAb BIND INFLUENZA

Fig. 9

| | | | | | | | | | 10 | | | | | | | | | | 20 | | | | | | | | | | 30 | | | | | | |
|---|---|---|---|---|---|---|---|---|---|---|---|---|---|---|---|---|---|---|---|---|---|---|---|---|---|---|---|---|---|---|---|---|---|---|---|
| Translation of mp 73 21B15 | A | S | T | M | D | M | R | V | L | A | Q | L | L | L | W | L | R | G | A | R | C | D | I | Q | V | T | Q | S | P | S | S | L |
| Translation of mp 147 8I10 | A | S | T | M | D | M | R | V | L | A | Q | L | L | L | W | L | R | G | A | R | C | D | I | Q | M | T | Q | S | P | S | S | L |
| Translation of mp 137 23K12 | A | S | T | M | D | M | R | V | L | A | Q | L | L | L | W | L | R | G | A | R | C | D | I | Q | M | T | Q | S | P | S | S | L |

| | | | | | | 40 | | | | | | | | | | 50 | | | | | | | | | | 60 | | | | | | | | | 70 | |
|---|---|---|---|---|---|---|---|---|---|---|---|---|---|---|---|---|---|---|---|---|---|---|---|---|---|---|---|---|---|---|---|---|---|---|---|---|
| Translation of mp 73 21B15 | S | A | S | V | G | D | R | V | T | I | T | C | R | A | S | Q | N | I | Y | K | Y | L | N | W | Y | Q | Q | R | P | G | K | A | P | K | G | L |
| Translation of mp 147 8I10 | S | A | S | V | G | D | R | V | T | I | T | C | R | A | S | Q | N | I | Y | K | Y | L | N | W | Y | Q | Q | R | P | G | K | A | P | K | G | L |
| Translation of mp 137 23K12 | S | A | S | V | G | D | R | V | T | I | T | C | R | T | S | Q | S | I | S | S | Y | L | N | W | Y | Q | Q | K | P | G | K | A | P | K | L | L |

| | | | | 80 | | | | | | | | | | 90 | | | | | | | | | | 100 | | | | | | | | | | | | |
|---|---|---|---|---|---|---|---|---|---|---|---|---|---|---|---|---|---|---|---|---|---|---|---|---|---|---|---|---|---|---|---|---|---|---|---|---|
| Translation of mp 73 21B15 | I | S | A | A | S | G | L | Q | S | G | V | P | S | R | F | S | G | S | G | S | G | T | D | F | T | L | T | I | T | S | L | Q | P | E | D | F |
| Translation of mp 147 8I10 | I | S | A | A | S | G | L | Q | S | G | V | P | S | R | F | S | G | S | G | S | G | T | D | F | T | L | T | I | T | S | L | Q | P | E | D | F |
| Translation of mp 137 23K12 | I | Y | A | A | S | S | L | Q | S | G | V | P | S | R | F | S | G | S | G | S | G | T | D | F | T | L | T | I | S | G | L | Q | P | E | D | F |

| | | | 110 | | | | | | | | | | 120 | | | | | | | | | 130 | | | | | |
|---|---|---|---|---|---|---|---|---|---|---|---|---|---|---|---|---|---|---|---|---|---|---|---|---|---|---|---|
| Translation of mp 73 21B15 | A | T | Y | Y | C | Q | Q | S | Y | S | P | P | L | T | F | G | G | G | T | R | V | D | I | K | R | T |
| Translation of mp 147 8I10 | A | T | Y | Y | C | Q | Q | S | Y | S | P | P | L | T | F | G | G | G | T | R | V | E | I | K | R | T |
| Translation of mp 137 23K12 | A | T | Y | Y | C | Q | Q | S | Y | S | M | P | - | A | F | G | Q | G | T | K | L | E | I | K | R | T |

| | | | | | | | | | 10 | | | | | | | | | | 20 | | | | | | | | | |
|---|---|---|---|---|---|---|---|---|---|---|---|---|---|---|---|---|---|---|---|---|---|---|---|---|---|---|---|---|
| Translation of mp 81 21B15 | A | S | T | M | K | H | L | W | F | L | L | L | V | A | A | P | S | W | V | L | Q | S | Q | V | Q | L | Q | E | S |
| Translation of mp 145 23K12 | A | S | T | M | E | L | G | L | C | W | F | L | L | V | A | I | L | K | G | V | Q | C | E | V | Q | L | V | E | S |
| Translation of mp 153 8I10 | A | S | T | M | K | H | L | W | F | L | L | L | V | A | A | P | S | W | V | L | Q | S | Q | V | Q | L | Q | E | S |

| | 30 | | | | | | | | | | 40 | | | | | | | | | | 50 | | | | | | | | |
|---|---|---|---|---|---|---|---|---|---|---|---|---|---|---|---|---|---|---|---|---|---|---|---|---|---|---|---|---|---|
| Translation of mp 81 21B15 | G | P | G | L | V | K | P | S | E | T | L | S | L | T | C | T | V | S | G | F | S | I | S | S | Y | Y | W | S |
| Translation of mp 145 23K12 | G | G | G | L | V | Q | P | G | G | S | L | R | L | S | C | A | A | S | G | F | T | V | S | S | N | Y | M | S |
| Translation of mp 153 8I10 | G | P | G | L | V | K | P | S | E | T | L | S | L | T | C | T | V | S | G | F | S | I | S | S | N | Y | Y | W | S |

| 60 | | | | | | | | | | 70 | | | | | | | | | | 80 | | | | | | | | | |
|---|---|---|---|---|---|---|---|---|---|---|---|---|---|---|---|---|---|---|---|---|---|---|---|---|---|---|---|---|---|
| Translation of mp 81 21B15 | I | R | Q | S | P | G | K | G | L | E | W | I | G | F | I | Y | Y | S | G | N | T | K | Y | N | Q | L | K | S |
| Translation of mp 145 23K12 | V | R | Q | A | P | G | K | G | L | E | W | V | S | V | I | Y | Y | G | G | S | T | Y | Y | A | D | S | V | K | G |
| Translation of mp 153 8I10 | I | R | Q | S | P | G | K | G | L | E | W | I | G | F | I | Y | Y | S | G | N | T | K | Y | N | Q | L | K | S |

| | | 90 | | | | | | | | | | 100 | | | | | | | | | | 110 | | | | | | | |
|---|---|---|---|---|---|---|---|---|---|---|---|---|---|---|---|---|---|---|---|---|---|---|---|---|---|---|---|---|---|
| Translation of mp 81 21B15 | R | V | T | I | S | Q | D | T | S | G | G | V | S | L | T | M | S | N | S | V | T | A | A | E | S | A | V | Y | F |
| Translation of mp 145 23K12 | R | F | S | F | S | R | D | N | S | K | N | T | V | F | L | Q | M | N | S | L | R | A | E | D | T | A | V | Y | Y |
| Translation of mp 153 8I10 | R | V | T | I | S | Q | D | T | S | G | G | V | S | L | T | M | S | N | S | V | T | A | A | E | S | A | V | Y | F |

| | 120 | | | | | | | | | | 130 | | | | | | | | | | 140 | | |
|---|---|---|---|---|---|---|---|---|---|---|---|---|---|---|---|---|---|---|---|---|---|---|---|---|
| Translation of mp 81 21B15 | C | A | R | A | S | C | S | G | G | Y | C | I | L | D | Y | W | G | Q | G | T | L | V | T | V | S |
| Translation of mp 145 23K12 | C | A | R | C | L | S | R | M | R | G | Y | G | L | D | V | W | G | Q | G | T | T | V | T | V | S |
| Translation of mp 153 8I10 | C | A | R | A | S | C | S | G | G | Y | C | I | L | D | Y | W | G | Q | G | T | L | V | T | V | S |

US 8,114,402 B2

COMPOSITIONS AND METHODS FOR THE THERAPY AND DIAGNOSIS OF INFLUENZA

RELATED APPLICATIONS

This application is a divisional application of U.S. Ser. No. 12/269,781, filed Nov. 12, 2008, which claims the benefit of provisional applications U.S. Ser. No. 60/987,353, filed Nov. 12, 2007, U.S. Ser. No. 60/987,355, filed Nov. 12, 2007, U.S. Ser. No. 61/053,840 filed May 16, 2008, and U.S. Ser. No. 61/095,208, filed Sep. 8, 2008, the contents of which are each herein incorporated by reference in their entirety.

FIELD OF THE INVENTION

The present invention relates generally to therapy, diagnosis and monitoring of influenza infection. The invention is more specifically related to methods of identifying influenza matrix 2 protein-specific antibodies and their manufacture and use. Such antibodies are useful in pharmaceutical compositions for the prevention and treatment of influenza, and for the diagnosis and monitoring of influenza infection.

BACKGROUND OF THE INVENTION

Influenza virus infects 5-20% of the population and results in 30,000-50,000 deaths each year in the U.S. Although the influenza vaccine is the primary method of infection prevention, four antiviral drugs are also available in the U.S.: amantadine, rimantadine, oseltamivir and zanamivir. As of December 2005, only oseltamivir (TAMIFLU™) is recommended for treatment of influenza A due to the increasing resistance of the virus to amantadine and rimantidine resulting from an amino acid substitution in the M2 protein of the virus.

Disease caused by influenza A viral infections is typified by its cyclical nature. Antigenic drift and shift allow for different A strains to emerge every year. Added to that, the threat of highly pathogenic strains entering into the general population has stressed the need for novel therapies for flu infections. The predominant fraction of neutralizing antibodies is directed to the polymorphic regions of the hemagglutinin and neuraminidase proteins. Thus, such a neutralizing MAb would presumably target only one or a few strains. A recent focus has been on the relatively invariant matrix 2 (M2) protein. Potentially, a neutralizing MAb to M2 would be an adequate therapy for all influenza A strains.

The M2 protein is found in a homotetramer that forms an ion channel and is thought to aid in the uncoating of the virus upon entering the cell. After infection, M2 can be found in abundance at the cell surface. It is subsequently incorporated into the virion coat, where it only comprises about 2% of total coat protein. The M2 extracellular domain (M2e) is short, with the aminoterminal 2-24 amino acids displayed outside of the cell. Anti-M2 MAbs to date have been directed towards this linear sequence. Thus, they may not exhibit desired binding properties to cellularly expressed M2, including conformational determinants on native M2.

Therefore, a long-felt need exists in the art for new antibodies that bind to the cell-expressed M2 and conformational determinants on the native M2.

SUMMARY OF THE INVENTION

The present invention provides fully human monoclonal antibodies specifically directed against M2e. Optionally, the antibody is isolated form a B-cell from a human donor. Exemplary monoclonal antibodies include 8i10, 21B15 and 23K12 described herein. Alternatively, the monoclonal antibody is an antibody that binds to the same epitope as 8i10, 21B15 and 23K12. The antibodies are respectively referred to herein is huM2e antibodies. The huM2e antibody has one or more of the following characteristics: a) binds to an epitope in the extracellular domain of the matrix 2 ectodomain (M2e) polypeptide of an influenza virus; b) binds to influenza A infected cells; or c) binds to influenza A virus.

The epitope that huM2e antibody binds to is a non-linear epitope of a M2 polypeptide. Preferably, the epitope includes the amino terminal region of the M2e polypeptide. More preferably the epitope wholly or partially includes the amino acid sequence SLLTEV (SEQ ID NO:42). Most preferably, the epitope includes the amino acid at position 2, 5 and 6 of the M2e polypeptide when numbered in accordance with SEQ ID NO:1. The amino acid at position 2 is a serine; at position 5 is a threonine; and at position 6 is a glutamic acid.

A huM2e antibody contains a heavy chain variable having the amino acid sequence of SEQ ID NOS: 44 or 50 and a light chain variable having the amino acid sequence of SEQ ID NOS: 46 or 52. Preferably, the three heavy chain CDRs include an amino acid sequence at least 90%, 92%, 95%, 97% 98%, 99% or more identical to the amino acid sequence of NYYWS (SEQ ID NO: 72), FIYYGGNTKYNPSLKS (SEQ ID NO: 74), ASCSGGYCILD (SEQ ID NO: 76), SNYMS (SEQ ID NO: 103), VIYSGGSTYYADSVK (SEQ ID NO: 105), CLSRMRGYGLDV (SEQ ID NO: 107) (as determined by the Kabat method) or ASCSGGYCILD (SEQ ID NO: 76), CLSRMRGYGLDV (SEQ ID NO: 107), GSSISN (SEQ ID NO: 109), FIYYGGNTK (SEQ ID NO: 110), GFTVSSN (SEQ ID NO: 112), VIYSGGSTY (SEQ ID NO: 113) (as determined by the Chothia method) and a light chain with three CDRs that include an amino acid sequence at least 90%, 92%, 95%, 97% 98%, 99% or more identical to the amino acid sequence of RASQNIYKYLN (SEQ ID NO: 59), AASGLQS (SEQ ID NO: 61), QQSYSPPLT (SEQ ID NO: 63), RTSQSISSYLN (SEQ ID NO: 92), AASSLQSGVPSRF (SEQ ID NO: 94), QQSYSMPA (SEQ ID NO: 96) (as determined by the Kabat method) or RASQNIYKYLN (SEQ ID NO: 59), AASGLQS (SEQ ID NO: 61), QQSYSPPLT (SEQ ID NO: 63), RTSQSISSYLN (SEQ ID NO: 92), AASSLQSGVPSRF (SEQ ID NO: 94), QQSYSMPA (SEQ ID NO: 96) (as determined by the Chothia method).

The heavy chain of a M2e antibody is derived from a germ line V (variable) gene such as, for example, the IgHV4 or the IgHV3 germline gene.

The M2e antibodies of the invention include a variable heavy chain ($V_H$) region encoded by a human IgHV4 or the IgHV3 germline gene sequence. A IgHV4 germline gene sequence are shown, e.g., in Accession numbers L10088, M29812, M95114, X56360 and M95117. IgHV3 germline gene sequence are shown, e.g., in Accession numbers X92218, X70208, Z27504, M99679 and AB019437. The M2e antibodies of the invention include a $V_H$ region that is encoded by a nucleic acid sequence that is at least 80% homologous to the IgHV4 or the IgHV3 germline gene sequence. Preferably, the nucleic acid sequence is at least 90%, 95%, 96%, 97% homologous to the IgHV4 or the IgHV3 germline gene sequence, and more preferably, at least 98%, 99% homologous to the IgHV4 or the IgHV3 germline gene sequence. The $V_H$ region of the M2e antibody is at least 80% homologous to the amino acid sequence of the $V_H$ region encoded by the IgHV4 or the IgHV3 $V_H$ germline gene sequence. Preferably, the amino acid sequence of $V_H$ region of the M2e antibody is at least 90%, 95%, 96%, 97% homologous to the amino acid sequence encoded by the IgHV4 or the IgHV3 germline gene sequence, and more preferably, at least 98%, 99% homologous to the sequence encoded by the IgHV4 or the IgHV3 germline gene sequence.

The M2e antibodies of the invention also include a variable light chain ($V_L$) region encoded by a human IgKV1 germline gene sequence. A human IgKV1 $V_L$ germline gene sequence is shown, e.g., Accession numbers X59315, X59312, X59318, J00248, and Y14865. Alternatively, the M2e antibodies include a $V_L$ region that is encoded by a nucleic acid sequence that is at least 80% homologous to the IgKV1 germline gene sequence. Preferably, the nucleic acid sequence is at least 90%, 95%, 96%, 97% homologous to the IgKV1 germline gene sequence, and more preferably, at least 98%, 99% homologous to the IgKV1 germline gene sequence. The $V_L$ region of the M2e antibody is at least 80% homologous to the amino acid sequence of the $V_L$ region encoded the IgKV1 germline gene sequence. Preferably, the amino acid sequence of $V_L$ region of the M2e antibody is at least 90%, 95%, 96%, 97% homologous to the amino acid sequence encoded by the IgKV1 germline gene sequence, and more preferably, at least 98%, 99% homologous to the sequence encoded by e the IgKV1 germline gene sequence.

In another aspect the invention provides a composition including an huM2e antibody according to the invention. In various aspects the composition further includes an anti-viral drug, a viral entry inhibitor or a viral attachment inhibitor. The anti-viral drug is for example a neuraminidase inhibitor, a HA inhibitor, a sialic acid inhibitor or an M2 ion channel inhibitor. The M2 ion channel inhibitor is for example amantadine or rimantadine. The neuraminidase inhibitor for example zanamivir, or oseltamivir phosphate. In a further aspect the composition further includes a second anti-influenza A antibody.

In a further aspect the huM2e antibodies according to the invention are operably-linked to a therapeutic agent or a detectable label.

Additionally, the invention provides methods for stimulating an immune response, treating, preventing or alleviating a symptom of an influenza viral infection by administering an huM2e antibody to a subject.

Optionally, the subject is further administered with a second agent such as, but not limited to, an influenza virus antibody, an anti-viral drug such as a neuraminidase inhibitor, a HA inhibitor, a sialic acid inhibitor or an M2 ion channel inhibitor, a viral entry inhibitor or a viral attachment inhibitor. The M2 ion channel inhibitor is for example amantadine or rimantadine. The neuraminidase inhibitor for example zanamivir, or oseltamivir phosphate. The subject is suffering from or is predisposed to developing an influenza virus infection, such as, for example, an autoimmune disease or an inflammatory disorder.

In another aspect, the invention provides methods of administering the huM2e antibody of the invention to a subject prior to, and/or after exposure to an influenza virus. For example, the huM2e antibody of the invention is used to treat or prevent rejection influenza infection. The huM2e antibody is administered at a dose sufficient to promote viral clearance or eliminate influenza A infected cells.

Also included in the invention is a method for determining the presence of an influenza virus infection in a patient, by contacting a biological sample obtained from the patient with a humM2e antibody; detecting an amount of the antibody that binds to the biological sample; and comparing the amount of antibody that binds to the biological sample to a control value.

The invention further provides a diagnostic kit comprising a huM2e antibody.

Other features and advantages of the invention will be apparent from and are encompassed by the following detailed description and claims.

BRIEF DESCRIPTION OF THE DRAWINGS

FIG. 6A is a chart showing cross reactivity binding of anti-M2 antibodies to variant M2 peptides (SEQ ID NOs 116-140, respectively).

FIG. 6B is a chart showing binding activity of M2 antibodies to truncated M2 peptides (SEQ ID NOs 116, 141-160, and 1, respectively).

FIG. 8 is an illustration showing the anti-M2 antibodies bind a highly conserved region in the N-Terminus of M2e.

FIG. 9 is a graph showing anti-M2 rHMAb clones from crude supernatant bound to influenza on ELISA, whereas the control anti-M2e mAb 14C2 did not readily bind virus.

FIG. 12 is an amino acid sequence alignment of the Kappa LC variable regions of three clones (SEQ ID NOs 161, 162, and 163, respectively).

FIG. 13 is an amino acid sequence alignment of the Gamma HC variable regions of three clones (SEQ ID NOs 164, 165, and 166, respectively).

DETAILED DESCRIPTION

Figure 1:
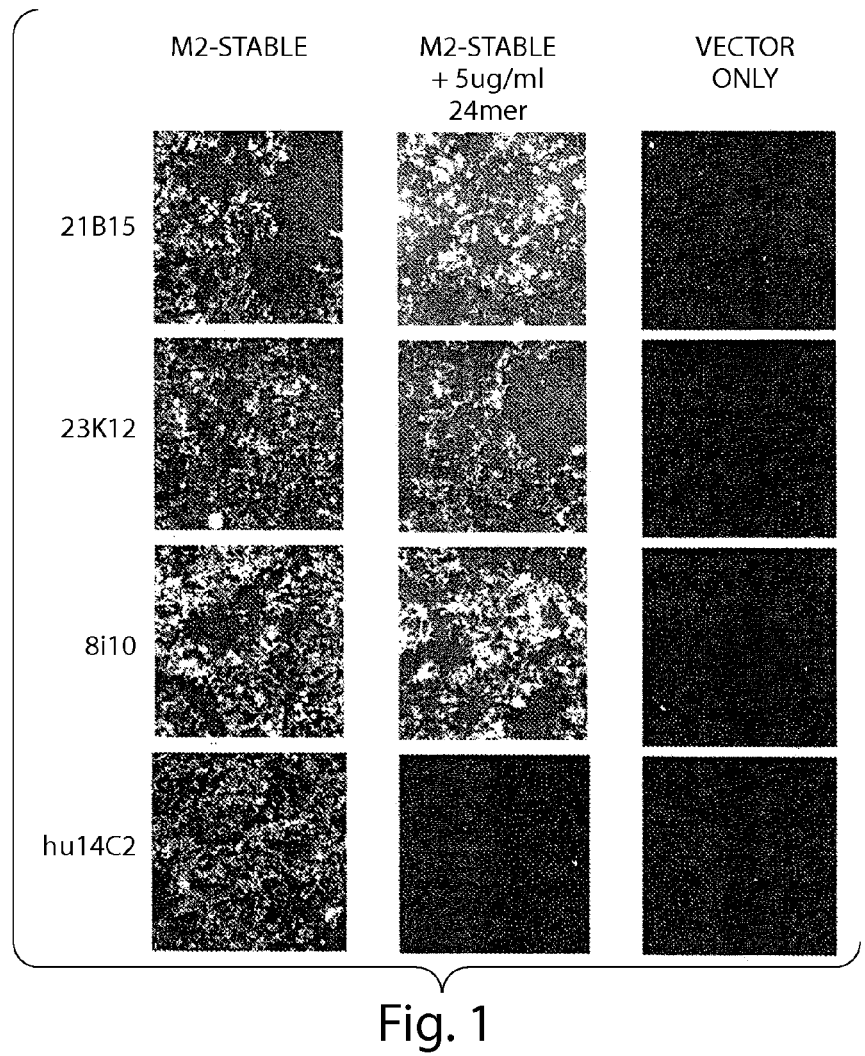
FIG. 1 shows the binding of three antibodies of the present invention and control hu14C2 antibody to 293-HEK cells transfected with an M2 expression construct or control vector, in the presence or absence of free M2 peptide.

The present invention provides fully human monoclonal antibodies specific against the extracellular domain of the matrix 2 (M2) polypeptide. The antibodies are respectively referred to herein is huM2e antibodies.

M2 is a 96 amino acid transmembrane protein present as a homotetramer on the surface of influenza virus and virally infected cells. M2 contains a 23 amino acid ectodomain (M2e) that is highly conserved across influenza A strains. Few amino acid changes have occurred since the 1918 pandemic strain thus M2e is an attractive target for influenza therapies. In prior studies, monoclonal antibodies specific to the M2 ectodomain (M2e) were derived upon immunizations with a peptide corresponding to the linear sequence of M2e. In contrast, the present invention provides a novel process whereby full-length M2 is expressed in cell lines, which allows for the identification of human antibodies that bound this cell-expressed M2e. The huM2e antibodies have been shown to bind conformational determinants on the M2-transfected cells, as well as native M2, either on influenza infected cells, or on the virus itself. The huM2e antibodies did not bind the linear M2e peptide, but they do bind several natural M2 variants, also expressed upon cDNA transfection into cell lines. Thus, this invention has allowed for the identification and production of human monoclonal antibodies that exhibit novel specificity for a very broad range of influenza A virus strains. These antibodies may be used diagnostically to identify influenza A infection and therapeutically to treat influenza A infection.

The huM2e antibodies of the invention have one or more of the following characteristics: the huM2e antibody binds a) to an epitope in the extracellular domain of the matrix 2 (M2) polypeptide of an influenza virus; b) binds to influenza A infected cells; and/or c) binds to influenza A virus (i.e., virons). The huM2e antibodies of the invention eliminate influenza infected cells through immune effector mechanisms such as ADCC and promotes direct viral clearance by binding to influenza virons. The huM2e antibodies of the invention bind to the amino-terminal region of the M2e polypeptide. Preferably, the huM2e antibodies of the invention bind to the amino-terminal region of the M2e polypeptide wherein the N-terminal methionine residue is absent. Exemplary M2e sequences include those sequences listed on Table I below

TABLE I

| Type | Name | Subtype | M2E Sequence | SEQ ID NO |
|---|---|---|---|---|
| A | BREVIG MISSION.1.1918 | H1N1 | MSLLTEVETPTRNEWGCRCNDSSD | SEQ ID NO: 1 |
| A | FORT MONMOUTH.1.1947 | H1N1 | MSLLTEVETPTKNEWECRCNDSSD | SEQ ID NO: 2 |
| A | .SINGAPORE.02.2005 | H3N2 | MSLLTEVETPIRNEWECRCNDSSD | SEQ ID NO: 3 |
| A | WISCONSIN.10.98 | H1N1 | MSLLTEVETPIRNGWECKCNDSSD | SEQ ID NO: 4 |
| A | WISCONSIN.301.1976 | H1N1 | MSLLTEVETPIRSEWGCRCNDSSD | SEQ ID NO: 5 |
| A | PANAMA.1.66 | H2N2 | MSFLPEVETPIRNEWGCRCNDSSD | SEQ ID NO: 6 |
| A | NEW YORK.321.1999 | H3N2 | MSLLTEVETPIRNEWGCRCNDSSN | SEQ ID NO: 7 |
| A | CARACAS.1.71 | H3N2 | MSLLTEVETPIRKEWGCRCNDSSD | SEQ ID NO: 8 |
| A | TAIWAN.3.71 | H3N2 | MSFLTEVETPIRNEWGCRCNDSSD | SEQ ID NO: 9 |
| A | WUHAN.359.95 | H3N2 | MSLPTEVETPIRSEWGCRCNDSSD | SEQ ID NO: 10 |
| A | HONG KONG.1144.99 | H3N2 | MSLLPEVETPIRNEWGCRCNDSSD | SEQ ID NO: 11 |
| A | HONG KONG.1180.99 | H3N2 | MSLLPEVETPIRNGWGCRCNDSSD | SEQ ID NO: 12 |
| A | HONG KONG.1774.99 | H3N2 | MSLLTEVETPTRNGWECRCSGSSD | SEQ ID NO: 13 |
| A | NEW YORK.217.02 | H1N2 | MSLLTEVETPIRNEWEYRCNDSSD | SEQ ID NO: 14 |
| A | NEW YORK.300.2003 | H1N2 | MSLLTEVETPIRNEWEYRCSDSSD | SEQ ID NO: 15 |
| A | SWINE.SPAIN.54008.2004 | H3N2 | MSLLTEVETPTRNGWECRYSDSSD | SEQ ID NO: 16 |
| A | GUANGZHOU.333.99 | H9N2 | MSFLTEVETLTRNGWECRCSDSSD | SEQ ID NO: 17 |
| A | HONG KONG.1073.99 | H9N2 | MSLLTEVETLTRNGWECKCRDSSD | SEQ ID NO: 18 |
| A | HONG KONG.1.68 | H3N2 | MSLLTEVETPIRNEWGCRCNDSSD | SEQ ID NO: 19 |
| A | SWINE.HONG KONG.126.1982 | H3N2 | MSLLTEVETPIRSEWGCRCNDSGD | SEQ ID NO: 20 |
| A | NEW YORK.703.1995 | H3N2 | MSLLTEVETPIRNEWECRCNGSSD | SEQ ID NO: 21 |
| A | SWINE.QUEBEC.192.81 | H1N1 | MSLPTEVETPIRNEWGCRCNDSSD | SEQ ID NO: 22 |
| A | PUERTO RICO.8.34 | H1N1 | MSLLTEVETPIRNEWGCRCNGSSD | SEQ ID NO: 23 |
| A | HONG KONG.485.97 | H5N1 | MSLLTEVDTLTRNGWGCRCSDSSD | SEQ ID NO: 24 |
| A | HONG KONG.542.97 | H5N1 | MSLLTEVETLTKNGWGCRCSDSSD | SEQ ID NO: 25 |

TABLE I-continued

| Type | Name | Subtype | M2E Sequence | SEQ ID NO |
|---|---|---|---|---|
| A | SILKY CHICKEN.SHANTOU.1826. 2004 | H9N2 | MSLLTEVETPTRNGWECKCSDSSD | SEQ ID NO: 26 |
| A | CHICKEN.TAIWAN.0305.04 | H6N1 | MSLLTEVETHTRNGWECKCSDSSD | SEQ ID NO: 27 |
| A | QUAIL.ARKANSAS.16309-7.94 | H7N3NSA | MSLLTEVKTPTRNGWECKCSDSSD | SEQ ID NO: 28 |
| A | HONG KONG.486.97 | H5N1 | MSLLTEVETLTRNGWGCRCSDSSD | SEQ ID NO: 29 |
| A | CHICKEN.PENNSYLVANIA. 13552-1.98 | H7N2NSB | MSLLTEVETPTRDGWECKCSDSSD | SEQ ID NO: 30 |
| A | CHICKEN.HEILONGJIANG. 48.01 | H9N2 | MSLLTEVETPTRNGWGCRCSDSSD | SEQ ID NO: 31 |
| A | SWINE.KOREA.S5.2005 | H1N2 | MSLLTEVETPTRNGWECKCNDSSD | SEQ ID NO: 32 |
| A | HONG KONG.1073.99 | H9N2 | MSLLTEVETLTRNGWECKCSDSSD | SEQ ID NO: 33 |
| A | WISCONSIN.3523.88 | H1N1 | MSLLTEVETPIRNEWGCKCNDSSD | SEQ ID NO: 34 |
| A | X-31 VACCINE STRAIN | H3N2 | MSFLTEVETPIRNEWGCRCNGSSD | SEQ ID NO: 35 |
| A | CHICKEN.ROSTOCK.8.1934 | H7N1 | MSLLTEVETPTRNGWECRCNDSSD | SEQ ID NO: 36 |
| A | ENVIRONMENT.NEW YORK.16326-1.2005 | H7N2 | MSLLTEVETPIRKGWECNCSDSSD | SEQ ID NO: 37 |
| A | INDONESIA.560H.2006 | H5N1 | MSLLTEVETPTRNEWECRCSDSSD | SEQ ID NO: 38 |
| A | CHICKEN.HONG KONG.SF1.03 | H9N2 | MSLLTGVETHTRNGWGCKCSDSSD | SEQ ID NO: 39 |
| A | CHICKEN.HONGKONG.YU4 27.03 | H9N2 | MSLLPEVETHTRNGWGCRCSDSSD | SEQ ID NO: 40 |

In one embodiment, the huM2e antibodies of the invention bind to a M2e that wholly or partially includes the amino acid residues from position 2 to position 7 of M2e when numbered in accordance with SEQ ID NO:1. For example, the huM2e antibodies of the invention bind wholly or partially to the amino acid sequence SLLTEVET (SEQ ID NO: 41) Most preferably, the huM2e antibodies of the invention bind wholly or partially to the amino acid sequence SLLTEV (SEQ ID NO: 42) Preferably, the huM2e antibodies of the invention bind to non-linear epitope of the M2e protein. For example, the huM2e antibodies bind to an epitope comprising position 2, 5, and 6 of the M2e polypeptide when numbered in accordance to SEQ ID NO: 1 where the amino acid at a) position 2 is a serine; b) position 5 is a threonine; and c) position 6 is a glutamic acid. Exemplary huM2e monoclonal antibodies that binds to this epitope are the 8I10, 21B15 or 23K12 antibodies described herein.

The 8I10 antibody includes a heavy chain variable region (SEQ ID NO: 44) encoded by the nucleic acid sequence shown below in SEQ ID NO: 43, and a light chain variable region (SEQ ID NO: 46) encoded by the nucleic acid sequence shown in SEQ ID NO: 45.

The amino acids encompassing the CDRs as defined by Chothia, C. et al. (1989, Nature, 342: 877-883) are underlined and those defined by Kabat E. A. et al. (1991, Sequences of Proteins of Immunological Interest, 5$^{th}$ edit., NIH Publication no. 91-3242 U.S. Department of Heath and Human Services) are highlighted in bold in the sequences below.

The heavy chain CDRs of the 8I10 antibody have the following sequences per Kabat definition: NYYWS (SEQ ID NO: 72), FIYYGGNTKYNPS LKS (SEQ ID NO: 74) and ASCSGGYCILD (SEQ ID NO: 76). The light chain CDRs of the 8I10 antibody have the following sequences per Kabat definition: RASQNIYKYLN (SEQ ID NO: 59), AA SGLQS (SEQ ID NO: 61) and QQSYSPPLT (SEQ ID NO: 63).

The heavy chain CDRs of the 8I10 antibody have the following sequences per Chothia definition: GSSISN (SEQ ID NO: 109), FIYYGGNTK (SEQ ID NO: 110) and ASCSGGYCILD (SEQ ID NO: 76). The light chain CDRs of the 8I10 antibody have the following sequences per Chothia definition: RASQNIYKYLN (SEQ ID NO: 59), AASGLQS (SEQ ID NO: 61) and QQSYSPPLT (SEQ ID NO: 63).

```
>8I10 VH nucleotide sequence:
                                     (SEQ ID NO: 43)
CAGGTGCAATTGCAGGAGTCGGGCCCAGGACTGGTGAAGCCTTCGGAGAC

CCTGTCCCTCACCTGCACTGTCTCTGGTTCGTCCATCAGTAATTACTACT

GGAGCTGGATCCGGCAGTCCCCAGGGAAGGGACTGGAGTGGATTGGGTTT

ATCTATTACGGTGGAAACACCAAGTACAATCCCTCCCTCAAGAGCCGCGT

CACCATATCACAAGACACTTCCAAGAGTCAGGTCTCCCTGACGATGAGCT

CTGTGACCGCTGCGGAATCGGCCGTCTATTTCTGTGCGAGAGCGTCTTGT

AGTGGTGGTTACTGTATCCTTGACTACTGGGGCCAGGGAACCCTGGTCAC

CGTCTCG

>8I10 VH amino acid sequence:
                                     (SEQ ID NO: 44)
Kabat Bold, Chothia underlined
Q V Q L Q E S G P G L V K P S E T L S L T
```

```
C T V S G S S I S N Y Y W S W I R Q S P G

K G L E W I G F I Y Y G G N T K Y N P S L

K S R V T I S Q D T S K S Q V S L T M S S

V T A A E S A V Y F C A R A S C S G G Y C

I L D Y W G Q G T L V T V S

>8I10 VL nucleotide sequence:
                                          (SEQ ID NO: 45)
GACATCCAGATGACCCAGTCTCCATCCTCCCTGTCTGCATCTGTAGGAGA

CAGAGTCACCATCACTTGCCGGGCGAGTCAGAACATTTACAAGTATTTAA

ATTGGTATCAGCAGAGACCAGGGAAAGCCCCTAAGGGCCTGATCTCTGCT

GCATCCGGGTTGCAAAGTGGGGTCCCATCAAGGTTCAGTGGCAGTGGATC

TGGGACAGATTTCACTCTCACCATCACCAGTCTGCAACCTGAAGATTTTG

CAACTTACTACTGTCAACAGAGTTACAGTCCCCCTCTCACTTTCGGCGGA

GGGACCAGGGTGGAGATCAAAC

>8I10 VL amino acid sequence:
                                          (SEQ ID NO: 46)
Kabat Bold, Chothia underlined
D I Q M T Q S P S S L S A S V G D R V T I

T C R A S Q N I Y K Y L N W Y Q Q R P G K

A P K G L I S A A S G L Q S G V P S R F S

G S G S G T D F T L T I T S L Q P E D F A

T Y Y C Q Q S Y S P P L T F G G G T R V E

I K
```

The 21B15 antibody includes antibody includes a heavy chain variable region (SEQ ID NO: 44) encoded by the nucleic acid sequence shown below in SEQ ID NO: 47, and a light chain variable region (SEQ ID NO: 46) encoded by the nucleic acid sequence shown in SEQ ID NO: 48.

The amino acids encompassing the CDRs as defined by Chothia et al. 1989, are underlined and those defined by Kabat et al., 1991 are highlighted in bold in the sequences below.

The heavy chain CDRs of the 21B15 antibody have the following sequences per Kabat definition: NYYWS (SEQ ID NO: 72), FIYYGGNTKYNPSLKS (SEQ ID NO: 74) and ASCSGGYCILD (SEQ ID NO: 76). The light chain CDRs of the 21B15 antibody have the following sequences per Kabat definition: RASQNIYKYLN (SEQ ID NO: 59), AASGLQS (SEQ ID NO: 61) and QQSYSPPLT (SEQ ID NO: 63).

The heavy chain CDRs of the 21B15 antibody have the following sequences per Chothia definition: GSSISN (SEQ ID NO: 109), FIYYGGNTK (SEQ ID NO: 110) and ASC-SGGYCILD (SEQ ID NO: 76).

```
>21B15 VH nucleotide sequence:
                                          (SEQ ID NO: 47)
CAGGTGCAATTGCAGGAGTCGGGCCCAGGACTGGTGAAGCCTTCGGAGAC

CCTGTCCCTCACCTGCACTGTCTCTGGTTCGTCCATCAGTAATTACTACT

GGAGCTGGATCCGGCAGTCCCCAGGGAAGGGACTGGAGTGGATTGGGTTT

ATCTATTACGGTGGAAACACCAAGTACAATCCCTCCCTCAAGAGCCGCGT

CACCATATCACAAGACACTTCCAAGAGTCAGGTCTCCCTGACGATGAGCT

CTGTGACCGCTGCGGAATCGGCCGTCTATTTCTGTGCGAGAGCGTCTTGT

AGTGGTGGTTACTGTATCCTTGACTACTGGGGCCAGGGAACCCTGGTCAC

CGTCTCG

>21B15 VH amino acid sequence:
                                          (SEQ ID NO: 44)
Kabat Bold, Chothia underlined
Q V Q L Q E S G P G L V K P S E T L S L T

C T V S G S S I S N Y Y W S W I R Q S P G

K G L E W I G F I Y Y G G N T K Y N P S L

K S R V T I S Q D T S K S Q V S L T M S S

V T A A E S A V Y F C A R A S C S G G Y C

I L D Y W G Q G T L V T V S

>21B15 VL nucleotide sequence:
                                          (SEQ ID NO: 48)
GACATCCAGGTGACCCAGTCTCCATCCTCCCTGTCTGCATCTGTAGGAGA

CAGAGTCACCATCACTTGCCGCGCGAGTCAGAACATTTACAAGTATTTAA

ATTGGTATCAGCAGAGACCAGGGAAAGCCCCTAAGGGCCTGATCTCTGCT

GCATCCGGGTTGCAAAGTGGGGTCCCATCAAGGTTCAGTGGCAGTGGATC

TGGGACAGATTTCACTCTCACCATCACCAGTCTGCAACCTGAAGATTTTG

CAACTTACTACTGTCAACAGAGTTACAGTCCCCCTCTCACTTTCGGCGGA

GGGACCAGGGTGGATATCAAAC

>21B15 VL amino acid sequence:
                                          (SEQ ID NO: 46)
Kabat Bold, Chothia underlined
D I Q V T Q S P S S L S A S V G D R V T I

T C R A S Q N I Y K Y L N W Y Q Q R P G K

A P K G L I S A A S G L Q S G V P S R F S

G S G S G T D F T L T I T S L Q P E D F A

T Y Y C Q Q S Y S P P L T F G G G T R V D

I K
```

The 23K12 antibody includes antibody includes a heavy chain variable region (SEQ ID NO: 50) encoded by the nucleic acid sequence shown below in SEQ ID NO: 49, and a light chain variable region (SEQ ID NO: 52) encoded by the nucleic acid sequence shown in SEQ ID NO: 51.

The amino acids encompassing the CDRs as defined by Chothia et al., 1989 are underlined and those defined by Kabat et al., 1991 are highlighted in bold in the sequences below.

The heavy chain CDRs of the 23K12 antibody have the following sequences per Kabat definition: SNYMS (SEQ ID NO: 103), VIYSGGSTYYADSVK (SEQ ID NO: 105) and CLSRMRGYGLDV (SEQ ID NO: 107). The light chain CDRs of the 23K12 antibody have the following sequences per Kabat definition: RTSQSISSYLN (SEQ ID NO: 92), AASSLQSGVPSRF (SEQ ID NO: 94) and QQSYSMPA (SEQ ID NO: 96).

The heavy chain CDRs of the 23K12 antibody have the following sequences per Chothia definition: GFTVSSN (SEQ ID NO: 112), VIYSGGSTY (SEQ ID NO: 113) and CLSRMRGYGLDV (SEQ ID NO: 107). The light chain CDRs of the 23K12 antibody have the following sequences per Chothia definition: RTSQSISSYLN (SEQ ID NO: 92), AASSLQSGVPSRF (SEQ ID NO: 94) and QQSYSMPA (SEQ ID NO: 96).

>23K12 VH nucleotide sequence:
(SEQ ID NO: 49)
GAGGTGCAGCTGGTGGAGTCTGGGGGAGGCTTGGTCCAGCCTGGGGGGTC

CCTGAGAATCTCCTGTGCAGCCTCTGGATTCACCGTCAGTAGCAACTACA

TGAGTTGGGTCCGCCAGGCTCCAGGGAAGGGGCTGGAGTGGGTCTCAGTT

ATTTATAGTGGTGGTAGCACATACTACGCAGACTCCGTGAAGGGCAGATT

CTCCTTCTCCAGAGACAACTCCAAGAACACAGTGTTTCTTCAAATGAACA

GCCTGAGAGCCGAGGACACGGCTGTGTATTACTGTGCGAGATGTCTGAGC

AGGATGCGGGGTTACGGTTTAGACGTCTGGGGCCAAGGGACCACGGTCAC

CGTCTCG

>23K12 VH amino acid sequence:
(SEQ ID NO: 50)
Kabat Bold, Chothia underlined
E V Q L V E S G G G L V Q P G G S L R I S C A A S G F T V S <u>S N Y M S</u> W V R Q A P G K G L E W V S <u>V I Y S G G S T Y</u> Y A D S V

K G R F S F S R D N S K N T V F L Q M N S

L R A E D T A V Y Y C A R <u>C L S R M R G Y</u>

<u>G L D V</u> W G Q G T T V T V S

>23K12 VL nucleotide sequence:
(SEQ ID NO: 51)
GACATCCAGATGACCCAGTCTCCATCCTCCCTGTCTGCATCTGTAGGAGA

CAGAGTCACCATCACTTGCCGGACAAGTCAGAGCATTAGCAGCTATTTAA

ATTGGTATCAGCAGAAACCAGGGAAAGCCCCTAAACTCCTGATCTATGCT

GCATCCAGTTTGCAAAGTGGGGTCCCATCAAGGTTCAGTGGCAGTGGATC

TGGGACAGATTTCACTCTCACCATCAGCGGTCTGCAACCTGAAGATTTTG

CAACCTACTACTGTCAACAGAGTTACAGTATGCCTGCCTTTGGCCAGGGG

ACCAAGCTGGAGATCAAA

>23K12 VL amino acid sequence:
(SEQ ID NO: 52)
Kabat Bold, Chothia underlined
D I Q M T Q S P S S L S A S V G D R V T I T C <u>R T S Q S I S S Y L N</u> W Y Q Q K P G K A P K L L I Y <u>A A S S L Q S G V P S R F</u> S

G S G S G T D F T L T I S G L Q P E D F A

T Y Y C <u>Q Q S Y S M P A</u> F G Q G T K L E I

K

HuM2e antibodies of the invention also include antibodies that include a heavy chain variable amino acid sequence that is at least 90%, 92%, 95%, 97% 98%, 99% or more identical the amino acid sequence of SEQ ID NO: 44 or 49. and/or a light chain variable amino acid that is at least 90%, 92%, 95%, 97% 98%, 99% or more identical the amino acid sequence of SEQ ID NO: 46 or 52.

Alternatively, the monoclonal antibody is an antibody that binds to the same epitope as 8I10, 21B15 or 23K12.

The heavy chain of a M2e antibody is derived from a germ line V (variable) gene such as, for example, the IgHV4 or the IgHV3 germline gene.

The M2e antibodies of the invention include a variable heavy chain ($V_H$) region encoded by a human IgHV4 or the IgHV3 germline gene sequence. A IgHV4 germline gene sequence are shown, e.g., in Accession numbers L10088, M29812, M95114, X56360 and M95117. IgHV3 germline gene sequence are shown, e.g., in Accession numbers X92218, X70208, Z27504, M99679 and AB019437. The M2e antibodies of the invention include a $V_H$ region that is encoded by a nucleic acid sequence that is at least 80% homologous to the IgHV4 or the IgHV3 germline gene sequence. Preferably, the nucleic acid sequence is at least 90%, 95%, 96%, 97% homologous to the IgHV4 or the IgHV3 germline gene sequence, and more preferably, at least 98%, 99% homologous to the IgHV4 or the IgHV3 germline gene sequence. The $V_H$ region of the M2e antibody is at least 80% homologous to the amino acid sequence of the $V_H$ region encoded by the IgHV4 or the IgHV3 $V_H$ germline gene sequence. Preferably, the amino acid sequence of $V_H$ region of the M2e antibody is at least 90%, 95%, 96%, 97% homologous to the amino acid sequence encoded by the IgHV4 or the IgHV3 germline gene sequence, and more preferably, at least 98%, 99% homologous to the sequence encoded by the IgHV4 or the IgHV3 germline gene sequence.

The M2e antibodies of the invention also include a variable light chain ($V_L$) region encoded by a human IgKV1 germline gene sequence. A human IgKV1 $V_L$ germline gene sequence is shown, e.g., Accession numbers X59315, X59312, X59318, J00248, and Y14865. Alternatively, the M2e antibodies include a $V_L$ region that is encoded by a nucleic acid sequence that is at least 80% homologous to the IgKV1 germline gene sequence. Preferably, the nucleic acid sequence is at least 90%, 95%, 96%, 97% homologous to the IgKV1 germline gene sequence, and more preferably, at least 98%, 99% homologous to the IgKV1 germline gene sequence. The $V_L$ region of the M2e antibody is at least 80% homologous to the amino acid sequence of the $V_L$ region encoded the IgKV1 germline gene sequence. Preferably, the amino acid sequence of $V_L$ region of the M2e antibody is at least 90%, 95%, 96%, 97% homologous to the amino acid sequence encoded by the IgKV1 germline gene sequence, and more preferably, at least 98%, 99% homologous to the sequence encoded by e the IgKV1 germline gene sequence.

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984).

The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

The following definitions are useful in understanding the present invention:

The term "antibody" (Ab) as used herein includes monoclonal antibodies, polyclonal antibodies, multispecific antibodies (e.g., bispecific antibodies), and antibody fragments, so long as they exhibit the desired biological activity. The term "immunoglobulin" (Ig) is used interchangeably with "antibody" herein.

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody is purified: (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic four-chain antibody unit is a heterotetrameric glycoprotein composed of two identical light (L) chains and two identical heavy (H) chains. An IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for µ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71, and Chapter 6.

The L chain from any vertebrate species can be assigned to one of two clearly distinct types, called kappa (κ) and lambda (λ), based on the amino acid sequences of their constant domains ($C_L$). Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated alpha (α), delta (δ), epsilon (ε), gamma (γ) and mu (µ), respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the V domains differ extensively in sequence among antibodies. The V domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the n-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35 (H1), 50-65 (H2) and 95-102 (H3) in the $V_H$ when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the $V_L$, and 26-32 (H1), 52-56 (H2) and 95-101 (H3) in the $V_H$ when numbered in accordance with the Chothia numbering system; Chothia and Lesk, J. Mol. Biol. 196:901-917 (1987)); and/or those residues from a "hypervariable loop"/CDR (e.g., residues 27-38 (L1), 56-65 (L2) and 105-120 (L3) in the $V_L$, and 27-38 (H1), 56-65 (H2) and 105-120 (H3) in the $V_H$ when numbered in accordance with the IMGT numbering system; Lefranc, M. P. et al. Nucl. Acids Res. 27:209-212 (1999), Ruiz, M. e al. Nucl. Acids Res. 28:219-221 (2000)). Optionally the antibody has symmetrical insertions at one or more of the following points 28, 36 (L1), 63, 74-75 (L2) and 123 (L3) in the $V_L$, and 28, 36 (H1), 63, 74-75 (H2) and 123 (H3) in the $V_H$ when numbered in accordance with AHo; Honneger, A. and Plunkthun, A. J. Mol. Biol. 309:657-670 (2001)).

By "germline nucleic acid residue" is meant the nucleic acid residue that naturally occurs in a germline gene encoding a constant or variable region. "Germline gene" is the DNA found in a germ cell (i.e., a cell destined to become an egg or in the sperm). A "germline mutation" refers to a heritable change in a particular DNA that has occurred in a germ cell or the zygote at the single-cell stage, and when transmitted to offspring, such a mutation is incorporated in every cell of the body. A germline mutation is in contrast to a somatic mutation which is acquired in a single body cell. In some cases, nucleotides in a germline DNA sequence encoding for a variable region are mutated (i.e., a somatic mutation) and replaced with a different nucleotide.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). The present invention provides variable domain antigen-binding sequences derived from human antibodies. Accordingly, chimeric antibodies of primary interest herein include antibodies having one or more human antigen binding sequences (e.g., CDRs) and containing one or more sequences derived from a non-human antibody, e.g., an FR or C region sequence. In addition, chimeric antibodies of primary interest herein include those comprising a human variable domain antigen binding sequence of one antibody class or subclass and another sequence, e.g., FR or C region sequence, derived from another antibody class or subclass. Chimeric antibodies of interest herein also include those containing variable domain antigen-binding sequences related to those described herein or derived from a different species, such as a non-human primate (e.g., Old World Monkey, Ape, etc). Chimeric antibodies also include primatized and humanized antibodies.

Furthermore, chimeric antibodies may comprise residues that are not found in the recipient antibody or in the donor antibody. These modifications are made to further refine antibody performance. For further details, see Jones et al., Nature 321:522-525 (1986); Riechmann et al., Nature 332:323-329 (1988); and Presta, Curr. Op. Struct. Biol. 2:593-596 (1992).

A "humanized antibody" is generally considered to be a human antibody that has one or more amino acid residues introduced into it from a source that is non-human. These non-human amino acid residues are often referred to as "import" residues, which are typically taken from an "import" variable domain. Humanization is traditionally performed following the method of Winter and co-workers (Jones et al., Nature, 321:522-525 (1986); Reichmann et al., Nature, 332:323-327 (1988); Verhoeyen et al., Science, 239: 1534-1536 (1988)), by substituting import hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species.

A "human antibody" is an antibody containing only sequences present in an antibody naturally produced by a human. However, as used herein, human antibodies may comprise residues or modifications not found in a naturally occurring human antibody, including those modifications and variant sequences described herein. These are typically made to further refine or enhance antibody performance.

An "intact" antibody is one that comprises an antigen-binding site as well as a $C_L$ and at least heavy chain constant domains, $C_H1$, $C_H2$ and $C_H3$. The constant domains may be native sequence constant domains (e.g., human native sequence constant domains) or amino acid sequence variant thereof. Preferably, the intact antibody has one or more effector functions.

An "antibody fragment" comprises a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870; Zapata et al., Protein Eng. 8(10): 1057-1062 [1995]); single-chain antibody molecules; and multispecific antibodies formed from antibody fragments.

The phrase "functional fragment or analog" of an antibody is a compound having qualitative biological activity in common with a full-length antibody. For example, a functional fragment or analog of an anti-IgE antibody is one that can bind to an IgE immunoglobulin in such a manner so as to prevent or substantially reduce the ability of such molecule from having the ability to bind to the high affinity receptor, Fc$_\epsilon$RI.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment that roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments that have hinge cysteines between them. Other chemical couplings of antibody fragments are also known.

The "Fc" fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment that contains a complete antigen-recognition and -binding site. This fragment consists of a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains that enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

As used herein, an antibody that "internalizes" is one that is taken up by (i.e., enters) the cell upon binding to an antigen on a mammalian cell (e.g., a cell surface polypeptide or receptor). The internalizing antibody will of course include antibody fragments, human or chimeric antibody, and antibody conjugates. For certain therapeutic applications, internalization in vivo is contemplated. The number of antibody molecules internalized will be sufficient or adequate to kill a cell or inhibit its growth, especially an infected cell. Depending on the potency of the antibody or antibody conjugate, in some instances, the uptake of a single antibody molecule into the cell is sufficient to kill the target cell to which the antibody binds. For example, certain toxins are highly potent in killing such that internalization of one molecule of the toxin conjugated to the antibody is sufficient to kill the infected cell.

As used herein, an antibody is said to be "immunospecific," "specific for" or to "specifically bind" an antigen if it reacts at a detectable level with the antigen, preferably with an affinity constant, $K_a$, of greater than or equal to about $10^4$ $M^{-1}$, or greater than or equal to about $10^5$ $M^{-1}$, greater than or equal to about $10^6$ $M^{-1}$, greater than or equal to about $10^7$ $M^{-1}$, or greater than or equal to $10^8$ $M^{-1}$. Affinity of an antibody for its cognate antigen is also commonly expressed as a dissociation constant $K_D$, and in certain embodiments, HuM2e antibody specifically binds to M2e if it binds with a $K_D$ of less than or equal to $10^{-4}$ M, less than or equal to about $10^{-5}$ M, less than or equal to about $10^{-6}$ M, less than or equal to $10^{-7}$ M, or less than or equal to $10^{-8}$ M. Affinities of antibodies can be readily determined using conventional techniques, for example, those described by Scatchard et al. (*Ann. N.Y. Acad. Sci. USA* 51:660 (1949)).

Binding properties of an antibody to antigens, cells or tissues thereof may generally be determined and assessed using immunodetection methods including, for example, immunofluorescence-based assays, such as immuno-histochemistry (IHC) and/or fluorescence-activated cell sorting (FACS).

An antibody having a "biological characteristic" of a designated antibody is one that possesses one or more of the biological characteristics of that antibody which distinguish it from other antibodies. For example, in certain embodiments, an antibody with a biological characteristic of a designated antibody will bind the same epitope as that bound by the designated antibody and/or have a common effector function as the designated antibody.

The term "antagonist" antibody is used in the broadest sense, and includes an antibody that partially or fully blocks, inhibits, or neutralizes a biological activity of an epitope, polypeptide, or cell that it specifically binds. Methods for identifying antagonist antibodies may comprise contacting a polypeptide or cell specifically bound by a candidate antagonist antibody with the candidate antagonist antibody and measuring a detectable change in one or more biological activities normally associated with the polypeptide or cell.

An "antibody that inhibits the growth of infected cells" or a "growth inhibitory" antibody is one that binds to and results in measurable growth inhibition of infected cells expressing or capable of expressing an M2e epitope bound by an antibody. Preferred growth inhibitory antibodies inhibit growth of infected cells by greater than 20%, preferably from about 20% to about 50%, and even more preferably, by greater than 50% (e.g., from about 50% to about 100%) as compared to the appropriate control, the control typically being infected cells not treated with the antibody being tested. Growth inhibition can be measured at an antibody concentration of about 0.1 to 30 µg/ml or about 0.5 nM to 200 nM in cell culture, where the growth inhibition is determined 1-10 days after exposure of the infected cells to the antibody. Growth inhibition of infected cells in vivo can be determined in various ways known in the art. The antibody is growth inhibitory in vivo if administration of the antibody at about 1 µg/kg to about 100 mg/kg body weight results in reduction the percent of infected cells or total number of infected cells within about 5 days to 3 months from the first administration of the antibody, preferably within about 5 to 30 days.

An antibody that "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). Preferably the cell is an infected cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody that induces apoptosis is one that results in about 2 to 50 fold, preferably about 5 to 50 fold, and most preferably about 10 to 50 fold, induction of annexin binding relative to untreated cell in an annexin binding assay.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC);

phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound to Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or U.S. Pat. No. 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al., PNAS (USA) 95:652-656 (1998).

"Fc receptor" or "FcR" describes a receptor that binds to the Fc region of an antibody. In certain embodiments, the FcR is a native sequence human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FCγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daeron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)).

"Human effector cells" are leukocytes that express one or more FcRs and perform effector functions. Preferably, the cells express at least FcγRIII and perform ADCC effector function. Examples of human leukocytes that mediate ADCC include PBMC, NK cells, monocytes, cytotoxic T cells and neutrophils; with PBMCs and NK cells being preferred. The effector cells may be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) that are bound to their cognate antigen. To assess complement activation, a CDC assay, e.g., as described in Gazzano-Santoro et al., J. Immunol. Methods 202:163 (1996), may be performed.

The terms "influenza A" and "Influenzavirus A" refer to a genus of the Orthomyxoviridae family of viruses. Influenzavirus A includes only one species: influenza A virus which cause influenza in birds, humans, pigs, and horses. Strains of all subtypes of influenza A virus have been isolated from wild birds, although disease is uncommon. Some isolates of influenza A virus cause severe disease both in domestic poultry and, rarely, in humans.

A "mammal" for purposes of treating n infection, refers to any mammal, including humans, domestic and farm animals, and zoo, sports, or pet animals, such as dogs, cats, cattle, horses, sheep, pigs, goats, rabbits, etc. Preferably, the mammal is human.

"Treating" or "treatment" or "alleviation" refers to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for an infection if, after receiving a therapeutic amount of an antibody according to the methods of the present invention, the patient shows observable and/or measurable reduction in or absence of one or more of the following: reduction in the number of infected cells or absence of the infected cells; reduction in the percent of total cells that are infected; and/or relief to some extent, one or more of the symptoms associated with the specific infection; reduced morbidity and mortality, and improvement in quality of life issues. The above parameters for assessing successful treatment and improvement in the disease are readily measurable by routine procedures familiar to a physician.

The term "therapeutically effective amount" refers to an amount of an antibody or a drug effective to "treat" a disease or disorder in a subject or mammal. See preceding definition of "treating."

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

Administration "in combination with" one or more further therapeutic agents includes simultaneous (concurrent) and consecutive administration in any order.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ polyethylene glycol (PEG), and PLURONICS™.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below.

A "growth inhibitory agent" when used herein refers to a compound or composition which inhibits growth of a cell, either in vitro or in vivo. Examples of growth inhibitory agents include agents that block cell cycle progression, such as agents that induce G1 arrest and M-phase arrest. Classical M-phase blockers include the vinca alkaloids (vincristine, vinorelbine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (W B Saunders: Philadelphia, 1995), especially p. 13. The taxanes (paclitaxel and docetaxel) are anticancer drugs both derived from the yew tree. Docetaxel (TAXOTERE™, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Label" as used herein refers to a detectable compound or composition that is conjugated directly or indirectly to the antibody so as to generate a "labeled" antibody. The label may be detectable by itself (e.g., radioisotope labels or fluorescent labels) or, in the case of an enzymatic label, may catalyze chemical alteration of a substrate compound or composition that is detectable.

The term "epitope tagged" as used herein refers to a chimeric polypeptide comprising a polypeptide fused to a "tag polypeptide." The tag polypeptide has enough residues to provide an epitope against which an antibody can be made, yet is short enough such that it does not interfere with activity of the polypeptide to which it is fused. The tag polypeptide is also preferably fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

A "small molecule" is defined herein to have a molecular weight below about 500 Daltons.

The terms "nucleic acid" and "polynucleotide" are used interchangeably herein to refer to single- or double-stranded RNA, DNA, or mixed polymers. Polynucleotides may include genomic sequences, extra-genomic and plasmid sequences, and smaller engineered gene segments that express, or may be adapted to express polypeptides.

An "isolated nucleic acid" is a nucleic acid that is substantially separated from other genome DNA sequences as well as proteins or complexes such as ribosomes and polymerases, which naturally accompany a native sequence. The term embraces a nucleic acid sequence that has been removed from its naturally occurring environment, and includes recombinant or cloned DNA isolates and chemically synthesized analogues or analogues biologically synthesized by heterologous systems. A substantially pure nucleic acid includes isolated forms of the nucleic acid. Of course, this refers to the nucleic acid as originally isolated and does not exclude genes or sequences later added to the isolated nucleic acid by the hand of man.

The term "polypeptide" is used in its conventional meaning, i.e., as a sequence of amino acids. The polypeptides are not limited to a specific length of the product. Peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Particular polypeptides of interest in the context of this invention are amino acid subsequences comprising CDRs and being capable of binding an antigen or Influenza A-infected cell.

An "isolated polypeptide" is one that has been identified and separated and/or recovered from a component of its natural environment. In preferred embodiments, the isolated polypeptide will be purified (1) to greater than 95% by weight of polypeptide as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated polypeptide includes the polypeptide in situ within recombinant cells since at least one component of the polypeptide's natural environment will not be present. Ordinarily, however, isolated polypeptide will be prepared by at least one purification step.

A "native sequence" polynucleotide is one that has the same nucleotide sequence as a polynucleotide derived from nature. A "native sequence" polypeptide is one that has the same amino acid sequence as a polypeptide (e.g., antibody) derived from nature (e.g., from any species). Such native sequence polynucleotides and polypeptides can be isolated from nature or can be produced by recombinant or synthetic means.

A polynucleotide "variant," as the term is used herein, is a polynucleotide that typically differs from a polynucleotide specifically disclosed herein in one or more substitutions, deletions, additions and/or insertions. Such variants may be naturally occurring or may be synthetically generated, for example, by modifying one or more of the polynucleotide sequences of the invention and evaluating one or more biological activities of the encoded polypeptide as described herein and/or using any of a number of techniques well known in the art.

A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention and evaluating one or more biological activities of the polypeptide as described herein and/or using any of a number of techniques well known in the art.

Modifications may be made in the structure of the polynucleotides and polypeptides of the present invention and still obtain a functional molecule that encodes a variant or derivative polypeptide with desirable characteristics. When it is desired to alter the amino acid sequence of a polypeptide to create an equivalent, or even an improved, variant or portion of a polypeptide of the invention, one skilled in the art will typically change one or more of the codons of the encoding DNA sequence.

For example, certain amino acids may be substituted for other amino acids in a protein structure without appreciable loss of its ability to bind other polypeptides (e.g., antigens) or cells. Since it is the binding capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences that encode said peptides without appreciable loss of their biological utility or activity.

In many instances, a polypeptide variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

Polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 *Methods in Enzymology* vol. 183, Academic Press, Inc., San Diego, Calif.; Higgins, D. G. and Sharp, P. M. (1989) *CABIOS* 5:151-153; Myers, E. W. and Muller W. (1988)

CABIOS 4:11-17; Robinson, E. D. (1971) *Comb. Theor* 11:105; Santou, N. Nes, M. (1987) *Mol. Biol. Evol.* 4:406-425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726-730.

Alternatively, optimal alignment of sequences for comparison may be conducted by the local identity algorithm of Smith and Waterman (1981) *Add APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) *J. Mol. Biol.* 215:403-410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information.

In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) *Proc. Natl. Acad. Sci. USA* 89:10915) alignments, (B) of 50, expectation (E) of 10, M=5, N=−4 and a comparison of both strands.

For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one approach, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

"Homology" refers to the percentage of residues in the polynucleotide or polypeptide sequence variant that are identical to the non-variant sequence after aligning the sequences and introducing gaps, if necessary, to achieve the maximum percent homology. In particular embodiments, polynucleotide and polypeptide variants have at least 70%, at least 75%, at least 80%, at least 90%, at least 95%, at least 98%, or at least 99% polynucleotide or polypeptide homology with a polynucleotide or polypeptide described herein.

"Vector" includes shuttle and expression vectors. Typically, the plasmid construct will also include an origin of replication (e.g., the ColE1 origin of replication) and a selectable marker (e.g., ampicillin or tetracycline resistance), for replication and selection, respectively, of the plasmids in bacteria. An "expression vector" refers to a vector that contains the necessary control sequences or regulatory elements for expression of the antibodies including antibody fragment of the invention, in bacterial or eukaryotic cells. Suitable vectors are disclosed below.

As used in this specification and the appended claims, the singular forms "a," "an" and "the" include plural references unless the content clearly dictates otherwise.

The present invention includes HuM2e antibodies comprising a polypeptide of the present invention, including those polypeptides encoded by a polynucleotide sequence set forth in Example 1 and amino acid sequences set forth in Example 1 and 2, and fragments and variants thereof. In one embodiment, the antibody is an antibody designated herein as 8i10, 21B15, or 23K12. These antibodies preferentially bind to or specifically bind to influenza A infected cells as compared to uninfected control cells of the same cell type.

In particular embodiments, the antibodies of the present invention bind to the M2 protein. In certain embodiments, the present invention provides HuM2e antibodies that bind to epitopes within M2e that are only present in the native conformation, i.e., as expressed in cells. In particular embodiments, these antibodies fail to specifically bind to an isolated M2e polypeptide, e.g., the 23 amino acid residue M2e fragment. It is dunderstood that these antibodies recognize non-linear (i.e. conformational) epitope(s) of the M2 peptide.

These specific conformational epitopes within the M2 protein, and particularly within M2e, may be used as vaccines to prevent the development of influenza infection within a subject.

As will be understood by the skilled artisan, general description of antibodies herein and methods of preparing and using the same also apply to individual antibody polypeptide constituents and antibody fragments.

The antibodies of the present invention may be polyclonal or monoclonal antibodies. However, in preferred embodiments, they are monoclonal. In particular embodiments, antibodies of the present invention are fully human antibodies. Methods of producing polyclonal and monoclonal antibodies are known in the art and described generally, e.g., in U.S. Pat. No. 6,824,780. Typically, the antibodies of the present invention are produced recombinantly, using vectors and methods available in the art, as described further below. Human antibodies may also be generated by in vitro activated B cells (see U.S. Pat. Nos. 5,567,610 and 5,229,275).

Human antibodies may also be produced in transgenic animals (e.g., mice) that are capable of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice results in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806, 5,569,825, 5,591,669 (all of GenPharm); U.S. Pat. No. 5,545,807; and WO 97/17852. Such animals may be genetically engineered to produce human antibodies comprising a polypeptide of the present invention.

In certain embodiments, antibodies of the present invention are chimeric antibodies that comprise sequences derived from both human and non-human sources. In particular embodiments, these chimeric antibodies are humanized or Primatized™. In practice, humanized antibodies are typically human antibodies in which some hypervariable region residues and possibly some FR residues are substituted by residues from analogous sites in rodent antibodies.

In the context of the present invention, chimeric antibodies also include fully human antibodies wherein the human hypervariable region or one or more CDRs are retained, but one or more other regions of sequence have been replaced by corresponding sequences from a non-human animal.

The choice of non-human sequences, both light and heavy, to be used in making the chimeric antibodies is important to reduce antigenicity and human anti-non-human antibody responses when the antibody is intended for human therapeutic use. It is further important that chimeric antibodies retain high binding affinity for the antigen and other favorable biological properties. To achieve this goal, according to a preferred method, chimeric antibodies are prepared by a process of analysis of the parental sequences and various conceptual chimeric products using three-dimensional models of the parental human and non-human sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

As noted above, antibodies (or immunoglobulins) can be divided into five different classes, based on differences in the amino acid sequences in the constant region of the heavy chains. All immunoglobulins within a given class have very similar heavy chain constant regions. These differences can be detected by sequence studies or more commonly by serological means (i.e. by the use of antibodies directed to these differences). Antibodies, or fragments thereof, of the present invention may be any class, and may, therefore, have a gamma, mu, alpha, delta, or epsilon heavy chain. A gamma chain may be gamma 1, gamma 2, gamma 3, or gamma 4; and an alpha chain may be alpha 1 or alpha 2.

In a preferred embodiment, an antibody of the present invention, or fragment thereof, is an IgG. IgG is considered the most versatile immunoglobulin, because it is capable of carrying out all of the functions of immunoglobulin molecules. IgG is the major Ig in serum, and the only class of Ig that crosses the placenta. IgG also fixes complement, although the IgG4 subclass does not. Macrophages, monocytes, PMN's and some lymphocytes have Fc receptors for the Fc region of IgG. Not all subclasses bind equally well; IgG2 and IgG4 do not bind to Fc receptors. A consequence of binding to the Fc receptors on PMN's, monocytes and macrophages is that the cell can now internalize the antigen better. IgG is an opsonin that enhances phagocytosis. Binding of IgG to Fc receptors on other types of cells results in the activation of other functions. Antibodies of the present invention may be of any IgG subclass.

In another preferred embodiment, an antibody, or fragment thereof, of the present invention is an IgE. IgE is the least common serum Ig since it binds very tightly to Fc receptors on basophils and mast cells even before interacting with antigen. As a consequence of its binding to basophils an mast cells, IgE is involved in allergic reactions. Binding of the allergen to the IgE on the cells results in the release of various pharmacological mediators that result in allergic symptoms. IgE also plays a role in parasitic helminth diseases. Eosinophils have Fc receptors for IgE and binding of eosinophils to IgE-coated helminths results in killing of the parasite. IgE does not fix complement.

In various embodiments, antibodies of the present invention, and fragments thereof, comprise a variable light chain that is either kappa or lambda. The lamba chain may be any of subtype, including, e.g., lambda 1, lambda 2, lambda 3, and lambda 4.

As noted above, the present invention further provides antibody fragments comprising a polypeptide of the present invention. In certain circumstances there are advantages of using antibody fragments, rather than whole antibodies. For example, the smaller size of the fragments allows for rapid clearance, and may lead to improved access to certain tissues, such as solid tumors. Examples of antibody fragments include: Fab, Fab', F(ab')$_2$ and Fv fragments; diabodies; linear antibodies; single-chain antibodies; and multispecific antibodies formed from antibody fragments.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Fab'-SH fragments can be directly recovered from *E. coli* and chemically coupled to form F(ab')$_2$ fragments (Carter et al., Bio/Technology 10:163-167 (1992)). According to another approach, F(ab')$_2$ fragments can be isolated directly from recombinant host cell culture. Fab and F(ab')$_2$ fragment with increased in vivo half-life comprising a salvage receptor binding epitope residues are described in U.S. Pat. No. 5,869,046. Other techniques for the production of antibody fragments will be apparent to the skilled practitioner.

In other embodiments, the antibody of choice is a single chain Fv fragment (scFv). See WO 93/16185; U.S. Pat. Nos. 5,571,894; and 5,587,458. Fv and sFv are the only species with intact combining sites that are devoid of constant regions. Thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870 for example. Such linear antibody fragments may be monospecific or bispecific.

In certain embodiments, antibodies of the present invention are bispecific or multi-specific. Bispecific antibodies are antibodies that have binding specificities for at least two different epitopes. Exemplary bispecific antibodies may bind to two different epitopes of a single antigen. Other such antibodies may combine a first antigen binding site with a binding site for a second antigen. Alternatively, an anti-M2e arm may be combined with an arm that binds to a triggering molecule on a leukocyte, such as a T-cell receptor molecule (e.g., CD3), or Fc receptors for IgG (FcγR), such as FcγRI (CD64), FcγRII (CD32) and FcγRIII (CD16), so as to focus and localize cellular defense mechanisms to the infected cell. Bispecific antibodies may also be used to localize cytotoxic agents to infected cells. These antibodies possess an M2e-binding arm and an arm that binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., F(ab')$_2$ bispecific antibodies). WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of ten different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655-3659 (1991).

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach described in U.S. Pat. No. 5,731,168, the interface between a pair of antibody molecules can be engineered to maximize the percentage of heterodimers that are recovered from recombinant cell culture. The preferred interface comprises at least a part of the $C_H3$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')$_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., J. Exp. Med., 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a $V_H$ connected to a $V_L$ by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

Antibodies with more than two valencies are contemplated. For example, trispecific antibodies can be prepared. Tutt et al., J. Immunol. 147: 60 (1991). A multivalent antibody may be internalized (and/or catabolized) faster than a bivalent antibody by a cell expressing an antigen to which the antibodies bind. The antibodies of the present invention can be multivalent antibodies with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a $C_L$ domain.

Antibodies of the present invention further include single chain antibodies.

In particular embodiments, antibodies of the present invention are internalizing antibodies.

Amino acid sequence modification(s) of the antibodies described herein are contemplated. For example, it may be desirable to improve the binding affinity and/or other biological properties of the antibody. Amino acid sequence variants of the antibody may be prepared by introducing appropriate nucleotide changes into a polynucleotide that encodes the antibody, or a chain thereof, or by peptide synthesis. Such modifications include, for example, deletions from, and/or insertions into and/or substitutions of, residues within the amino acid sequences of the antibody. Any combination of deletion, insertion, and substitution may be made to arrive at the final antibody, provided that the final construct possesses the desired characteristics. The amino acid changes also may alter post-translational processes of the antibody, such as changing the number or position of glycosylation sites. Any of the variations and modifications described above for polypeptides of the present invention may be included in antibodies of the present invention.

A useful method for identification of certain residues or regions of an antibody that are preferred locations for mutagenesis is called "alanine scanning mutagenesis" as described by Cunningham and Wells in Science, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with PSCA antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed anti-antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of an antibody include the fusion to the N- or C-terminus of the antibody to an enzyme (e.g., for ADEPT) or a polypeptide that increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative and non-conservative substitutions are contemplated.

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

One type of substitutional variant involves substituting one or more hypervariable region residues of a parent antibody. Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and an antigen or infected cell. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceyl-galactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The antibody of the invention is modified with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176: 1191-1195 (1992) and Shopes, B. J. Immunol. 148:2918-2922 (1992). Homodimeric antibodies with enhanced anti-infection activity may also be prepared using heterobifunctional cross-linkers as described in Wolff et al., Cancer Research 53:2560-2565 (1993). Alternatively, an antibody can be engineered which has dual Fc regions and may thereby have enhanced complement lysis and ADCC capabilities. See Stevenson et al., Anti-Cancer Drug Design 3:219-230 (1989).

To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Antibodies of the present invention may also be modified to include an epitope tag or label, e.g., for use in purification or diagnostic applications. The invention also pertains to therapy with immunoconjugates comprising an antibody conjugated to an anti-cancer agent such as a cytotoxic agent or a growth inhibitory agent. Chemotherapeutic agents useful in the generation of such immunoconjugates have been described above.

Conjugates of an antibody and one or more small molecule toxins, such as a calicheamicin, maytansinoids, a trichothene, and CC1065, and the derivatives of these toxins that have toxin activity, are also contemplated herein.

In one preferred embodiment, an antibody (full length or fragments) of the invention is conjugated to one or more maytansinoid molecules. Maytansinoids are mitototic inhibitors that act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

In an attempt to improve their therapeutic index, maytansine and maytansinoids have been conjugated to antibodies specifically binding to tumor cell antigens. Immunoconjugates containing maytaminoids and their therapeutic use are disclosed, for example, in U.S. Pat. Nos. 5,208,020, 5,416,064 and European Patent EP 0 425 235 B1. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay.

Antibody-maytansinoid conjugates are prepared by chemically linking an antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody conjugates, including, for example, those disclosed in U.S. Pat. No. 5,208,020 or EP Patent 0 425 235 B1, and Chari et al., Cancer Research 52: 127-131 (1992). The linking groups include disufide groups, thioether groups, acid labile groups, photolabile groups, peptidase labile groups, or esterase labile groups, as disclosed in the above-identified patents, disulfide and thioether groups being preferred.

Immunoconjugates may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio)propionate (SPDP) (Carlsson et al., Biochem. J. 173:723-737 [1978]) and N-succinimidyl-4-(2-pyridylthio)pentanoate (SPP) to provide for a disulfide linkage. For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, Cancer Research 52: 127-131 (1992); U.S. Pat. No. 5,208,020) may be used.

Another immunoconjugate of interest comprises an antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Another drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Examples of other agents that can be conjugated to the antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof that can be used include, e.g., diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232.

The present invention further includes an immunoconjugate formed between an antibody and a compound with nucleolytic activity (e.g., a ribonuclease or a DNA endonuclease such as a deoxyribonuclease; DNase).

For selective destruction of infected cells, the antibody includes a highly radioactive atom. A variety of radioactive isotopes are available for the production of radioconjugated anti-PSCA antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for diagnosis, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123, iodine-131, indium-111, fluorine-19, carbon-13, nitrogen-15, oxygen-17, gadolinium, manganese or iron.

The radio- or other label is incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al. (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Alternatively, a fusion protein comprising the antibody and cytotoxic agent is made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

The antibodies of the present invention are also used in antibody dependent enzyme mediated prodrug therapy (ADET) by conjugating the antibody to a prodrug-activating enzyme which converts a prodrug (e.g., a peptidyl chemotherapeutic agent, see WO81/01145) to an active anti-cancer drug (see, e.g., WO 88/07378 and U.S. Pat. No. 4,975,278).

The enzyme component of the immunoconjugate useful for ADEPT includes any enzyme capable of acting on a prodrug in such a way so as to covert it into its more active, cytotoxic form. Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases; such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, Nature 328: 457-458 (1987)). Antibody-abzyme conjugates can be prepared as described herein for delivery of the abzyme to a infected cell population.

The enzymes of this invention can be covalently bound to the antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., Nature, 312: 604-608 (1984).

Other modifications of the antibody are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly-(methylmethacylate)microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences,* 16th edition, Oslo, A., Ed., (1980).

The antibodies disclosed herein are also formulated as immunoliposomes. A "liposome" is a small vesicle composed of various types of lipids, phospholipids and/or surfactant that is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., Proc. Natl. Acad. Sci. USA, 82:3688 (1985); Hwang et al., Proc. Natl. Acad. Sci. USA, 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired a diameter. Fab' fragments of the antibody of the present invention can be conjugated to the liposomes as described in Martin et al., J. Biol. Chem. 257: 286-288 (1982) via a disulfide interchange reaction. A chemotherapeutic agent is optionally contained within the liposome. See Gabizon et al., J. National Cancer Inst. 81(19)1484 (1989).

Antibodies of the present invention, or fragments thereof, may possess any of a variety of biological or functional characteristics. In certain embodiments, these antibodies are Influenza A specific or M2 protein specific antibodies, indicating that they specifically bind to or preferentially bind to Influenza A or the M2 protein thereof, respectively, as compared to a normal control cell. In particular embodiments, the antibodies are HuM2e antibodies, indicating that they specifically bind to a M2e protein, preferably to an epitope of the M2e domain that is only present when the M2 protein is expressed in cells or present on a virus, as compared to a normal control cell.

In particular embodiments, an antibody of the present invention is an antagonist antibody, which partially or fully blocks or inhibits a biological activity of a polypeptide or cell to which it specifically or preferentially binds. In other embodiments, an antibody of the present invention is a growth inhibitory antibody, which partially or fully blocks or inhibits the growth of an infected cell to which it binds. In another embodiment, an antibody of the present invention induces apoptosis. In yet another embodiment, an antibody of the present invention induces or promotes antibody-dependent cell-mediated cytotoxicity or complement dependent cytotoxicity.

Methods of Identifying and Producing Antibodies Specific for Influenza Virus

The present invention provides novel methods for the identification of HuM2e antibodies, as exemplified in Example 4. These methods may be readily adapted to identify antibodies specific for other polypeptides expressed on the cell surface by infectious agents, or even polypeptides expressed on the surface of an infectious agent itself.

In general, the methods include obtaining serum samples from patients that have been infected with or vaccinated against an infectious agent. These serum samples are then screened to identify those that contain antibodies specific for a particular polypeptide associated with the infectious agent, such as, e.g., a polypeptide specifically expressed on the surface of cells infected with the infectious agent, but not uninfected cells. In particular embodiments, the serum samples are screened by contacting the samples with a cell that has been transfected with an expression vector that expresses the polypeptide expressed on the surface of infected cells.

Once a patient is identified as having serum containing an antibody specific for the infectious agent polypeptide of interest is identified, mononuclear and/or B cells obtained from the same patient are used to identify a cell or clone thereof that produces the antibody, using any of the methods described herein or available in the art. Once a B cell that produces the antibody is identified, cDNAs encoding the variable regions or fragments thereof of the antibody may be cloned using standard RT-PCR vectors and primers specific for conserved antibody sequences, and subcloned in to expression vectors used for the recombinant production of monoclonal antibodies specific for the infectious agent polypeptide of interest.

In one embodiment, the present invention provides a method of identifying an antibody that specifically binds influenza A-infected cells, comprising: contacting an Influenza A virus or a cell expressing the M2 protein with a biological sample obtained from a patient having been infected by Influenza A; determining an amount of antibody in the biological sample that binds to the cell; and comparing the amount determined with a control value, wherein if the value determined is at least two-fold greater than the control value, an antibody that specifically binds influenza A-infected cells is indicated. In various embodiments, the cells expressing an M2 protein are cells infected with an Influenza A virus or cells that have been transfected with a polynucleotide that expressed the M2 protein. Alternatively, the cells may express a portion of the M2 protein that includes the M2e domain and enough additional M2 sequence that the protein remains associated with the cell and the M2e domain is presented on the cell surface in the same manner as when present within full length M2 protein. Methods of preparing an M2 expression vector and transfecting an appropriate cell, including those described herein, may be readily accomplished, in view of the M2 sequence being publicly available. See, for example, the Influenza Sequence Database (ISD) (flu.lan1.gov on the World Wide Web, described in Macken et al., 2001, "The value of a database in surveillance and vaccine selection" in Options for the Control of Influenza IV. A.D.M.E., Osterhaus & Hampson (Eds.), Elsevier Science, Amsterdam, pp. 103-106) and the Microbial Sequencing Center (MSC) at The Institute for Genomic Research (TIGR) (tigr.org/msc/infl_a_virus.shtml on the World Wide Web).

The M2e-expressing cells or virus described above are used to screen the biological sample obtained from a patient infected with influenza A for the presence of antibodies that preferentially bind to the cell expressing the M2 polypeptide using standard biological techniques. For example, in certain embodiments, the antibodies may be labeled, and the presence of label associated with the cell detected, e.g., using FMAT or FACs analysis. In particular embodiments, the biological sample is blood, serum, plasma, bronchial lavage, or saliva. Methods of the present invention may be practiced using high throughput techniques.

Identified human antibodies may then be characterized further. For example the particular conformational epitopes with in the M2e protein that are necessary or sufficient for binding of the antibody may be determined, e.g., using site-directed mutagenesis of expressed M2e polypeptides. These methods may be readily adapted to identify human antibodies that bind any protein expressed on a cell surface. Furthermore, these methods may be adapted to determine binding of the antibody to the virus itself, as opposed to a cell expressing recombinant M2e or infected with the virus.

Polynucleotide sequences encoding the antibodies, variable regions thereof, or antigen-binding fragments thereof may be subcloned into expression vectors for the recombinant production of HuM2e antibodies. In one embodiment, this is accomplished by obtaining mononuclear cells from the patient from the serum containing the identified HuM2e antibody was obtained; producing B cell clones from the mononuclear cells; inducing the B cells to become antibody-producing plasma cells; and screening the supernatants produced by the plasma cells to determine if it contains the HuM2e antibody. Once a B cell clone that produces an HuM2e antibody is identified, reverse-transcription polymerase chain reaction (RT-PCR) is performed to clone the DNAs encoding the variable regions or portions thereof of the HuM2e antibody. These sequences are then subcloned into expression vectors suitable for the recombinant production of human HuM2e antibodies. The binding specificity may be confirmed by determining the recombinant antibody's ability to bind cells expressing M2e polypeptide.

In particular embodiments of the methods described herein, B cells isolated from peripheral blood or lymph nodes are sorted, e.g., based on their being CD19 positive, and plated, e.g., as low as a single cell specificity per well, e.g., in 96, 384, or 1536 well configurations. The cells are induced to differentiate into antibody-producing cells, e.g., plasma cells, and the culture supernatants are harvested and tested for binding to cells expressing the infectious agent polypeptide on their surface using, e.g., FMAT or FACS analysis. Positive wells are then subjected to whole well RT-PCR to amplify heavy and light chain variable regions of the IgG molecule expressed by the clonal daughter plasma cells. The resulting PCR products encoding the heavy and light chain variable regions, or portions thereof, are subcloned into human antibody expression vectors for recombinant expression. The resulting recombinant antibodies are then tested to confirm their original binding specificity and may be further tested for pan-specificity across various strains of isolates of the infectious agent.

Thus, in one embodiment, a method of identifying HuM2e antibodies is practiced as follows. First, full length or approximately full length M2 cDNAs are transfected into a cell line for expression of M2 protein. Secondly, individual human plasma or sera samples are tested for antibodies that bind the cell-expressed M2. And lastly, MAbs derived from plasma- or serum-positive individuals are characterized for binding to the same cell-expressed M2. Further definition of the fine specificities of the MAbs can be performed at this point.

These methods may be practiced to identify a variety of different HuM2e antibodies, including antibodies specific for (a) epitopes in a linear M2e peptide, (b) common epitopes in multiple variants of M2e, (c) conformational determinants of an M2 homotetramer, and (d) common conformational determinants of multiple variants of the M2 homotetramer. The last category is particularly desirable, as this specificity is perhaps specific for all A strains of influenza.

Polynucleotides that encode the HuM2e antibodies or portions thereof of the present invention may be isolated from cells expressing HuM2e antibodies, according to methods available in the art and described herein, including amplification by polymerase chain reaction using primers specific for conserved regions of human antibody polypeptides. For example, light chain and heavy chain variable regions may be cloned from the B cell according to molecular biology techniques described in WO 92/02551; U.S. Pat. No. 5,627,052; or Babcook et al., *Proc. Natl. Acad. Sci. USA* 93:7843-48 (1996). In certain embodiments, polynucleotides encoding all or a region of both the heavy and light chain variable regions of the IgG molecule expressed by the clonal daughter plasma cells expressing the HuM2e antibody are subcloned and sequenced. The sequence of the encoded polypeptide may be readily determined from the polynucleotide sequence. Isolated polynucleotides encoding a polypeptide of the present invention may be subcloned into an expression vector to recombinantly produce antibodies and polypeptides of the present invention, using procedures known in the art and described herein.

Binding properties of an antibody (or fragment thereof) to M2e or infected cells or tissues may generally be determined and assessed using immunodetection methods including, for example, immunofluorescence-based assays, such as immuno-histochemistry (IHC) and/or fluorescence-activated cell sorting (FACS). Immunoassay methods may include controls and procedures to determine whether antibodies bind specifically to M2e from one or more specific strains of Influenza A, and do not recognize or cross-react with normal control cells.

Following pre-screening of serum to identify patients that produce antibodies to an infectious agent or polypeptide thereof, e.g., M2, the methods of the present invention typically include the isolation or purification of B cells from a biological sample previously obtained from a patient or subject. The patient or subject may be currently or previously diagnosed with or suspect or having a particular disease or infection, or the patient or subject may be considered free or a particular disease or infection. Typically, the patient or subject is a mammal and, in particular embodiments, a human. The biological sample may be any sample that contains B cells, including but not limited to, lymph node or lymph node tissue, pleural effusions, peripheral blood, ascites, tumor tissue, or cerebrospinal fluid (CSF). In various embodiments, B cells are isolated from different types of biological samples, such as a biological sample affected by a particular disease or infection. However, it is understood that any biological sample comprising B cells may be used for any of the embodiments of the present invention.

Once isolated, the B cells are induced to produce antibodies, e.g., by culturing the B cells under conditions that support B cell proliferation or development into a plasmacyte, plasmablast, or plasma cell. The antibodies are then screened, typically using high throughput techniques, to identify an antibody that specifically binds to a target antigen, e.g., a particular tissue, cell, infectious agent, or polypeptide. In certain embodiments, the specific antigen, e.g., cell surface polypeptide bound by the antibody is not known, while in other embodiments, the antigen specifically bound by the antibody is known.

According to the present invention, B cells may be isolated from a biological sample, e.g., a tumor, tissue, peripheral blood or lymph node sample, by any means known and available in the art. B cells are typically sorted by FACS based on the presence on their surface of a B cell-specific marker, e.g., CD19, CD138, and/or surface IgG. However, other methods known in the art may be employed, such as, e.g., column purification using CD19 magnetic beads or IgG-specific magnetic beads, followed by elution from the column. However, magnetic isolation of B cells utilizing any marker may result in loss of certain B cells. Therefore, in certain embodiments, the isolated cells are not sorted but, instead, phicol-purified mononuclear cells isolated from tumor are directly plated to the appropriate or desired number of specificities per well.

In order to identify B cells that produce an infectious agent-specific antibody, the B cells are typically plated at low density (e.g., a single cell specificity per well, 1-10 cells per well, 10-100 cells per well, 1-100 cells per well, less than 10 cells per well, or less than 100 cells per well) in multi-well or microtitre plates, e.g., in 96, 384, or 1536 well configurations. When the B cells are initially plated at a density greater than one cell per well, then the methods of the present invention may include the step of subsequently diluting cells in a well identified as producing an antigen-specific antibody, until a single cell specificity per well is achieved, thereby facilitating the identification of the B cell that produces the antigen-specific antibody. Cell supernatants or a portion thereof and/or cells may be frozen and stored for future testing and later recovery of antibody polynucleotides.

In certain embodiments, the B cells are cultured under conditions that favor the production of antibodies by the B cells. For example, the B cells may be cultured under conditions favorable for B cell proliferation and differentiation to yield antibody-producing plasmablast, plasmacytes, or plasma cells. In particular embodiments, the B cells are cultured in the presence of a B cell mitogen, such as lipopolysaccharide (LPS) or CD40 ligand. In one specific embodiment, B cells are differentiated to antibody-producing cells by culturing them with feed cells and/or other B cell activators, such as CD40 ligand.

Cell culture supernatants or antibodies obtained therefrom may be tested for their ability to bind to a target antigen, using routine methods available in the art, including those described herein. In particular embodiments, culture supernatants are tested for the presence of antibodies that bind to a target antigen using high-throughput methods. For example, B cells may be cultured in multi-well microtitre dishes, such that robotic plate handlers may be used to simultaneously sample multiple cell supernatants and test for the presence of antibodies that bind to a target antigen. In particular embodiments, antigens are bound to beads, e.g., paramagnetic or latex beads) to facilitate the capture of antibody/antigen complexes. In other embodiments, antigens and antibodies are fluorescently labeled (with different labels) and FACS analysis is performed to identify the presence of antibodies that bind to target antigen. In one embodiment, antibody binding is determined using FMAT™ analysis and instrumentation (Applied Biosystems, Foster City, Calif.). FMAT™ is a fluorescence macro-confocal platform for high-throughput screening, which mix-and-read, non-radioactive assays using live cells or beads.

In the context of comparing the binding of an antibody to a particular target antigen (e.g., a biological sample such as infected tissue or cells, or infectious agents) as compared to a control sample (e.g., a biological sample such as uninfected cells, or a different infectious agent), in various embodiments, the antibody is considered to preferentially bind a particular target antigen if at least two-fold, at least three-fold, at least five-fold, or at least ten-fold more antibody binds to the particular target antigen as compared to the amount that binds a control sample.

Polynucleotides encoding antibody chains, variable regions thereof, or fragments thereof, may be isolated from cells utilizing any means available in the art. In one embodiment, polynucleotides are isolated using polymerase chain reaction (PCR), e.g., reverse transcription-PCR (RT-PCR) using oligonucleotide primers that specifically bind to heavy or light chain encoding polynucleotide sequences or complements thereof using routine procedures available in the art. In one embodiment, positive wells are subjected to whole well RT-PCR to amplify the heavy and light chain variable regions of the IgG molecule expressed by the clonal daughter plasma cells. These PCR products may be sequenced.

The resulting PCR products encoding the heavy and light chain variable regions or portions thereof are then subcloned into human antibody expression vectors and recombinantly expressed according to routine procedures in the art (see, e.g., U.S. Pat. No. 7,112,439). The nucleic acid molecules encoding a tumor-specific antibody or fragment thereof, as described herein, may be propagated and expressed according to any of a variety of well-known procedures for nucleic acid excision, ligation, transformation, and transfection. Thus, in certain embodiments expression of an antibody fragment may be preferred in a prokaryotic host cell, such as *Escherichia coli* (see, e.g., Pluckthun et al., *Methods Enzymol.* 178:497-515 (1989)). In certain other embodiments, expression of the antibody or an antigen-binding fragment thereof may be preferred in a eukaryotic host cell, including yeast (e.g., *Saccharomyces cerevisiae, Schizosaccharomyces pombe*, and *Pichia pastoris*); animal cells (including mammalian cells); or plant cells. Examples of suitable animal cells include, but are not limited to, myeloma, COS, CHO, or hybridoma cells. Examples of plant cells include tobacco, corn, soybean, and rice cells. By methods known to those having ordinary skill in the art and based on the present disclosure, a nucleic acid vector may be designed for expressing foreign sequences in a particular host system, and then polynucleotide sequences encoding the tumor-specific antibody (or fragment thereof) may be inserted. The regulatory elements will vary according to the particular host.

One or more replicable expression vectors containing a polynucleotide encoding a variable and/or constant region may be prepared and used to transform an appropriate cell line, for example, a non-producing myeloma cell line, such as a mouse NSO line or a bacteria, such as *E. coli*, in which production of the antibody will occur. In order to obtain efficient transcription and translation, the polynucleotide sequence in each vector should include appropriate regulatory sequences, particularly a promoter and leader sequence operatively linked to the variable domain sequence. Particular methods for producing antibodies in this way are generally well known and routinely used. For example, molecular biology procedures are described by Sambrook et al. (*Molecular Cloning, A Laboratory Manual,* 2nd ed., Cold Spring Harbor Laboratory, New York, 1989; see also Sambrook et al., 3rd ed., Cold Spring Harbor Laboratory, New York, (2001)). While not required, in certain embodiments, regions of polynucleotides encoding the recombinant antibodies may be sequenced. DNA sequencing can be performed as described in Sanger et al. (*Proc. Natl. Acad. Sci. USA* 74:5463 (1977)) and the Amersham International plc sequencing handbook and including improvements thereto.

In particular embodiments, the resulting recombinant antibodies or fragments thereof are then tested to confirm their original specificity and may be further tested for pan-specificity, e.g., with related infectious agents. In particular embodiments, an antibody identified or produced according to methods described herein is tested for cell killing via antibody dependent cellular cytotoxicity (ADCC) or apoptosis, and/or well as its ability to internalize.

Polynucleotides

The present invention, in other aspects, provides polynucleotide compositions. In preferred embodiments, these polynucleotides encode a polypeptide of the invention, e.g., a region of a variable chain of an antibody that binds to Influenza A, M2, or M2e. Polynucleotides of the invention are single-stranded (coding or antisense) or double-stranded DNA (genomic, cDNA or synthetic) or RNA molecules. RNA molecules include, but are not limited to, HnRNA molecules, which contain introns and correspond to a DNA molecule in a one-to-one manner, and mRNA molecules, which do not contain introns. Alternatively, or in addition, coding or non-coding sequences are present within a polynucleotide of the present invention. Also alternatively, or in addition, a polynucleotide is linked to other molecules and/or support materials of the invention. Polynucleotides of the invention are used, e.g., in hybridization assays to detect the presence of an Influenza A antibody in a biological sample, and in the recombinant production of polypeptides of the invention.

Therefore, according to another aspect of the present invention, polynucleotide compositions are provided that include some or all of a polynucleotide sequence set forth in Example 1, complements of a polynucleotide sequence set forth in Example 1, and degenerate variants of a polynucleotide sequence set forth in Example 1. In certain preferred embodiments, the polynucleotide sequences set forth herein encode polypeptides capable of preferentially binding a Influenza A-infected cell as compared to a normal control uninfected cell, including a polypeptide having a sequence set forth in Examples 1 or 2. Furthermore, the invention includes all polynucleotides that encode any polypeptide of the present invention.

In other related embodiments, the invention provides polynucleotide variants having substantial identity to the sequences set forth in FIG. 1, for example those comprising at least 70% sequence identity, preferably at least 75%, 80%, 85%, 90%, 95%, 96%, 97%, 98%, or 99% or higher, sequence identity compared to a polynucleotide sequence of this invention, as determined using the methods described herein, (e.g., BLAST analysis using standard parameters). One skilled in this art will recognize that these values can be appropriately adjusted to determine corresponding identity of proteins encoded by two nucleotide sequences by taking into account codon degeneracy, amino acid similarity, reading frame positioning, and the like.

Typically, polynucleotide variants contain one or more substitutions, additions, deletions and/or insertions, preferably such that the immunogenic binding properties of the polypeptide encoded by the variant polynucleotide is not substantially diminished relative to a polypeptide encoded by a polynucleotide sequence specifically set forth herein. In additional embodiments, the present invention provides polynucleotide fragments comprising various lengths of contiguous stretches of sequence identical to or complementary to one or more of the sequences disclosed herein. For example, polynucleotides are provided by this invention that comprise at least about 10, 15, 20, 30, 40, 50, 75, 100, 150, 200, 300, 400, 500 or 1000 or more contiguous nucleotides of one or more of the sequences disclosed herein as well as all intermediate lengths there between. As used herein, the term "intermediate lengths" is meant to describe any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like.

In another embodiment of the invention, polynucleotide compositions are provided that are capable of hybridizing under moderate to high stringency conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at 50° C.-60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60-65° C. or 65-70° C.

In preferred embodiments, the polypeptide encoded by the polynucleotide variant or fragment has the same binding specificity (i.e., specifically or preferentially binds to the same epitope or Influenza A strain) as the polypeptide encoded by the native polynucleotide. In certain preferred embodiments, the polynucleotides described above, e.g., polynucleotide variants, fragments and hybridizing sequences, encode polypeptides that have a level of binding activity of at least about 50%, preferably at least about 70%, and more preferably at least about 90% of that for a polypeptide sequence specifically set forth herein.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. A nucleic acid fragment of almost any length is employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are included in many implementations of this invention.

It will be appreciated by those of ordinary skill in the art that, as a result of the degeneracy of the genetic code, there are multiple nucleotide sequences that encode a polypeptide as described herein. Some of these polynucleotides bear minimal homology to the nucleotide sequence of any native gene. Nonetheless, polynucleotides that encode a polypeptide of the present invention but which vary due to differences in codon usage are specifically contemplated by the invention. Further, alleles of the genes including the polynucleotide sequences provided herein are within the scope of the invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

In certain embodiments of the present invention, mutagenesis of the disclosed polynucleotide sequences is performed in order to alter one or more properties of the encoded polypeptide, such as its binding specificity or binding strength. Techniques for mutagenesis are well-known in the art, and are widely used to create variants of both polypeptides and polynucleotides. A mutagenesis approach, such as site-specific mutagenesis, is employed for the preparation of variants and/or derivatives of the polypeptides described herein. By this approach, specific modifications in a polypeptide sequence are made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide. Site-specific mutagenesis allows the production of mutants through the use of specific oligonucleotide sequences include the nucleotide sequence of the desired mutation, as well as a sufficient number of adjacent nucleotides, to provide a primer sequence of sufficient size and sequence complexity to form a stable duplex on both sides of the deletion junction being traversed. Mutations are employed in a selected polynucleotide sequence to improve, alter, decrease, modify, or otherwise change the properties of the polynucleotide itself, and/or alter the properties, activity, composition, stability, or primary sequence of the encoded polypeptide.

In other embodiments of the present invention, the polynucleotide sequences provided herein are used as probes or primers for nucleic acid hybridization, e.g., as PCR primers. The ability of such nucleic acid probes to specifically hybridize to a sequence of interest enable them to detect the presence of complementary sequences in a given sample. However, other uses are also encompassed by the invention, such as the use of the sequence information for the preparation of mutant species primers, or primers for use in preparing other genetic constructions. As such, nucleic acid segments of the invention that include a sequence region of at least about 15 nucleotide long contiguous sequence that has the same sequence as, or is complementary to, a 15 nucleotide long contiguous sequence disclosed herein is particularly useful. Longer contiguous identical or complementary sequences, e.g., those of about 20, 30, 40, 50, 100, 200, 500, 1000 (including all intermediate lengths) including full length sequences, and all lengths in between, are also used in certain embodiments.

Polynucleotide molecules having sequence regions consisting of contiguous nucleotide stretches of 10-14, 15-20, 30, 50, or even of 100-200 nucleotides or so (including intermediate lengths as well), identical or complementary to a polynucleotide sequence disclosed herein, are particularly contemplated as hybridization probes for use in, e.g., Southern and Northern blotting, and/or primers for use in, e.g., polymerase chain reaction (PCR). The total size of fragment, as well as the size of the complementary stretch(es), ultimately depends on the intended use or application of the particular nucleic acid segment. Smaller fragments are generally used in hybridization embodiments, wherein the length of the contiguous complementary region may be varied, such as between about 15 and about 100 nucleotides, but larger contiguous complementarity stretches may be used, according to the length complementary sequences one wishes to detect.

The use of a hybridization probe of about 15-25 nucleotides in length allows the formation of a duplex molecule that is both stable and selective. Molecules having contiguous complementary sequences over stretches greater than 12 bases in length are generally preferred, though, in order to increase stability and selectivity of the hybrid, and thereby improve the quality and degree of specific hybrid molecules obtained. Nucleic acid molecules having gene-complementary stretches of 15 to 25 contiguous nucleotides, or even longer where desired, are generally preferred.

Hybridization probes are selected from any portion of any of the sequences disclosed herein. All that is required is to review the sequences set forth herein, or to any continuous portion of the sequences, from about 15-25 nucleotides in length up to and including the full length sequence, that one wishes to utilize as a probe or primer. The choice of probe and primer sequences is governed by various factors. For example, one may wish to employ primers from towards the termini of the total sequence.

Polynucleotide of the present invention, or fragments or variants thereof, are readily prepared by, for example, directly synthesizing the fragment by chemical means, as is commonly practiced using an automated oligonucleotide synthesizer. Also, fragments are obtained by application of nucleic acid reproduction technology, such as the PCR™ technology of U.S. Pat. No. 4,683,202, by introducing selected sequences into recombinant vectors for recombinant production, and by other recombinant DNA techniques generally known to those of skill in the art of molecular biology.

Vectors, Host Cells and Recombinant Methods

The invention provides vectors and host cells comprising a nucleic acid of the present invention, as well as recombinant techniques for the production of a polypeptide of the present invention. Vectors of the invention include those capable of replication in any type of cell or organism, including, e.g., plasmids, phage, cosmids, and mini chromosomes. In various embodiments, vectors comprising a polynucleotide of the present invention are vectors suitable for propagation or replication of the polynucleotide, or vectors suitable for expressing a polypeptide of the present invention. Such vectors are known in the art and commercially available.

Polynucleotides of the present invention are synthesized, whole or in parts that are then combined, and inserted into a vector using routine molecular and cell biology techniques, including, e.g., subcloning the polynucleotide into a linearized vector using appropriate restriction sites and restriction enzymes. Polynucleotides of the present invention are amplified by polymerase chain reaction using oligonucleotide primers complementary to each strand of the polynucleotide. These primers also include restriction enzyme cleavage sites to facilitate subcloning into a vector. The replicable vector components generally include, but are not limited to, one or more of the following: a signal sequence, an origin of replication, and one or more marker or selectable genes.

In order to express a polypeptide of the present invention, the nucleotide sequences encoding the polypeptide, or functional equivalents, are inserted into an appropriate expression vector, i.e., a vector that contains the necessary elements for the transcription and translation of the inserted coding sequence. Methods well known to those skilled in the art are used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J., et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

A variety of expression vector/host systems are utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. Within one embodiment, the variable regions of a gene expressing a monoclonal antibody of interest are amplified from a hybridoma cell using nucleotide primers. These primers aer synthesized by one of ordinary skill in the art, or may be purchased from commercially available sources (see, e.g., Stratagene (La Jolla, Calif.), which sells primers for amplifying mouse and human variable regions. The primers are used to amplify heavy or light chain variable regions, which are then inserted into vectors such as ImmunoZAP™ H or ImmunoZAP™ L (Stratagene), respectively. These vectors are then introduced into E. coli, yeast, or mammalian-based systems for expression. Large amounts of a single-chain protein containing a fusion of the $V_H$ and $V_L$ domains are produced using these methods (see Bird et al., Science 242:423-426 (1988)).

The "control elements" or "regulatory sequences" present in an expression vector are those non-translated regions of the vector, e.g., enhancers, promoters, 5' and 3' untranslated regions, that interact with host cellular proteins to carry out transcription and translation. Such elements may vary in their strength and specificity. Depending on the vector system and host utilized, any number of suitable transcription and translation elements, including constitutive and inducible promoters, are used.

Examples of promoters suitable for use with prokaryotic hosts include the phoa promoter, β-lactamase and lactose promoter systems, alkaline phosphatase promoter, a tryptophan (trp) promoter system, and hybrid promoters such as the tac promoter. However, other known bacterial promoters are suitable. Promoters for use in bacterial systems also usually contain a Shine-Dalgarno sequence operably linked to the DNA encoding the polypeptide. Inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like are used.

A variety of promoter sequences are known for eukaryotes and any are used according to the present invention. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

In mammalian cell systems, promoters from mammalian genes or from mammalian viruses are generally preferred. Polypeptide expression from vectors in mammalian host cells aer controlled, for example, by promoters obtained from the genomes of viruses such as polyoma virus, fowlpox virus, adenovirus (e.g., Adenovirus 2), bovine papilloma virus, avian sarcoma virus, cytomegalovirus (CMV), a retrovirus, hepatitis-B virus and most preferably Simian Virus 40 (SV40), from heterologous mammalian promoters, e.g., the actin promoter or an immunoglobulin promoter, and from heat-shock promoters, provided such promoters are compatible with the host cell systems. If it is necessary to generate a cell line that contains multiple copies of the sequence encoding a polypeptide, vectors based on SV40 or EBV may be advantageously used with an appropriate selectable marker. One example of a suitable expression vector is pcDNA-3.1 (Invitrogen, Carlsbad, Calif.), which includes a CMV promoter.

A number of viral-based expression systems are available for mammalian expression of polypeptides. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus that is capable of expressing the polypeptide in infected host cells (Logan, J. and Shenk, T. (1984) Proc. Natl. Acad. Sci. 81:3655-3659). In addition, transcription enhancers, such as the Rous sarcoma virus (RSV) enhancer, may be used to increase expression in mammalian host cells.

In bacterial systems, any of a number of expression vectors are selected depending upon the use intended for the expressed polypeptide. For example, when large quantities are desired, vectors that direct high level expression of fusion proteins that are readily purified are used. Such vectors include, but are not limited to, the multifunctional E. coli cloning and expression vectors such as BLUESCRIPT (Stratagene), in which the sequence encoding the polypeptide of interest may be ligated into the vector in frame with sequences for the amino-terminal Met and the subsequent 7 residues of β-galactosidase, so that a hybrid protein is produced; pIN vectors (Van Heeke, G. and S. M. Schuster (1989) J. Biol. Chem. 264:5503-5509); and the like. pGEX Vectors (Promega, Madison, Wis.) are also used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin, or factor XA protease cleavage sites so that the cloned polypeptide of interest can be released from the GST moiety at will.

In the yeast, Saccharomyces cerevisiae, a number of vectors containing constitutive or inducible promoters such as alpha factor, alcohol oxidase, and PGH are used. Examples of other suitable promoter sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. For reviews, see Ausubel et al. (supra) and Grant et al. (1987) Methods Enzymol. 153:516-544. Other yeast promoters that are inducible promoters having the additional advantage of transcription controlled by growth conditions include the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

In cases where plant expression vectors are used, the expression of sequences encoding polypeptides are driven by any of a number of promoters. For example, viral promoters such as the 35S and 19S promoters of CaMV are used alone or in combination with the omega leader sequence from TMV (Takamatsu, N. (1987) EMBO J. 6:307-311. Alternatively, plant promoters such as the small subunit of RUBISCO or heat shock promoters are used (Coruzzi, G. et al. (1984) EMBO J. 3:1671-1680; Broglie, R. et al. (1984) Science 224:838-843; and Winter, J., et al. (1991) Results Probl. Cell Differ. 17:85-105). These constructs can be introduced into plant cells by direct DNA transformation or pathogen-mediated transfection. Such techniques are described in a number of generally available reviews (see, e.g., Hobbs, S. or Murry, L. E. in McGraw Hill Yearbook of Science and Technology (1992) McGraw Hill, New York, N.Y.; pp. 191-196).

An insect system is also used to express a polypeptide of interest. For example, in one such system, *Autographa californica* nuclear polyhedrosis virus (AcNPV) is used as a vector to express foreign genes in *Spodoptera frugiperda* cells or in *Trichoplusia* larvae. The sequences encoding the polypeptide are cloned into a non-essential region of the virus, such as the polyhedrin gene, and placed under control of the polyhedrin promoter. Successful insertion of the polypeptide-encoding sequence renders the polyhedrin gene inactive and produce recombinant virus lacking coat protein. The recombinant viruses are then used to infect, for example, *S. frugiperda* cells or *Trichoplusia* larvae, in which the polypeptide of interest is expressed (Engelhard, E. K. et al. (1994) Proc. Natl. Acad. Sci. 91:3224-3227).

Specific initiation signals are also used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon are provided. Furthermore, the initiation codon is in the correct reading frame to ensure correct translation of the inserted polynucleotide. Exogenous translational elements and initiation codons are of various origins, both natural and synthetic.

Transcription of a DNA encoding a polypeptide of the invention is often increased by inserting an enhancer sequence into the vector. Many enhancer sequences are known, including, e.g., those identified in genes encoding globin, elastase, albumin, α-fetoprotein, and insulin. Typically, however, an enhancer from a eukaryotic cell virus is used. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer is spliced into the vector at a position 5' or 3' to the polypeptide-encoding sequence, but is preferably located at a site 5' from the promoter.

Expression vectors used in eukaryotic host cells (yeast, fungi, insect, plant, animal, human, or nucleated cells from other multicellular organisms) typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding anti-PSCA antibody. One useful transcription termination component is the bovine growth hormone polyadenylation region. See WO94/11026 and the expression vector disclosed therein.

Suitable host cells for cloning or expressing the DNA in the vectors herein are the prokaryote, yeast, plant or higher eukaryote cells described above. Examples of suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

*Saccharomyces cerevisiae*, or common baker's yeast, is the most commonly used among lower eukaryotic host microorganisms. However, a number of other genera, species, and strains are commonly available and used herein, such as *Schizosaccharomyces pombe*; *Kluyveromyces* hosts such as, e.g., K lactis, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris*. (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*.

In certain embodiments, a host cell strain is chosen for its ability to modulate the expression of the inserted sequences or to process the expressed protein in the desired fashion. Such modifications of the polypeptide include, but are not limited to, acetylation, carboxylation. glycosylation, phosphorylation, lipidation, and acylation. Post-translational processing that cleaves a "prepro" form of the protein is also used to facilitate correct insertion, folding and/or function. Different host cells such as CHO, COS, HeLa, MDCK, HEK293, and WI38, which have specific cellular machinery and characteristic mechanisms for such post-translational activities, are chosen to ensure the correct modification and processing of the foreign protein.

Methods and reagents specifically adapted for the expression of antibodies or fragments thereof are also known and available in the art, including those described, e.g., in U.S. Pat. Nos. 4,816,567 and 6,331,415. In various embodiments, antibody heavy and light chains, or fragments thereof, are expressed from the same or separate expression vectors. In one embodiment, both chains are expressed in the same cell, thereby facilitating the formation of a functional antibody or fragment thereof.

Full length antibody, antibody fragments, and antibody fusion proteins are produced in bacteria, in particular when glycosylation and Fc effector function are not needed, such as when the therapeutic antibody is conjugated to a cytotoxic agent (e.g., a toxin) and the immunoconjugate by itself shows effectiveness in infected cell destruction. For expression of antibody fragments and polypeptides in bacteria, see, e.g., U.S. Pat. Nos. 5,648,237, 5,789,199, and 5,840,523, which describes translation initiation region (TIR) and signal sequences for optimizing expression and secretion. After expression, the antibody is isolated from the *E. coli* cell paste in a soluble fraction and can be purified through, e.g., a protein A or G column depending on the isotype. Final purification can be carried out using a process similar to that used for purifying antibody expressed e.g., in CHO cells.

Suitable host cells for the expression of glycosylated polypeptides and antibodies are derived from multicellular organisms. Examples of invertebrate cells include plant and insect cells. Numerous baculoviral strains and variants and corresponding permissive insect host cells from hosts such as

*Spodoptera frugiperda* (caterpillar), *Aedes aegypti* (mosquito), *Aedes albopicius* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses are used as the virus herein according to the present invention, particularly for transfection of *Spodoptera frugiperda* cells. Plant cell cultures of cotton, corn, potato, soybean, petunia, tomato, and tobacco are also utilized as hosts.

Methods of propagation of antibody polypeptides and fragments thereof in vertebrate cells in culture (tissue culture) are encompassed by the invention. Examples of mammalian host cell lines used in the methods of the invention are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for polypeptide production and cultured in conventional nutrient media modified as appropriate for inducing promoters, selecting transformants, or amplifying the genes encoding the desired sequences.

For long-term, high-yield production of recombinant proteins, stable expression is generally preferred. For example, cell lines that stably express a polynucleotide of interest are transformed using expression vectors that contain viral origins of replication and/or endogenous expression elements and a selectable marker gene on the same or on a separate vector. Following the introduction of the vector, cells are allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells are proliferated using tissue culture techniques appropriate to the cell type.

A plurality of selection systems are used to recover transformed cell lines. These include, but are not limited to, the herpes simplex virus thymidine kinase (Wigler, M. et al. (1977) *Cell* 11:223-32) and adenine phosphoribosyltransferase (Lowy, I. et al. (1990) *Cell* 22:817-23) genes that are employed in tk⁻ or aprt⁻ cells, respectively. Also, antimetabolite, antibiotic or herbicide resistance is used as the basis for selection; for example, dhfr, which confers resistance to methotrexate (Wigler, M. et al. (1980) *Proc. Natl. Acad. Sci.* 77:3567-70); npt, which confers resistance to the aminoglycosides, neomycin and G-418 (Colbere-Garapin, F. et al. (1981) *J. Mol. Biol.* 150:1-14); and als or pat, which confer resistance to chlorsulfuron and phosphinotricin acetyltransferase, respectively (Murry, supra). Additional selectable genes have been described. For example, trpB allows cells to utilize indole in place of tryptophan, and hisD allows cells to utilize histinol in place of histidine (Hartman, S. C. and R. C. Mulligan (1988) *Proc. Natl. Acad. Sci.* 85:8047-51). The use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) *Methods Mol. Biol.* 55:121-131).

Although the presence/absence of marker gene expression suggests that the gene of interest is also present, its presence and expression is confirmed. For example, if the sequence encoding a polypeptide is inserted within a marker gene sequence, recombinant cells containing sequences are identified by the absence of marker gene function. Alternatively, a marker gene is placed in tandem with a polypeptide-encoding sequence under the control of a single promoter. Expression of the marker gene in response to induction or selection usually indicates expression of the tandem gene as well. Alternatively, host cells that contain and express a desired polynucleotide sequence are identified by a variety of procedures known to those of skill in the art. These procedures include, but are not limited to, DNA-DNA or DNA-RNA hybridizations and protein bioassay or immunoassay techniques which include, for example, membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Nonlimiting examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide is preferred for some applications, but a competitive binding assay may also be employed. These and other assays are described, among other places, in Hampton, R. et al. (1990; Serological Methods, a Laboratory Manual, APS Press, St Paul. Minn.) and Maddox, D. E. et al. (1983; J. Exp. Med. 158:1211-1216).

Various labels and conjugation techniques are known by those skilled in the art and are used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof are cloned into a vector for the production of an mRNA probe. Such vectors are known in the art, are commercially available, and are used to synthesize RNA probes in vitro by addition of an appropriate RNA polymerase such as T7, T3, or SP6 and labeled nucleotides. These procedures are conducted using a variety of commercially available kits. Suitable reporter molecules or labels, which are used include, but are not limited to, radionuclides, enzymes, fluorescent, chemiluminescent, or chromogenic agents as well as substrates, cofactors, inhibitors, magnetic particles, and the like.

The polypeptide produced by a recombinant cell is secreted or contained intracellularly depending on the sequence and/or the vector used. Expression vectors containing polynucleotides of the invention are designed to contain signal sequences that direct secretion of the encoded polypeptide through a prokaryotic or eukaryotic cell membrane.

In certain embodiments, a polypeptide of the invention is produced as a fusion polypeptide further including a polypeptide domain that facilitates purification of soluble proteins. Such purification-facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Amgen, Seattle, Wash.). The inclusion of cleavable linker sequences such as those specific for Factor XA or enterokinase (Invitrogen. San Diego, Calif.) between the purification domain and the encoded polypeptide are used to facilitate purification. An exemplary expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, Prot. Exp. Purif. 3:263-281) while the enterokinase cleavage site provides a means for purifying the desired polypeptide from the fusion protein. A discussion of vectors used for producing fusion proteins is provided in Kroll, D. J. et al. (1993; *DNA Cell Biol.* 12:441-453).

In certain embodiments, a polypeptide of the present invention is fused with a heterologous polypeptide, which may be a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells, the signal sequence is selected, for example, from the group of the alkaline phosphatase, penicillinase, 1 pp, or heat-stable enterotoxin II leaders. For yeast secretion, the signal sequence is selected from, e.g., the yeast invertase leader, α factor leader (including *Saccharomyces* and *Kluyveromyces* α factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

When using recombinant techniques, the polypeptide or antibody is produced intracellularly, in the periplasmic space, or directly secreted into the medium. If the polypeptide or antibody is produced intracellularly, as a first step, the particulate debris, either host cells or lysed fragments, are removed, for example, by centrifugation or ultrafiltration. Carter et al., Bio/Technology 10:163-167 (1992) describe a procedure for isolating antibodies that are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris is removed by centrifugation. Where the polypeptide or antibody is secreted into the medium, supernatants from such expression systems are generally first concentrated using a commercially available protein concentration filter, for example, an Amicon or Millipore Pellicon ultrafiltration unit. Optionally, a protease inhibitor such as PMSF is included in any of the foregoing steps to inhibit proteolysis and antibiotics is included to prevent the growth of adventitious contaminants.

The polypeptide or antibody composition prepared from the cells are purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the polypeptide or antibody. Protein A is used to purify antibodies or fragments thereof that are based on human $\gamma_1$, $\gamma_2$, or $\gamma_4$ heavy chains (Lindmark et al., J. Immunol. Meth. 62:1-13 (1983)). Protein G is recommended for all mouse isotypes and for human $\gamma_3$ (Guss et al., EMBO J. 5:15671575 (1986)). The matrix to which the affinity ligand is attached is most often agarose, but other matrices are available. Mechanically stable matrices such as controlled pore glass or poly(styrenedivinyl) benzene allow for faster flow rates and shorter processing times than can be achieved with agarose. Where the polypeptide or antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the polypeptide or antibody to be recovered. Following any preliminary purification step(s), the mixture comprising the polypeptide or antibody of interest and contaminants are subjected to low pH hydrophobic interaction chromatography using an elution buffer at a pH between about 2.5-4.5, preferably performed at low salt concentrations (e.g., from about 0-0.25M salt).

Pharmaceutical Compositions

The invention further includes pharmaceutical formulations including a polypeptide, antibody, or modulator of the present invention, at a desired degree of purity, and a pharmaceutically acceptable carrier, excipient, or stabilizer (Remingion's Pharmaceutical Sciences 16th edition, Osol, A. Ed. (1980)). In certain embodiments, pharmaceutical formulations are prepared to enhance the stability of the polypeptide or antibody during storage, e.g., in the form of lyophilized formulations or aqueous solutions. Acceptable carriers, excipients, or stabilizers are nontoxic to recipients at the dosages and concentrations employed, and include, e.g., buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g. Zn-protein complexes); and/or non-ionic surfactants such as TWEEN™, PLURONICS™ or polyethylene glycol (PEG). In certain embodiments, the therapeutic formulation preferably comprises the polypeptide or antibody at a concentration of between 5-200 mg/ml, preferably between 10-100 mg/ml.

The formulations herein also contain one or more additional therapeutic agents suitable for the treatment of the particular indication, e.g., infection being treated, or to prevent undesired side-effects. Preferably, the additional therapeutic agent has an activity complementary to the polypeptide or antibody of the resent invention, and the two do not adversely affect each other. For example, in addition to the polypeptide or antibody of the invention, an additional or second antibody, anti-viral agent, anti-infective agent and/or cardioprotectant is added to the formulation. Such molecules are suitably present in the pharmaceutical formulation in amounts that are effective for the purpose intended.

The active ingredients, e.g., polypeptides and antibodies of the invention and other therapeutic agents, are also entrapped in microcapsules prepared, for example, by coacervation techniques or by interfacial polymerization, for example, hydroxymethylcellulose or gelatin-microcapsules and polymethylmethacylate) microcapsules, respectively, in colloidal drug delivery systems (for example, liposomes, albumin microspheres, microemulsions, nano-particles and nanocapsules) or in macroemulsions. Such techniques are disclosed in Remingion's Pharmaceutical Sciences 16th edition, Osol, A. Ed. (1980).

Sustained-release preparations are prepared. Suitable examples of sustained-release preparations include, but are not limited to, semi-permeable matrices of solid hydrophobic polymers containing the antibody, which matrices are in the form of shaped articles, e.g., films, or microcapsules. Nonlimiting examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxyburyric acid.

Formulations to be used for in vivo administration are preferably sterile. This is readily accomplished by filtration through sterile filtration membranes.

Diagnostic Uses

Antibodies and fragments thereof, and therapeutic compositions, of the invention specifically bind or preferentially bind to infected cells or tissue, as compared to normal control cells and tissue. Thus, these influenza A antibodies are used to detect infected cells or tissues in a patient, biological sample, or cell population, using any of a variety of diagnostic and prognostic methods, including those described herein. The ability of an anti-M2e specific antibody to detect infected cells depends upon its binding specificity, which is readily determined by testing its ability to bind to infected cells or tissues obtained from different patients, and/or from patients infected with different strains of Influenza A. Diagnostic methods generally involve contacting a biological sample obtained from a patient, such as, e.g., blood, serum, saliva, urine, sputum, a cell swab sample, or a tissue biopsy, with an Influenza A, e.g., HuM2e antibody and determining whether the antibody preferentially binds to the sample as compared to a control sample or predetermined cut-off value, thereby indicating the presence of infected cells. In particular embodiments, at least two-fold, three-fold, or five-fold more HuM2e antibody binds to an infected cell as compared to an appropriate control normal cell or tissue sample. A pre-determined cut-off value is determined, e.g., by averaging the amount of HuM2e antibody that binds to several different appropriate control samples under the same conditions used to perform the diagnostic assay of the biological sample being tested.

Bound antibody is detected using procedures described herein and known in the art. In certain embodiments, diagnostic methods of the invention are practiced using HuM2e antibodies that are conjugated to a detectable label, e.g., a fluorophore, to facilitate detection of bound antibody. However, they are also practiced using methods of secondary detection of the HuM2e antibody. These include, for example, RIA, ELISA, precipitation, agglutination, complement fixation and immuno-fluorescence.

In certain procedures, the HuM2e antibodies are labeled. The label is detected directly. Exemplary labels that are detected directly include, but are not limited to, radiolabels and fluorochromes. Alaternatively, or in addition, labels are moieties, such as enzymes, that must be reacted or derivatized to be detected. Nonlimiting examples of isotope labels are $^{99}$Tc, $^{14}$C, $^{131}$I, $^{125}$I, $^{3}$H, $^{32}$P and $^{35}$S. Fluorescent materials that are used include, but are not limited to, for example, fluorescein and its derivatives, rhodamine and its derivatives, auramine, dansyl, umbelliferone, luciferia, 2,3-dihydrophthalazinediones, horseradish peroxidase, alkaline phosphatase, lysozyme, and glucose-6-phosphate dehydrogenase.

An enzyme label is detected by any of the currently utilized colorimetric, spectrophotometric, fluorospectro-photometric or gasometric techniques. Many enzymes which are used in these procedures are known and utilized by the methods of the invention. Nonlimiting examples are peroxidase, alkaline phosphatase, β-glucuronidase, β-D-glucosidase, β-D-galactosidase, urease, glucose oxidase plus peroxidase, galactose oxidase plus peroxidase and acid phosphatase.

The antibodies are tagged with such labels by known methods. For instance, coupling agents such as aldehydes, carbodiimides, dimaleimide, imidates, succinimides, bid-diazotized benzandine and the like are used to tag the antibodies with the above-described fluorescent, chemiluminescent, and enzyme labels. An enzyme is typically combined with an antibody using bridging molecules such as carbodiimides, periodate, diisocyanates, glutaraldehyde and the like. Various labeling techniques are described in Morrison, Methods in Enzymology 32b, 103 (1974), Syvanen et al., J. Biol. Chem. 284, 3762 (1973) and Bolton and Hunter, Biochem J. 133, 529 (1973).

HuM2e antibodies of the present invention are capable of differentiating between patients with and patients without an Influenza A infection, and determining whether or not a patient has an infection, using the representative assays provided herein. According to one method, a biological sample is obtained from a patient suspected of having or known to have an Influenza A infection. In preferred embodiments, the biological sample includes cells from the patient. The sample is contacted with an HuM2e antibody, e.g., for a time and under conditions sufficient to allow the HuM2e antibody to bind to infected cells present in the sample. For instance, the sample is contacted with an HuM2e antibody for 10 seconds, 30 seconds, 1 minute, 5 minutes, 10 minutes, 30 minutes, 1 hour, 6 hours, 12 hours, 24 hours, 3 days or any point in between. The amount of bound HuM2e antibody is determined and compared to a control value, which may be, e.g., a pre-determined value or a value determined from normal tissue sample. An increased amount of antibody bound to the patient sample as compared to the control sample is indicative of the presence of infected cells in the patient sample.

In a related method, a biological sample obtained from a patient is contacted with an HuM2e antibody for a time and under conditions sufficient to allow the antibody to bind to infected cells. Bound antibody is then detected, and the presence of bound antibody indicates that the sample contains infected cells. This embodiment is particularly useful when the HuM2e antibody does not bind normal cells at a detectable level. Different HuM2e antibodies possess different binding and specificity characteristics. Depending upon these characteristics, particular HuM2e antibodies are used to detect the presence of one or more strains of Influenza A. For example, certain antibodies bind specifically to only one or several strains of Influenza virus, whereas others bind to all or a majority of different strains of Influenza virus. Antibodies specific for only one strain of Influenza A are used to identify the strain of an infection.

In certain embodiments, antibodies that bind to an infected cell preferably generate a signal indicating the presence of an infection in at least about 20% of patients with the infection being detected, more preferably at least about 30% of patients. Alternatively, or in addition, the antibody generates a negative signal indicating the absence of the infection in at least about 90% of individuals without the infection being detected. Each antibody satisfies the above criteria; however, antibodies of the present invention are used in combination to improve sensitivity.

The present invention also includes kits useful in performing diagnostic and prognostic assays using the antibodies of the present invention. Kits of the invention include a suitable container comprising a HuM2e antibody of the invention in either labeled or unlabeled form. In addition, when the antibody is supplied in a labeled form suitable for an indirect binding assay, the kit further includes reagents for performing the appropriate indirect assay. For example, the kit includes one or more suitable containers including enzyme substrates or derivatizing agents, depending on the nature of the label. Control samples and/or instructions are also included.

Therapeutic/Prophylactic Uses

Passive immunization has proven to be an effective and safe strategy for the prevention and treatment of viral diseases. (See Keller et al., Clin. Microbiol. Rev. 13:602-14 (2000); Casadevall, Nat. Biotechnol. 20:114 (2002); Shibata et al., Nat. Med. 5:204-10 (1999); and Igarashi et al., Nat. Med. 5:211-16 (1999), each of which are incorporated herein by reference)). Passive immunization using human monoclonal antibodies provide an immediate treatment strategy for emergency prophylaxis and treatment of influenza.

HuM2e antibodies and fragments thereof, and therapeutic compositions, of the invention specifically bind or preferentially bind to infected cells, as compared to normal control uninfected cells and tissue. Thus, these HuM2e antibodies are used to selectively target infected cells or tissues in a patient, biological sample, or cell population. In light of the infection-specific binding properties of these antibodies, the present invention provides methods of regulating (e.g., inhibiting) the growth of infected cells, methods of killing infected cells, and methods of inducing apoptosis of infected cells. These methods include contacting an infected cell with an HuM2e antibody of the invention. These methods are practiced in vitro, ex vivo, and in vivo.

In various embodiments, antibodies of the invention are intrinsically therapeutically active. Alternatively, or in addition, antibodies of the invention are conjugated to a cytotoxic agent or growth inhibitory agent, e.g., a radioisotope or toxin, that is used in treating infected cells bound or contacted by the antibody.

In one embodiment, the invention provides methods of treating or preventing infection in a patient, including the steps of providing an HuM2e antibody of the invention to a patient diagnosed with, at risk of developing, or suspected of having an Influenza A infection. The methods of the invention are used in the first-line treatment of the infection, follow-on treatment, or in the treatment of a relapsed or refractory infection. Treatment with an antibody of the invention is a stand alone treatment. Alternatively, treatment with an antibody of the invention is one component or phase of a combination therapy regime, in which one or more additional therapeutic agents are also used to treat the patient.

Subjects at risk for an influenza virus-related diseases or disorders include patients who have come into contact with an infected person or who have been exposed to the influenza virus in some other way. Administration of a prophylactic agent can occur prior to the manifestation of symptoms characteristic of the influenza virus-related disease or disorder, such that a disease or disorder is prevented or, alternatively, delayed in its progression.

In various aspects, the huM2e is administered substantially contemporaneously with or following infection of the subject, i.e., therapeutic treatment. In another aspect, the antibody provides a therapeutic benefit. In various aspects, a therapeutic benefit includes reducing or decreasing progression, severity, frequency, duration or probability of one or more symptoms or complications of influenza infection, virus titer, virus replication or an amount of a viral protein of one or more influenza strains. still another aspect, a therapeutic benefit includes hastening or accelerating a subject's recovery from influenza infection.

Methods for preventing an increase in influenza virus titer, virus replication, virus proliferation or an amount of an influenza viral protein in a subject are further provided. In one embodiment, a method includes administering to the subject an amount of a huM2e antibody effective to prevent an increase in influenza virus titer, virus replication or an amount of an influenza viral protein of one or more influenza strains or isolates in the subject.

Methods for protecting a subject from infection or decreasing susceptibility of a subject to infection by one or more influenza strains/isolates or subtypes, i.e., prophylactic methods, are additionally provided. In one embodiment, a method includes administering to the subject an amount of huM2e antibody that specifically binds influenza M2 effective to protect the subject from infection, or effective to decrease susceptibility of the subject to infection, by one or more influenza strains/isolates or subtypes.

Optionally, the subject is further administered with a second agent such as, but not limited to, an influenza virus antibody, an anti-viral drug such as a neuraminidase inhibitor, a HA inhibitor, a sialic acid inhibitor or an M2 ion channel inhibitor, a viral entry inhibitor or a viral attachment inhibitor. The M2 ion channel inhibitor is for example amantadine or rimantadine. The neuraminidase inhibitor for example zanamivir, or oseltamivir phosphate.

Symptoms or complications of influenza infection that can be reduced or decreased include, for example, chills, fever, cough, sore throat, nasal congestion, sinus congestion, nasal infection, sinus infection, body ache, head ache, fatigue, pneumonia, bronchitis, ear infection, ear ache or death.

For in vivo treatment of human and non-human patients, the patient is usually administered or provided a pharmaceutical formulation including a HuM2e antibody of the invention. When used for in vivo therapy, the antibodies of the invention are administered to the patient in therapeutically effective amounts (i.e., amounts that eliminate or reduce the patient's viral burden). The antibodies are administered to a human patient, in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. The antibodies may be administered parenterally, when possible, at the target cell site, or intravenously. Intravenous or subcutaneous administration of the antibody is preferred in certain embodiments. Therapeutic compositions of the invention are administered to a patient or subject systemically, parenterally, or locally.

For parenteral administration, the antibodies are formulated in a unit dosage injectable form (solution, suspension, emulsion) in association with a pharmaceutically acceptable, parenteral vehicle. Examples of such vehicles are water, saline, Ringer's solution, dextrose solution, and 5% human serum albumin. Nonaqueous vehicles such as fixed oils and ethyl oleate are also used. Liposomes are used as carriers. The vehicle contains minor amounts of additives such as substances that enhance isotonicity and chemical stability, e.g., buffers and preservatives. The antibodies are typically formulated in such vehicles at concentrations of about 1 mg/ml to 10 mg/ml.

The dose and dosage regimen depends upon a variety of factors readily determined by a physician, such as the nature of the infection and the characteristics of the particular cytotoxic agent or growth inhibitory agent conjugated to the antibody (when used), e.g., its therapeutic index, the patient, and the patient's history. Generally, a therapeutically effective amount of an antibody is administered to a patient. In particular embodiments, the amount of antibody administered is in the range of about 0.1 mg/kg to about 50 mg/kg of patient body weight. Depending on the type and severity of the infection, about 0.1 mg/kg to about 50 mg/kg body weight (e.g., about 0.1-15 mg/kg/dose) of antibody is an initial candidate dosage for administration to the patient, whether, for example, by one or more separate administrations, or by continuous infusion. The progress of this therapy is readily monitored by conventional methods and assays and based on criteria known to the physician or other persons of skill in the art.

In one particular embodiment, an immunoconjugate including the antibody conjugated with a cytotoxic agent is administered to the patient. Preferably, the immunoconjugate is internalized by the cell, resulting in increased therapeutic efficacy of the immunoconjugate in killing the cell to which it binds. In one embodiment, the cytotoxic agent targets or interferes with the nucleic acid in the infected cell. Examples of such cytotoxic agents are described above and include, but are not limited to, maytansinoids, calicheamicins, ribonucleases and DNA endonucleases.

Other therapeutic regimens are combined with the administration of the HuM2e antibody of the present invention. The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

In certain embodiments, it is desirable to combine administration of an antibody of the invention with another antibody directed against another antigen associated with the infectious agent.

Aside from administration of the antibody protein to the patient, the invention provides methods of administration of the antibody by gene therapy. Such administration of nucleic acid encoding the antibody is encompassed by the expression "administering a therapeutically effective amount of an antibody". See, for example, PCT Patent Application Publication WO96/07321 concerning the use of gene therapy to generate intracellular antibodies.

In another embodiment, anti-M2e antibodies of the invention are used to determine the structure of bound antigen, e.g., conformational epitopes, the structure of which is then used to develop a vaccine having or mimicking this structure, e.g., through chemical modeling and SAR methods. Such a vaccine could then be used to prevent Influenza A infection.

All of the above U.S. patents, U.S. patent application publications, U.S. patent applications, foreign patents, foreign patent applications and non-patent publications referred to in this specification and/or listed in the Application Data Sheet are incorporated herein by reference, in their entirety.

EXAMPLES

Example 1

Screening and Characterization of M2e-Specific Antibodies Present in Human Plasma Using Cells Expressing Recombinant M2e Protein Fully human monoclonal antibodies specific for M2 and capable of binding to influenza A infected cells and the influenza virus itself were identified in patient serum, as described below.

Expression of M2 in Cell Lines

An expression construct containing the M2 full length cDNA, corresponding to the derived M2 sequence found in Influenza subtype H3N2, was transfected into 293 cells.

The M2 cDNA is encoded by the following polynucleotide sequence and SEQ ID NO: 53:

ATGAGTCTTCTAACCGAGGTCGAAACGCCTATCAGAAACGAATGGGGGTG

CAGATGCAACGATTCAAGTGATCCTCTTGTTGTTGCCGCAAGTATCATTG

GGATCCTGCACTTGATATTGTGGATTCTTGATCGTCTTTTTTTCAAATGC

ATTTATCGTCTCTTTAAACACGGTCTGAAAAGAGGGCCTTCTACGGAAGG

AGTACCAGAGTCTATGAGGGAAGAATATCGAAAGGAACAGCAGAGTGCTG

TGGATGCTGACGATAGTCATTTTGTCAACATAGAGCTGGAG

The cell surface expression of M2 was confirmed using the anti-M2e peptide specific MAb 14C2. Two other variants of M2, from A/Hong Kong/483/1997 (HK483) and A/Vietnam/1203/2004 (VN1203), were used for subsequent analyses, and their expression was determined using M2e-specific monoclonal antibodies of the present invention, since 14C2 binding may be abrogated by the various amino acid substitutions in M2e.

Screening of Antibodies in Peripheral Blood

Over 120 individual plasma samples were tested for antibodies that bound M2. None of them exhibited specific binding to the M2e peptide. However, 10% of the plasma samples contained antibodies that bound specifically to the 293-M2H3N2 cell line. This indicates that the antibodies could be categorized as binding to conformational determinants of an M2 homotetramer, and binding to conformational determinants of multiple variants of the M2 homotetramer; they could not be specific for the linear M2e peptide.

Characterization of Anti-M2 MAbs

The human MAbs identified through this process proved to bind to conformational epitopes on the M2 homotetramer. They bound to the original 293-M2 transfectant, as well as to the two other cell-expressed M2 variants. The 14C2 MAb, in addition to binding the M2e peptide, proved to be more sensitive to the M2 variant sequences. Moreover, 14C2 does not readily bind influenza virions, while the conformation specific anti-M2 MAbs did.

These results demonstrate that the methods of the invention provide for the identification of M2 MAbs from normal human immune responses to influenza without a need for specific immunization of M2. If used for immunotherapy, these fully human MAbs have the potential to be better tolerated by patients that humanized mouse antibodies. Additionally, and in contrast to 14C2 and the Gemini Biosciences MAbs, which bind to linear M2e peptide, the MAbs of the invention bind to conformational epitopes of M2, and are specific not only for cells infected with A strain influenza, but also for the virus itself. Another advantage of the MAbs of the invention is that they each bind all of the M2 variants yet tested, indicating that they are not restricted to a specific linear amino acid sequence.

Example 2

Identification of M2-Specific Antibodies

Mononuclear or B cells expressing three of the MAbs identified in human serum as described in Example 1 were diluted into clonal populations and induced to produce antibodies. Antibody containing supernatants were screened for binding to 293 FT cells stably transfected with the full length M2E protein from influenza strain Influenza subtype H3N2.

Supernatants which showed positive staining/binding were re-screened again on 293 FT cells stably transfected with the full length M2E protein from influenza strain Influenza subtype H3N2 and on vector alone transfected cells as a control.

The variable regions of the antibodies were then rescue cloned from the B cell wells whose supernatants showed positive binding. Transient transfections were performed in 293 FT cells to reconstitute and produce these antibodies. Reconstituted antibody supernatants were screened for binding to 293 FT cells stably transfected with the full length M2E protein as detailed above to identify the rescued anti-M2E antibodies. Three different antibodies were identified: 8i10, 21B15 and 23K12. A fourth additional antibody clone was isolated by the rescue screens, 4C2. However, it was not unique and had the exact same sequence as clone 8i10 even though it came from a different donor than clone 8i10.

The sequences of the kappa and gamma variable regions of these antibodies are provided below.

Clone 8i10:

The Kappa LC variable region of the anti M2 clone 8i10 was cloned as Hind III to BsiW1 fragment (see below), and is encoded by the following polynucleotide sequences, and SEQ ID NO: 54 (top) and SEQ ID NO: 55 (bottom):

```
HindIII
AAGCTTCCACCATGGACATGAGGGTCCTCGCTCAGCTCCTGGGGCTCCTG
TTCGAAGGTGGTACCTGTACTCCCAGGAGCGAGTCGAGGACCCCGAGGAC CTACTCTGGCTCCGAGGTGCCAGATGTGACATCCAGATCACCCAGTCTCC
GATGAGACCGAGGCTCCACGGTCTACACTGTAGGTCTACTGGGTCAGAGG ATCCTCCCTGTCTGCATCTGTAGGACACAGAGTCACCATCACTTGCCGGG
TAGGAGGGACAGACGTAGACATCCTCTGTCTCAGTGGTAGTGAACGGCCC CGAGTCAGAACATTTACAAGTATTTAAATTGGTATCAGCAGAGACCAGGG
GCTCAGTCTTGTAAATGTTCATAAATTTAACCATAGTCGTCTCTGGTCCC AAAGCCCCTAAGGGCCTGATCTCTGCTGCATCCGGGTTGCAAAGTGGGGT
TTTCGGGGATTCCCGGACTAGAGACGACGTAGGCCCAACGTTTCACCCCA CCCATCAAGGTTCAGTGGCAGTGGATCTGGGACAGATTTCACTCTCACCA
GGGTAGTTCCAAGTCACCGTCACCTAGACCCTGTCTAAAGTGAGAGTGGT TCACCAGTCTGCAACCTGAAGATTTTGCAACTTACTACTGTCAACAGAGT
AGTGGTCAGACGTTGGACTTCTAAAACGTTGAATGATGACAGTTGTCTCA BsiWI
TACAGTCCCCCTCTCACTTTCGGCGGAGGGACCAGGGTGGAGATCAAACG
ATGTCAGGGGGAGAGTGAAAGCCGCCTCCCTGGTCCCACCTCTAGTTTGC

TACG
ATGC
```

The translation of the 8i10 Kappa LC variable region is as follows, polynucleotide sequence (above, SEQ ID NO: 54, top) and amino acid sequence (below, corresponding to SEQ ID NO: 56):

```
HindIII
AAGCTTCCACCATGGACATGAGGGTCCTCGCTCAGCTCCTGGGGCTCCTG
            M  D  M  R  V  L  A  Q  L  L  G  L  L CTACTCTGGCTCCGAGGTGCCAGATGTGACATCCAGATGACCCAGTCTCC
 L  L  W  L  R  G  A  R  C  D  I  Q  M  T  Q  S  P ATCCTCCCTGTCTGCATCTGTAGGAGACAGAGTCACCATCACTTGCCGGG
  S  S  L  S  A  S  V  G  D  R  V  T  I  T  C  R CGAGTCAGAACATTTACAAGTATTTAAATTGGTATCAGCAGAGACCAGGG
A  S  Q  N  I  Y  K  Y  L  N  W  Y  Q  Q  R  P  G AAAGCCCCTAAGGGCCTGATCTCTGCTGCATCCGGGTTGCAAAGTGGGGT
 K  A  P  K  G  L  I  S  A  A  S  G  L  Q  S  G  V
```

-continued

```
CCCATCAAGGTTCAGTGGCAGTGGATCTGGGACAGATTTCACTCTCACCA
  P  S  R  F  S  G  S  G  S  G  T  D  F  T  L  T

TCACCAGTCTGCAACCTGAAGATTTTGCAACTTACTACTGTCAACAGAGT
I  T  S  L  Q  P  E  D  F  A  T  Y  Y  C  Q  Q  S

BsiWI
TACAGTCCCCCTCTCACTTTCGGCGGAGGGACCAGGGTGGAGATCAAACG
 Y  S  P  P  L  T  F  G  G  G  T  R  V  E  I  K  R

TACG
  T
```

The amino acid sequence of the 8i10 Kappa LC variable region is as follows, with specific domains identified below (CDR sequences defined according to Kabat methods):

```
VK leader
                                        (SEQ ID NO: 57)
M D M R V L A Q L L G L L L L W L R G A R C FR1
                                        (SEQ ID NO: 58)
D I Q M T Q S P S S L S A S V G D R V T I T C CDR1
                                        (SEQ ID NO: 59)
R A S Q N I Y K Y L N FR2
                                        (SEQ ID NO: 60)
W Y Q Q R P G K A P K G L I S

CDR2
                                        (SEQ ID NO: 61)
A A S G L Q S

FR3
                                        (SEQ ID NO: 62)
G V P S R F S G S G S G T D F T L T I T S L Q P E

D F A T Y Y C

CDR3
                                        (SEQ ID NO: 63)
Q Q S Y S P P L T

FR4
                                        (SEQ ID NO: 64)
F G G G T R V E I K

Start of Kappa constant region
R T
```

The following is an example of the Kappa LC variable region of 8i10 cloned into the expression vector pcDNA3.1 which already contained the Kappa LC constant region (upper polynucleotide sequence corresponds to SEQ ID NO: 65, lower polynucleotide sequence corresponds to SEQ ID NO: 66, amino acid sequence corresponds to SEQ ID NO: 56 shown above). Bases in black represents pcDNA3.1 vector sequences, underlined bases represent the cloned antibody sequences. The antibodies described herein have also been cloned into the expression vector pCEP4.

```
                                     NheI (894) PmeI (900) HindIII (910)
TCGAAATTAATACGACTCACTATAGGGAGACCCAAGCTGGCTAGCGTTTAAACTTAAGCTTCCACCATGGACATGAGGGTCCTC
AGCTTTAATTATGCTGAGTGATATCCCTCTGGGTTCGACCGATCGCAAATTTGAATTCGAAGGTGGTACCTGTACTCCCAGGAG
                                                                  ■ M  D  M  R  V  L GCTCAGCTCCTGGGGCTCCTGCTACTCTGGCTCCGAGGTGCCAGATGTGACATCCAGATGACCCAGTCT
CGAGTCGAGGACCCCGAGGACGATGAGACCGAGGCTCCACGGTCTACACTGTAGGTCTACTGGGTCAGA
■ A  Q  L  L  G  L  L  L  L  W  L  R  G  A  R  C  D  I  Q  M  T  Q  S CCATCCTCCCTGTCTGCATCTGTAGGAGACAGAGTCACCATCACTTGCCGGGCGAGTCAGAACATTTAC
GGTAGGAGGGACAGACGTAGACATCCTCTGTCTCAGTGGTAGTGAACGGCCCGCTCAGTCTTGTAAATG
■ P  S  S  L  S  A  S  V  G  D  R  V  T  I  T  C  R  A  S  Q  N  I  Y AAGTATTTAAATTGGTATCAGCAGAGACCAGGGAAAGCCCCTAAGGGCCTGATCTCTGCTGCATCCGGG
TTCATAAATTTAACCATAGTCGTCTCTGGTCCCTTTCGGGGATTCCCGGACTAGAGACGACGTAGGCCC
■ K  Y  L  N  W  Y  Q  Q  R  P  G  K  A  P  K  G  L  I  S  A  A  S  G TTGCAAAGTGGGGTCCCATCAAGGTTCAGTGGCAGTGGATCTGGGACAGATTTCACTCTCACCATCACC
AACGTTTCACCCCAGGGTAGTTCCAAGTCACCGTCACCTAGACCCTGTCTAAAGTGAGAGTGGTAGTGG
■ L  Q  S  G  V  P  S  R  F  S  G  S  G  S  G  T  D  F  T  L  T  I  T AGTCTGCAACCTGAAGATTTTGCAACTTACTACTGTCAACAGAGTTACAGTCCCCCTCTCACTTTCGGC
TCAGACGTTGGACTTCTAAAACGTTGAATGATGACAGTTGTCTCAATGTCAGGGGGAGAGTGAAAGCCG
■ S  L  Q  P  E  D  F  A  T  Y  Y  C  Q  Q  S  Y  S  P  P  L  T  F  G BsiWI
GGAGGGGACCAGGGTGGAGATCAAACGTACGGTGGCTGCACCATCTGTCTTCATCTTCCCGCCATCTGATGAGCAGTTGAAATCTGG
CCTCCCTGGTCCCACCTCTAGTTTGCATGCCACCGACGTGGTAGACAGAAGTAGAAGGGCGGTAGACTACTCGTCAACTTTAGACC
■ G  G  T  R  V  E  I  K  R  T  V  A  A  P  S  V  F  I  F  P  P  S  D  E  Q  L  K  S  G hu Kappa constant
AACTGCCTCTGTTGTGTGCCTGCTGAATAACTTCTATCCCAGAGAGGCCAAAGTACAGTGGAAGGTGGATAACGCCCTCCAATCGGGTAACTCCC
TTGACGGAGACAACACACGGACGACTTATTGAAGATAGGGTCTCTCCGGTTTCATGTCACCTTCCACCTATTGCGGGAGGTTAGCCCATTGAGGG
   T  A  S  V  V  C  L  L  N  N  F  Y  P  R  E  A  K  V  Q  W  K  V  D  N  A  L  Q  S  G  N  S AGGAGAGTGTCACAGAGCAGGACAGCAAGGACAGCACCTACAGCCTCAGCAGCACCCTGACGCTGAGCAAAGCAGACTACGAGAAACACAAAGTC
TCCTCTCACAGTGTCTCGTCCTGTCGTTCCTGTCGTGGATGTCGGAGTCGTCGTGGGACTGCGACTCGTTTCGTCTGATGCTCTTTGTGTTTCAG
   Q  E  S  V  T  E  Q  D  S  K  D  S  T  Y  S  L  S  S  T  L  T  L  S  K  A  D  Y  E  K  H  K  V DraII (1641)
                                                                           XbaI (1636) ApaI (1642)
TACGCCTGCGAAGTCACCCATCAGGGCCTGAGCTCGCCCGTCACAAAGAGCTTCAACAGGGGAGAGTGTTAGAGGGTCTAGAGGGCCCGTTTAAA
ATGCGGACGCTTCAGTGGGTAGTCCCGGACTCGAGCGGGCAGTGTTTCTCGAAGTTGTCCCCTCTCACAATCTCCCAGATCTCCCGGGCAAATTT
   Y  A  C  E  V  T  H  Q  G  L  S  S  P  V  T  K  S  F  N  R  G  E  C
```

The 8i10 Gamma HC variable region was cloned as a Hind III to Xho 1 fragment, and is encoded the following polynucleotide sequences, and SEQ ID NO: 67 (top) and SEQ ID NO: 68 (bottom).

```
HindIII
AAGCTTCCACCATGAAACACCTGTGGTTCTTCCTTCTCCTGGTGGCAGCT
TTCGAAGGTGGTACTTTGTGGACACCAAGAAGGAAGAGGACCACCGTCGA CCCAGCTGGGTCCTGTCCCAGGTGCAATTGCAGGAGTCGGGCCCAGGACT
GGGTCGACCCAGGACAGGGTCCACGTTAACGTCCTCAGCCCGGGTCCTGA GGTGAAGCCTTCGGAGACCCTGTCCCTCACCTGCACTGTCTCTGGTTCGT
CCACTTCGGAAGCCTCTGGGACAGGGAGTGGACGTGACAGAGACCAAGCA CCATCAGTAATTACTACTGGAGCTGGATCCGGCAGTCCCCAGGGAAGGGA
GGTAGTCATTAATGATGACCTCGACCTAGGCCGTCAGGGGTCCCTTCCCT
```

```
-continued
CTGGAGTGGATTGGGTTTATCTATTACGGTGGAAACACCAAGTACAATCC
GACCTCACCTAACCCAAATAGATAATGCCACCTTTGTGGTTCATGTTAGG CTCCCTCAAGAGCCGCGTCACCATATCACAAGACACTTCCAAGAGTCAGG
GAGGGAGTTCTCGGCGCAGTGGTATAGTGTTCTGTGAAGGTTCTCAGTCC TCTCCCTGACGATGAGCTCTGTGACCGCTGCGGAATCGGCCGTCTATTTC
AGAGGGACTGCTACTCGAGACACTGGCGACGCCTTAGCCGGCAGATAAAG TGTGCGAGAGCGTCTTGTAGTGGTGGTTACTGTATCCTTGACTACTGGGG
ACACGCTCTCGCAGAACATCACCACCAATGACATAGGAACTGATGACCCC XhoI
CCAGGGAACCCTGGTCACCGTCTCGAG
GGTCCCTTGGGACCAGTGGCAGAGCTC
```

The translation of the 8i10 Gamma HC is as follows, polynucleotide sequence (above, SEQ ID NO: 67, top) and amino acid sequence (below, corresponding to SEQ ID NO: 69):

```
HindIII
AAGCTTCCACCATGAAACACCTGTGGTTCTTCCTTCTCCTGGTGGCAGCTCCCAGCTGGGTC
               M  K  H  L  W  F  F  L  L  L  V  A  A  P  S  W  V CTGTCCCAGGTGCAATTGCAGGAGTCGGGCCCAGGACTGGTGAAGCCTTCGGAGACCCTG
   L  S  Q  V  Q  L  Q  E  S  G  P  G  L  V  K  P  S  E  T  L TCCCTCACCTGCACTGTCTCTGGTTCGTCCATCAGTAATTACTACTGGAGCTGGATCCGG
   S  L  T  C  T  V  S  G  S  S  I  S  N  Y  Y  W  S  W  I  R

CAGTCCCCAGGGAAGGGACTGGAGTGGATTGGGTTTATCTATTACGGTGGAAACACCAAG
```

```
                       -continued
Q   S   P   G   K   G   L   E   W   I   G   F   I   Y   V   G   G   N   T   K TACAATCCCTCCCTCAAGAGCCGCGTCACCATATCACAAGACACTTCCAAGAGTCAGGTC
 V   N   P   S   L   K   S   R   V   T   I   S   Q   D   T   S   K   S   Q   V TCCCTGACGATGAGCTCTGTGACCGCTGCGGAATCGGCCGTCTATTTCTGTGCGAGAGCG
 S   L   T   M   S   S   V   T   A   A   E   S   A   V   Y   F   C   A   R   A XhoI
TCTTGTAGTGGTGGTTACTGTATCCTTGACTACTGGGGCCAGGGAACCCTGGTCACCGTC
 S   C   S   G   G   Y   C   I   L   D   Y   W   G   Q   G   T   L   V   T   V

TCGAG
 S
```

The amino acid sequence of the 8i10 Gamma HC is as follows with specific domains identified below (CDR sequences defined according to Kabat methods):

VH leader
(SEQ ID NO: 70)
M K H L W F F L L L V A A P S W V L S

FR1
(SEQ ID NO: 71)
Q V Q L Q E S G P G L V K P S E T L S L T C T V S
G S S I S

CDR1
(SEQ ID NO: 72)
N Y Y W S

FR2
(SEQ ID NO: 73)
W I R Q S P G K G L E W I G

CDR2
(SEQ ID NO: 74)
F I Y Y G G N T K Y N P S L K S

FR3
(SEQ ID NO: 75)
R V T I S Q D T S K S Q V S L T M S S V T A A E S
A V Y F C A R

CDR3
(SEQ ID NO: 76)
A S C S G G Y C I L D

FR4
(SEQ ID NO: 77)
Y W G Q G T L V T V S

The following is an example of the Gamma HC variable region of 8i10 cloned into the expression vector pcDNA3.1 which already contained the Gamma HC constant region (upper polynucleotide sequence corresponds to SEQ ID NO: 78, lower polynucleotide sequence corresponds to SEQ ID NO: 79, amino acid sequence corresponds to SEQ ID NO: 69 shown above). Bases in black represents pcDNA3.1 vector sequences, blue underlined bases represent the cloned antibody sequences.

```
                            PmeI (900)
                   NheI (894)        HindIII (910)
       TGGCTTATCGAAATTAATACGACTCACTATAGGGAGACCCAAGCTGGCTAGCGTTTAAACTTAAGCTTCCACCATGAAACACCTGTGGTT
       ACCGAATAGCTTTAATTATGCTGAGTGATATCCCTCTGGGTTCGACCGATCGCAAATTTGAATTCGAAGGTGGTACTTTGTGGACACCAA
                                                                        ■   M   K   H   L   W   F CTTCCTTCTCCTGGTGGCAGCTCCCAGCTGGGTCCTGTCCCAGGTGCAATTGCAGCAGTCGGGCCCA
       GAAGGAAGAGGACCACCGTCGAGGGTCGACCCAGGACAGGGTCCACGTTAACGTCCTCAGCCCGGGT
       ■   F   L   L   L   V   A   A   P   S   W   V   L   S   Q   V   Q   L   Q   E   S   G   P GGACTGGTGAAGCCTTCGGAGACCCTGTCCCTCACCTGCACTGTCTCTGGTTCGTCCATCAGTAATT
       CCTGACCACTTCGCAAGCCTCTGGGACAGGGAGTGGACGTGACAGAGACCAAGCAGGTAGTCATTAA
       ■   G   L   V   K   P   S   E   T   L   S   L   T   C   T   V   S   G   S   S   I   S   N ACTACTGGAGCTGGATCCGGCAGTCCCCAGGGAAGGGACTGGAGTGGATTGGGTTTATCTATTACGG
       TGATGACCTCGACCTAGGCCGTCAGGGGTCCCTTCCCTGACCTCACCTAACCCAAATAGATAATGCC
       ■Y   Y   W   S   W   I   R   Q   S   P   G   K   G   L   E   W   I   G   F   I   Y   Y   G TGGAAACACCAAGTACAATCCCTCCCTCAAGAGCCGCGTCACCATATCACAAGACACTTCCAAGAGT
       ACCTTTGTGGTTCATGTTAGGGAGGGAGTTCTCGGCGCAGTGGTATAGTGTTCTGTGAAGGTTCTCA
       ■   G   N   T   K   Y   N   P   S   L   K   S   R   V   T   I   S   Q   D   T   S   K   S CAGGTCTCCCTGACGATGAGCTCTGTGACCGCTGCGGAATCGGCCGTCTATTTCTGTGCGAGAGCGT
       GTCCAGAGGGACTGCTACTCGAGACACTGGCGACGCCTTAGCCGGCAGATAAAGACACGCTCTCGCA
       ■   Q   V   S   L   T   M   S   S   V   T   A   A   E   S   A   V   Y   F   C   A   R   A XhoI (1331)
       CTTGTAGTGGTGGTTACTGTATCCTTGACTACTGGGGCCAGGGAACCCTGGTCACCGTCTCGAGAGCCTCCA
       GAACATCACCACCAATGACATAGGAACTGATGACCCCGGTCCCTTGGGACCAGTGGCAGAGCTCTCGGAGGT
       ■S   C   S   G   G   Y   C   I   L   D   Y   W   G   Q   G   T   L   V   T   V   S   R   A   S
```

```
CCAAGGGCCCATCGGTCTTCCCCCTGGCACCCTCCTCCAAGAGCACCTCTGGGGGCACAGCGGCCCTGGGCTGCCTGGTCAAGGACTACTTCCCCGAACCGG
GGTTCCCGGGTAGCCAGAAGGGGGACCGTGGGAGGAGGTTCTCGTGGAGACCCCCGTGTCGCCGGGACCCGACGGACCAGTTCCTGATGAAGGGGCTTGGCC
 T  K  G  P  S  V  F  P  L  A  P  S  S  K  S  T  S  G  G  T  A  A  L  G  C  L  V  K  D  Y  F  P  E  P

TGACGGTGTCGTGGAACTCAGGCGCCCTGACCAGCGGCGTGCACACCTTCCCGGCTGTCCTACAGTCCTCAGGACTCTACTCCCTCAGCAGCGTGGTGACCG
ACTGCCACAGCACCTTGAGTCCGCGGGACTGGTCGCCGCACGTGTGGAAGGGCCGACAGGATGTCAGGAGTCCTGAGATGAGGGAGTCGTCGCACCACTGGC
 V  T  V  S  W  N  S  G  A  L  T  S  G  V  H  T  F  P  A  V  L  Q  S  S  G  L  Y  S  L  S  S  V  V  T

TGCCCTCCAGCAGCTTGGGCACCCAGACCTACATCTGCAACGTGAATCACAAGCCCAGCAACACCAAGGTGGACAAGAGAGTTGAGCCCAAATCTTGTGACA
ACGGGAGGTCGTCGAACCCGTGGGTCTGGATGTAGACGTTGCACTTAGTGTTCGGGTCGTTGTGGTTCCACCTGTTCTCTCAACTCGGGTTTAGAACACTGT
 V  P  S  S  S  L  G  T  Q  T  Y  I  C  N  V  N  H  K  P  S  N  T  K  V  D  K  R  V  E  P  K  S  C  D

AAACTCACACATGCCCACCGTGCCCAGCACCTGAACTCCTGGGGGGACCGTCAGTCTTCCTCTTCCCCCCAAAACCCAAGGACACCCTCATGATCTCCCGGA
TTTGAGTGTGTACGGGTGGCACGGGTCGTGGACTTGAGGACCCCCCTGGCAGTCAGAAGGAGAAGGGGGGTTTTGGGTTCCTGTGGGAGTACTAGAGGGCCT
 K  T  H  T  C  P  P  C  P  A  P  E  L  L  G  G  P  S  V  F  L  F  P  P  K  P  K  D  T  L  M  I  S  R

CCCCTGAGGTCACATGCGTGGTGGTGGACGTGAGCCACGAAGACCCTGAGGTCAAGTTCAACTGGTACGTGGACGGCGTGGAGGTGCATAATGCCAAGACAA
GGGGACTCCAGTGTACGCACCACCACCTGCACTCGGTGCTTCTGGGACTCCAGTTCAAGTTGACCATGCACCTGCCGCACCTCCACGTATTACGGTTCTGTT
 T  P  E  V  T  C  V  V  V  D  V  S  H  E  D  P  E  V  K  F  N  W  Y  V  D  G  V  E  V  H  N  A  K  T

AGCCGCGGGAGGAGCAGTACAACAGCACGTACCGTGTGGTCAGCGTCCTCACCGTCCTGCACCAGGACTGGCTGAATGGCAAGGAGTACAAGTGCAAGGTCT
TCGGCGCCCTCCTCGTCATGTTGTCGTGCATGGCACACCAGTCGCAGGAGTGGCAGGACGTGGTCCTGACCGACTTACCGTTCCTCATGTTCACGTTCCAGA
 K  P  R  E  E  Q  Y  N  S  T  Y  R  V  V  S  V  L  T  V  L  H  Q  D  W  L  N  G  K  E  Y  K  C  K  V

CCAACAAAGCCCTCCCAGCCCCCATCGAGAAAACCATCTCCAAAGCCAAAGGGCAGCCCCGAGAACCACAGGTGTACACCCTGCCCCCATCCCGGGAGGAGA
GGTTGTTTCGGGAGGGTCGGGGGTAGCTCTTTTGGTAGAGGTTTCGGTTTCCCGTCGGGGCTCTTGGTGTCCACATGTGGGACGGGGTAGGGCCTCCTCT
 S  N  K  A  L  P  A  P  I  E  K  T  I  S  K  A  K  G  Q  P  R  E  P  Q  V  Y  T  L  P  P  S  R  E  E

TGACCAAGAACCAGGTCAGCCTGACCTGCCTGGTCAAAGGCTTCTATCCCAGCGACATCGCCGTGGAGTGGGAGAGCAATGGGCAGCCGGAGAACAACTACA
ACTGGTTCTTGGTCCAGTCGGACTGGACGGACCAGTTTCCGAAGATAGGGTCGCTGTAGCGGCACCTCACCCTCTCGTTACCCGTCGGCCTCTTGTTGATGT
 M  T  K  N  Q  V  S  L  T  C  L  V  K  G  F  Y  P  S  D  I  A  V  E  W  E  S  N  G  Q  P  E  N  N  Y

AGACCACGCCTCCCGTGCTGGACTCCGACGGCTCCTTCTTCCTCTATAGCAAGCTCACCGTGGACAAGAGCAGGTGGCAGCAGGGGAACGTCTTCTCATGCT
TCTGGTGCGGAGGGCACGACCTGAGGCTGCCGAGGAAGAAGGAGATATCGTTCGAGTGGCACCTGTTCTGCTCCACCGTCGTCCCCTTGCAGAAGAGTACGA
 K  T  T  P  P  V  L  D  S  D  G  S  F  F  L  Y  S  K  L  T  V  D  K  S  R  W  Q  Q  G  N  V  F  S  C
```

```
                                                              ApaI (2339)
                                                             DraII (2338)
                                                 XbaI (2333)  PmeI (2345)
CCGTGATGCATGAGGCTCTGCACAACCACTACACGCAGAAGAGCCTCTCCCTGTCTCCGGGTAAATGAGTTCTAGAGGGCCCGTTTAAACCCGCTGATCAGC
GGCACTACGTACTCCGAGACGTGTTGGTGATGTGCGTCTTCTCGGAGAGGGACAGAGGCCCATTTACTCAAGATCTCCCGGGCAAATTTGGGCGACTAGTCG
 S  V  M  H  E  A  L  H  N  H  Y  T  Q  K  S  L  S  L  S  P  G  K

CTCGACTGTGCCTTCTAGTTGCCAGCCATCTGTTGTTTGC
GAGCTGACACGGAAGATCAACGGTCGGTAGACAACAAACG
```

The framework 4 (FR4) region of the Gamma HC normally ends with two serines (SS), so that the full framework 4 region should be W G Q G T L V T V S S (SEQ ID NO: 80). The accepting Xho 1 site and one additional base downstream of the Xho1 site in the vector, in which the Gamma HC constant region that the Gamma HC variable regions are cloned, supplies the last bases, which encode this final amino acid of framework 4. However, the original vector did not adjust for the silent mutation made when the Xho1 site (CTCGAG, SEQ ID NO: 81) was created and contained an "A" nucleotide downstream of the Xho1 site, which caused an amino acid change at the end of framework 4: a serine to arginine (S to R) substitution present in all the working Gamma HC clones. Thus, the full framework 4 region reads W G Q G T L V T V S R (SEQ ID NO: 82). Future constructs are being created wherein the base downstream of the Xho 1 site is a "C" nucleotide. Thus, the creation of the Xho 1 site used for cloning of the Gamma HC variable region sequences in alternative embodiments is a silent mutation and restores the framework 4 amino acid sequence to its proper W G Q G T L V T V S S (SEQ ID NO: 80). This is true for all M2 Gamma HC clones described herein.

Clone 21B15:

The Kappa LC variable region of the anti M2 clone 21B15 was cloned as Hind III to BsiW1 fragment, and is encoded by the following polynucleotide sequences and SEQ ID NO: 83 and SEQ ID NO: 84:

```
HindIII
AAGCTTCCACCATCGACATGAGGGTCCTCGCTCAGCTCCTGGGGCTCCTG
TTCGAAGGTGGTACCTGTACTCCCAGGAGCGAGTCGAGGACCCCGAGCAC CTACTCTGGCTCCGAGGTGCCAGATGTGACATCCAGGTGACCCAGTCTCC
GATGAGACCGAGGCTCCACGGTCTACACTGTAGGTCCACTGGGTCAGAGG ATCCTCCCTGTCTGCATCTGTAGGAGACAGAGTCACCATCACTTGCCGCG
TAGGAGGGACAGACGTAGACATCCTCTGTCTCAGTGGTAGTGAACGGCGC CGAGTCAGAACATTTACAAGTATTTAAATTGGTATCAGCAGAGACCAGGG
GCTCAGTCTTGTAAATGTTCATAAATTTAACCATAGTCGTCTCTGGTCCC AAAGCCCCTAAGGGCCTGATCTCTGCTGCATCCGGGTTGCAAAGTGGGGT
TTTCGGCGATTCCCGGACTAGAGACGACGTAGGCCCAACGTTTCACCCCA CCCATCAAGGTTCAGTGGCAGTGGATCTGGGACAGATTTCACTCTCACCA
GGGTAGTTCCAAGTCACCGTCACCTAGACCCTGTCTAAAGTGAGAGTGGT TCACCAGTCTGCAACCTGAAGATTTTGCAACTTACTACTGTCAACAGAGT
AGTGGTCAGACGTTGGACTTCTAAAACGTTGAATGATGACAGTTGTCTCA
```

```
                                                        BsiWI
TACAGTCCCCCTCTCACTTTCGGCGGAGGGACCAGGGTGGATATCAAACG
ATGTCAGGGGGAGAGTGAAAGCCGCCTCCCTGGTCCCACCTATAGTTTGC

TACG
ATGC
```

The translation of the 21B15 Kappa LC variable region is as follows, polynucleotide sequence (above, SEQ ID NO: 83, top) and amino acid sequence (below, corresponding to SEQ ID NO: 56):

```
HindIII
AAGCTTCCACCATGGACATGAGGGTCCTCGCTCAGCTCCTGGGGCTCCTGCTACTCTGGCTCCGAGGT
            M   D   M   R   V   L   A   G   L   L   G   L   L   L   L   W   L   R   G GCCAGATGTGACATCCAGGTGACCCAGTCTCCATCCTCCCTGTCTGCATCTGTAGGAGACAGAGTCACC
 A   R   C   D   I   Q   V   T   Q   S   P   S   S   L   S   A   S   V   G   D   R   V   T ATCACTTGCCGCGCGAGTCAGAACATTTACAAGTATTTAAATTGGTATCAGCAGAGACCAGGGAAAGCC
 I   T   C   R   A   S   Q   N   I   Y   K   Y   L   N   W   Y   Q   Q   R   P   G   K   A CCTAAGGGCCTGATCTCTGCTGCATCCGGGTTGCAAAGTGGGGTCCCATCAAGGTTCAGTGGCAGTGGA
 P   K   G   L   I   S   A   A   S   G   L   Q   S   G   V   P   S   R   F   S   G   S   G TCTGGGACAGATTTCACTCTCACCATCACCAGTCTGCAACCTGAAGATTTTGCAACTTACTACTGTCAA
 S   G   T   D   F   T   L   T   I   T   S   L   Q   P   E   D   F   A   T   Y   Y   C   Q BsiWI
CACAGTTACAGTCCCCCTCTCACTTTCGGCGGAGGGACCAGGGTGGATATCAAACGTACG
 Q   S   Y   S   P   P   L   T   F   G   G   G   T   R   V   D   I   K   R   T
```

The amino acid sequence of the 21B15 Kappa LC variable region is as follows, with specific domains identified below (CDR sequences defined according to Kabat methods):

```
VK leader
                                    (SEQ ID NO: 57)
M D M R V L A Q L L G L L L L W L R G A R C FR1
                                    (SEQ ID NO: 58)
D I Q V T Q S P S S L S A S V G D R V T I T C

CDR1
                                    (SEQ ID NO: 59)
R A S Q N I Y K Y L N

FR2
                                    (SEQ ID NO: 60)
W Y Q Q R P G K A P K G L I S

CDR2
                                    (SEQ ID NO: 61)
A A S G L Q S

FR3
                                    (SEQ ID NO: 62)
G V P S R F S G S G S T D F T L T I T S L Q P E
D F A T Y Y C

CDR3
                                    (SEQ ID NO: 63)
Q Q S Y S P P L T

FR4
                                    (SEQ ID NO: 64)
F G G G T R V D I K

Start of Kappa constant region
R T
```

The primer used to clone the Kappa LC variable region extended across a region of diversity and had wobble base position in its design. Thus, in the framework 4 region a D or E amino acid could occur. In some cases, the amino acid in this position in the rescued antibody may not be the original parental amino acid that was produced in the B cell. In most kappa LCs the position is an E. Looking at the clone above (21B15) a D in framework 4 (DIK RT) (SEQ ID NO: 84) was observed. However, looking at the surrounding amino acids, this may have occurred as the result of the primer and may be an artifact. The native antibody from the B cell may have had an E in this position.

The 21B15 Gamma HC variable region was cloned as a Hind III to Xho 1 fragment, and is encoded by the following polynucleotide sequences and SEQ ID NO: 85 (top), and SEQ ID NO: 86 (bottom):

```
HindIII
AAGCTTCCACCATGAAACACCTGTGGTTCTTCCTTCTCCTGGTGGCAGCT
TTCGAAGGTGGTACTTTGTGGACACCAAGAAGGAAGAGGACCACCGTCGA CCCAGCTGGGTCCTGTCCCAGGTGCAATTGCAGGAGTCGGGCCCAGGACT
GGGTCGACCCAGGACAGGGTCCACGTTAACGTCCTCAGCCCGGGTCCTGA GGTGAAGCCTTCGGAGACCCTGTCCCTCACCTGCACTGTCTCTGGTTCGT
CCACTTCGGAAGCCTCTGGGACAGGGAGTGGACGTGACAGAGACCAAGCA CCATCAGTAATTACTACTGGAGCTGGATCCGGCAGTCCCCAGGGAAGGGA
GGTAGTCATTAATGATGACCTCGACCTAGGCCGTCAGGGGTCCCTTCCCT CTGGAGTGGATTGGGTTTATCTATTACGGTGGAAACACCAAGTACAATCC
GACCTCACCTAACCCAAATAGATAATGCCACCTTTGTGGTTCATGTTAGG CTCCCTCAAGAGCCGCGTCACCATATCACAAGACACTTCCAAGAGTCAGG
GAGGGAGTTCTCGGCGCAGTGGTATAGTGTTCTGTGAAGGTTCTCAGTCC TCTCCCTGACGATGAGCTCTGTGACCGCTGCGGAATCGGCCGTCTATTTC
AGAGGGACTGCTACTCGAGACACTGGCGACGCCTTAGCCGGCAGATAAAG TGTGCGAGAGCGTCTTGTAGTGGTGGTTACTGTATCCTTGACTACTGGGG
ACACGCTCTCGCAGAACATCACCACCAATGACATAGGAACTGATGACCCC XhoI
CCAGGGAACCCTGGTCACCGTCTCGAG
GGTCCCTTGGGACCAGTGGCAGAGCTC
```

The translation of the 21B15 Gamma HC is as follows, polynucleotide sequence (above, SEQ ID NO: 87, top) and amino acid sequence (below, corresponding to SEQ ID NO: 69):

```
HindIII
AAGCTTCCACCATGAAACACCTGTGGTTCTTCCTTCTCCTGGTGGCAGCTCCCAGCTGGGTC
            M  K  H  L  W  F  F  L  L  L  V  A  A  P  S  W  V CTGTCCCAGGTGCAATTGCAGGAGTCGGGCCCAGGACTGGTGAAGCCTTCGGAGACCCTGTCC
  L  S  Q  V  Q  L  Q  E  S  G  P  G  L  V  K  P  S  E  T  L  S CTCACCTGCACTGTCTCTGGTTCGTCCATCAGTAATTACTACTGGAGCTGGATCCGGCAGTCC
  L  T  C  T  V  S  G  S  S  I  S  N  Y  Y  W  S  W  I  R  G  S CCAGGGAAGGGACTGGAGTGGATTGGGTTTATCTATTACGGTGGAAACACCAAGTACAATCCC
  P  G  K  G  L  E  W  I  G  F  I  Y  Y  G  G  N  T  K  Y  N  P TCCCTCAAGAGCCGCGTCACCATATCACAAGACACTTCCAAGAGTCAGGTCTCCCTGACGATG
  S  L  K  S  R  V  T  I  S  Q  D  T  S  K  S  Q  V  S  L  T  M AGCTCTGTGACCGCTGCGGAATCGGCCGTCTATTTCTGTGCGAGAGCGTCTTGTAGTGGTGGT
  S  S  V  T  A  A  E  S  A  V  V  F  C  A  R  A  S  C  S  G  G XhoI
TACTGTATCCTTGACTACTGGGGCCAGGGAACCCTGGTCACCGTCTCGAG
  Y  C  I  L  D  Y  W  G  G  G  T  L  V  T  V  S
```

The amino acid sequence of the 21B15 Gamma HC is as follows, with specific domains identified below (CDR sequences defined according to Kabat methods):

VH leader (SEQ ID NO: 70)
M K H L W F F L L L V A A P S W V L S

FR1 (SEQ ID NO: 71)
Q V P L Q E S G P G L V K P S E T L S L T C T V S G S S I S

CDR1 (SEQ ID NO: 72)
N Y Y W S

FR2 (SEQ ID NO: 73)
W I R Q S P G K G L E W I G

CDR2 (SEQ ID NO: 74)
F I Y Y G G N T K Y N P S L K S

FR3 (SEQ ID NO: 75)
R V T I S Q D T S K S Q V S L T M S S V T A A E S A V Y F C A R

CDR3 (SEQ ID NO: 76)
A S C S G G Y C I L D

FR4 (SEQ ID NO: 77)
Y W G Q G T L V T V S

Clone 23K12:

The Kappa LC variable region of the anti M2 clone 23K12 was cloned as Hind III to BsiW1 fragment (see below), and is encoded by the following polynucleotide sequences SEQ ID NO: 88 (top) and SEQ ID NO: 89 (below).

```
HindIII
AAGCTTCCACCATGGACATGAGGGTCCTCGCTCAGCTCCTGGGGCTCCTG
TTCGAAGGTGGTACCTGTACTCCCAGGAGCGAGTCGAGGACCCCGAGGAC CTACTCTGGCTCCGAGGTGCCAGATGTGACATCCAGATGACCCAGTCTCC
GATGAGACCGAGGCTCCACGGTCTACACTGTAGGTCTACTGGGTCAGAGG ATCCTCCCTGTCTGCATCTGTAGGAGACAGAGTCACCATCACTTGCCGGA
TAGGAGGGACAGACGTAGACATCCTCTGTCTCAGTGGTAGTGAACGGCCT CAAGTCAGAGCATTAGCAGCTATTTAAATTGGTATCAGCAGAAACCAGGG
GTTCAGTCTCGTAATCGTCGATAAATTTAACCATAGTCGTCTTTGGTCCC AAAGCCCCTAAACTCCTGATCTATGCTGCATCCAGTTTGCAAAGTGGGGT
TTTCGGGGATTTGAGGACTAGATACGACGTAGGTCAAACGTTTCACCCCA CCCATCAAGGTTCAGTGGCAGTGGATCTGGGACAGATTTCACTCTCACCA
GGGTAGTTCCAAGTCACCGTCACCTAGACCCTGTCTAAAGTGAGAGTGGT TCAGCGGTCTGCAACCTGAAGATTTTGCAACCTACTACTGTCAACAGAGT
AGTCGCCAGACGTTGGACTTCTAAAACGTTGGATGATGACAGTTGTCTCA BsiWI
TACAGTATGCCTGCCTTTGGCCAGGGGACCAAGCTGGAGATCAAACGTAC
ATGTCATACGGACGGAAACCGGTCCCCTGGTTCGACCTCTAGTTTGCATG

G
C
```

The translation of the 23K12 Kappa LC variable region is as follows, polynucleotide sequence (above, SEQ ID NO: 90, top) and amino acid sequence (below, corresponding to SEQ ID NO: 91).

```
HindIII
AAGCTTCCACCATGGACATGAGGGTCCTCGCTCAGCTCCTGGGGCTCCTGCTACTCTGGCTCCGAGG
            M  D  M  R  V  L  A  Q  L  L  G  L  L  L  L  W  L  R  G TGCCAGATGTGACATCCAGATGACCCAGTCTCCATCCTCCCTGTCTGCATCTGTAGGAGACAGAGTC
  A  R  C  D  I  Q  M  T  Q  S  P  S  S  I  S  A  S  V  G  D  R  V ACCATCACTTGCCGGACAAGTCAGAGCATTAGCAGCTATTTAAATTGGTATCAGCAGAAACCAGGGA
  T  I  T  C  R  T  S  Q  S  I  S  S  Y  L  N  W  Y  Q  Q  K  P  G AAGCCCCTAAACTCCTGATCTATGCTGCATCCAGTTTGCAAAGTGGGGTCCCATCAAGGTTCAGTGG
  K  A  P  K  L  L  I  Y  A  A  S  S  L  Q  S  G  V  P  S  R  F  S  G
```

```
CAGTGGATCTGGGACAGATTTCACTCTCACCATCAGCGGTCTGCAACCTGAAGATTTTGCAACCTAC
  S  G  S  G  T  D  F  T  L  T  I  S  G  L  Q  P  E  D  F  A  T  Y

BsiWI
TACTGTCAACAGAGTTACAGTATGCCTGCCTTTGGCCAGGGGACCAAGCTGGAGATCAAACGTACG
  Y  C  Q  Q  S  Y  S  M  P  A  F  G  Q  G  T  K  L  E  I  K  R  T
```

The amino acid sequence of the 23K12 Kappa LC variable region is as follows, with specific domains identified below (CDR sequences defined according to Kabat methods):

```
VK leader
                                    (SEQ ID NO: 57)
M D M R V L A Q L L G L L L L W L R G A R C FR1
                                    (SEQ ID NO: 58)
D I Q M T Q S P S S L S A S V G D R V T I T C

CDR1
                                    (SEQ ID NO: 92)
R T S Q S I S S Y L N

FR2
                                    (SEQ ID NO: 93)
W Y Q Q K P G K A P K L L I Y

CDR2
                                    (SEQ ID NO: 94)
A A S S L Q S G V P S R F

FR3
                                    (SEQ ID NO: 95)
S G S G S G T D F T L T I S G L Q P E D F A T Y Y
C

CDR3
                                    (SEQ ID NO: 96)
Q Q S Y S M P A

FR4
                                    (SEQ ID NO: 114)
F G Q G T K L E I K

Start of Kappa LC constant region
R T
```

The 23K12 Gamma HC variable region was cloned as a Hind III to Xho 1 fragment, and is encoded by the following polynucleotide sequences and SEQ ID NO: 97 (top) and SEQ ID NO: 98 (bottom).

```
HindIII
AAGCTTCCACCATGGAGTTGGGGCTGTGCTGGGTTTTCCTTGTTGCTATT
TTCGAAGGTGGTACCTCAACCCCGACACGACCCAAAAGGAACAACGATAA TTAAAAGGTGTCCAGTGTGAGGTGCAGCTGGTGGAGTCTGGGGGAGGCTT
AATTTTCCACAGGTCACACTCCACGTCGACCACCTCAGACCCCCTCCGAA GGTCCAGCCTGGGGGGTCCCTGAGAATCTCCTGTGCAGCCTCTGGATTCA
CCAGGTCGGACCCCCCAGGGACTCTTAGAGGACACGTCGGAGACCTAAGT CCGTCAGTAGCAACTACATGAGTTGGGTCCGCCAGGCTCCAGGGAAGGGG
GGCAGTCATCGTTGATGTACTCAACCCAGGCGGTCCGAGGTCCCTTCCCC CTGGAGTGGGTCTCAGTTATTTATAGTGGTGGTAGCACATACTACGCAGA
GACCTCACCCAGAGTCAATAAATATCACCACCATCGTGTATGATGCGTCT CTCCGTGAAGGGCAGATTCTCCTTCTCCAGAGACAACTCCAAGAACACAG
GAGGCACTTCCCGTCTAAGAGGAAGAGGTCTCTGTTGAGGTTCTTGTGTC TGTTTCTTCAAATGAACAGCCTGAGAGCCGAGGACACGGCTGTGTATTAC
ACAAAGAAGTTTACTTGTCGGACTCTCGGCTCCTGTGCCGACACATAATG TGTGCGAGATGTCTGAGCAGGATGCGGGGTTACGGTTTAGACGTCTGGGG
ACACGCTCTACAGACTCGTCCTACGCCCAATGCCAAATCTGCAGACCCC XhoI
CCAAGGGACCACGGTCACCGTCTCGAG
GGTTCCCTGGTGCCAGTGGCAGAGCTC
```

The translation of the 23K12 Gamma HC variable region is as follows, polynucleotide sequence (above, SEQ ID NO: 99, top), and amino acid sequence (below, corresponding to SEQ ID NO: 100):

```
HindIII
AAGCTTCCACCATGGAGTTGGGGCTGTGCTGGGTTTTCCTTGTTGCTATTTTAAAAGGTGTCCAG
              M  E  L  G  L  C  W  V  F  L  V  A  I  L  K  G  V  Q TGTGAGGTGCAGCTGGTGGAGTCTGGGGGAGGCTTGGTCCAGCCTGGGGGGTCCCTGAGAATCTCC
  C  E  V  Q  L  V  E  S  G  G  G  L  V  Q  P  G  G  S  L  R  I  S TGTGCAGCCTCTGGATTCACCGTCAGTAGCAACTACATGAGTTGGGTCCGCCAGGCTCCAGGGAAG
  C  A  A  S  G  F  T  V  S  S  N  Y  M  S  W  V  R  Q  A  P  G  K GGGCTGGAGTGGGTCTCAGTTATTTATAGTGGTGGTAGCACATACTACGCAGACTCCGTGAAGGGC
  G  L  E  W  V  S  V  I  Y  S  G  G  S  T  Y  Y  A  D  S  V  K  G AGATTCTCCTTCTCCAGAGACAACTCCAAGAACACAGTGTTTCTTCAAATGAACAGCCTGAGAGCC
  R  F  S  F  S  R  D  N  S  K  N  T  V  F  L  Q  M  N  S  L  R  A GAGGACACGGCTGTGTATTACTGTGCGAGATGTCTGAGCAGGATGCGGGGTTACGGTTTAGACGTC
  E  D  T  A  V  Y  Y  C  A  R  C  L  S  R  M  R  G  Y  G  L  D  V XhoI
TGGGGCCAAGGGACCACGGTCACCGTCTCGAG
  W  G  Q  G  T  T  V  T  V  S
```

The amino acid sequence of the 23K12 Gamma HC variable region is as follows, with specific domains identified below (CDR sequences defined according to Kabat methods):

VH leader
(SEQ ID NO: 101)
M E L G L C W V F L V A I L K G V Q C

FR1
(SEQ ID NO: 102)
E V Q L V E S G G G L V Q P G G S L R I S C A A S
G F T V S

CDR1
(SEQ ID NO: 103)
S N Y M S

FR2
(SEQ ID NO: 104)
W V R Q A P G K G L E W V S

CDR2
(SEQ ID NO: 105)
V I Y S G G S T Y Y A D S V K

FR3
(SEQ ID NO: 106)
G R F S F S R D N S K N T V F L Q M N S L R A E D
T A V Y Y C A R

CDR3
(SEQ ID NO: 107)
C L S R M R G Y G L D V

FR4
(SEQ ID NO: 108)
W G Q G T T V T V S

Example 3

Identification of Conserved Antibody Variable Regions

The amino acid sequences of the three antibody Kappa LC and Gamma HC variable regions were aligned to identify conserved regions and residues, as shown in FIGS. 12 and 13, respectively.

Clones 8I10 and 21B15 came from two different donors, yet they have the same exact Gamma HC and differ in the Kappa LC by only one amino acid at position 4 in the framework 1 region (amino acids M versus V, see FIG. 12), (excluding the D versus E wobble position in framework 4 of the Kappa LC).

Sequence comparisons of the variable regions of the antibodies revealed that the heavy chain of clone 8i10 was derived from germline sequence IgHV4 and that the light chain was derived from the germline sequence IgKV1.

Sequence comparisons of the variable regions of the antibodies revealed that the heavy chain of clone 21B15 was derived from germline sequence IgHV4 and that the light chain was derived from the germline sequence IgKV1.

Sequence comparisons of the variable regions of the antibodies revealed that the heavy chain of clone 23K12 was derived from germline sequence IgHV3 and that the light chain was derived from the germline sequence IgKV1.

Example 4

Production and Characterization of M2 Antibodies

The antibodies described above were produced in milligram quantities by larger scale transient transfections in 293 PEAK cells. Crude un-purified antibody supernatants were used to examine antibody binding to influenza A/Puerto Rico/8/1932 (PR8) virus on ELISA plates, and were compared to the binding of the control antibody 14C2, which was also produced by larger scale transient transfection. The anti-M2 recombinant human monoclonal antibodies bound to influenza while the control antibody did not (FIG. 9).

Figure 10:
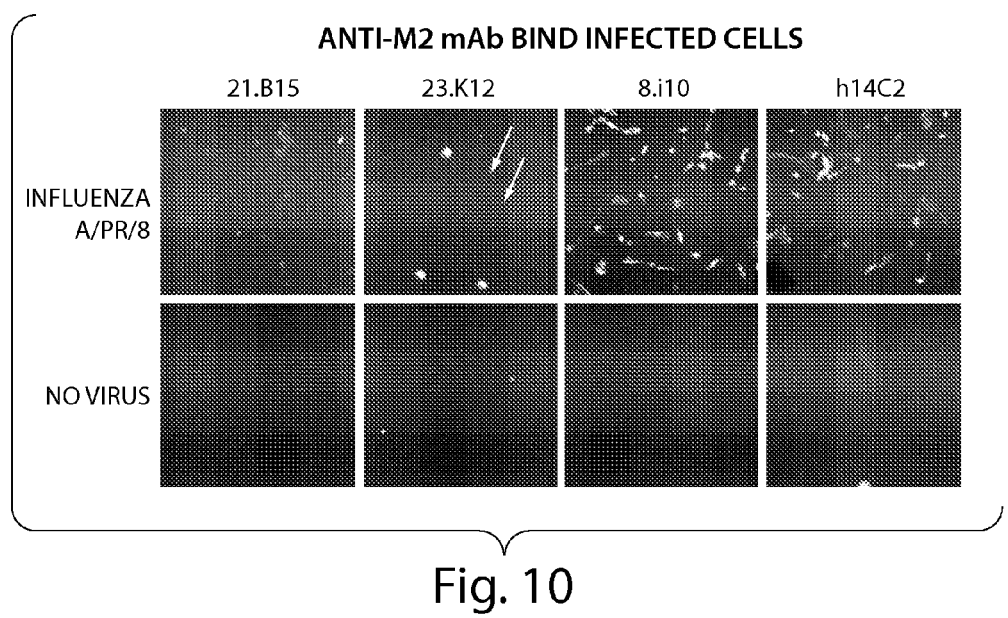
FIG. 10 is a series of photographs showing anti-M2 rHMAbs bound to cells infected with influenza. MDCK cells were or were not infected with influenza A/PR/8/32 and Ab binding from crude supernatant was tested 24 hours later. Data were gathered from the FMAT plate scanner.

Binding was also tested on MDCK cells infected with the PR8 virus (FIG. 10). The control antibody 14C2 and the three anti M2E clones: 8I10, 21B15 and 23K12, all showed specific binding to the M2 protein expressed on the surface of PR8-infected cells. No binding was observed on uninfected cells.

Figure 11:
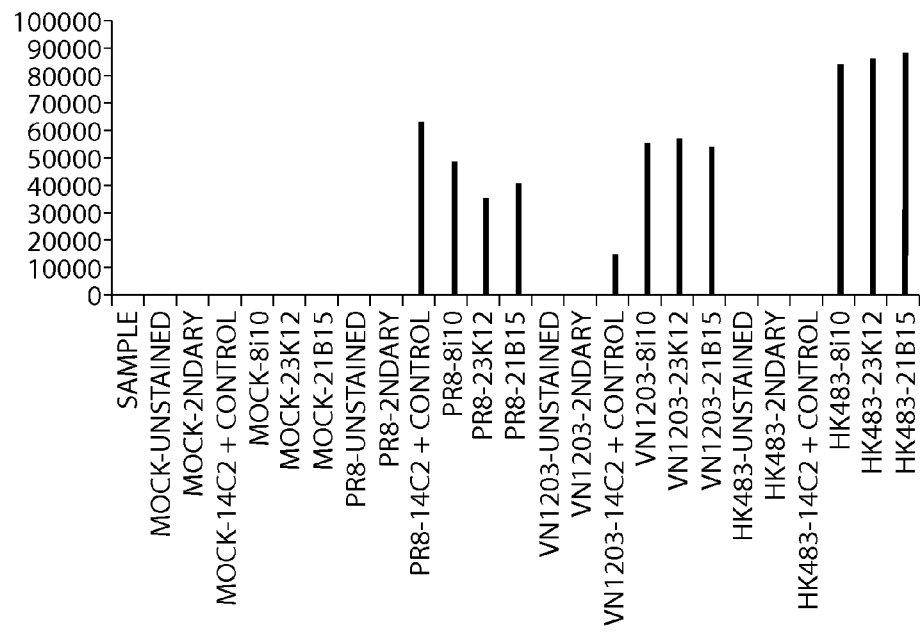
FIG. 11 is a graph showing anti-M2 rHMAb clones from crude supernatant bound to cells transfected with the influenza subtypes $H_3N2$, HK483, and VN1203 M2 proteins. Plasmids encoding full length M2 cDNAs corresponding to influenza strains H3N2, HK483, and VN1203, as well as a mock plasmid control, were transiently transfected into 293 cells. The 14C2, 8i10, 23K12, and 21B15 mABs were tested for binding to the transfectants, and were detected with an AF647-conjugated anti-human IgG secondary antibody. Shown are the mean fluorescence intensities of the specific mAB bound after FACS analysis.

The antibodies were purified over protein A columns from the supernatants. FACs analysis was performed using purified antibodies at a concentration of 1 ug per ml to examine the binding of the antibodies to transiently transfected 293 PEAK cells expressing the M2 proteins on the cell surface. Binding was measured testing binding to mock transfected cells and cells transiently transfected with the Influenza subtype H3N2, A/Vietnam/1203/2004 (VN1203), or A/Hong Kong/483/1997 HK483 M2 proteins. As a positive control the antibody 14C2 was used. Unstained and secondary antibody alone controls helped determined background. Specific staining for cells transfected with the M2 protein was observed for all three clones. Furthermore, all three clones bound to the high path strains A/Vietnam/1203/2004 and A/Hong Kong/483/1997 M2 proteins very well, whereas the positive control 14C2 which bound well to H3N2 M2 protein, bound much weaker to the A/Vietnam/1203/2004 M2 protein and did not bind the A/Hong Kong/483/1997 M2 protein. See FIG. 11.

Antibodies 21B15, 23K12, and 8I10 bound to the surface of 293-HEK cells stably expressing the M2 protein, but not to vector transfected cells (see FIG. 1). In addition, binding of these antibodies was not competed by the presence of 5 mg/ml 24-mer M2 peptide, whereas the binding of the control chimeric mouse V-region/human IgG1 kappa 14C2 antibody (hu14C2) generated against the linear M2 peptide was completely inhibited by the M2 peptide (see FIG. 1). These data confirm that these antibodies bind to conformational epitopes present in M2e expressed on the cell or virus surface, as opposed to the linear M2e peptide.

Example 5

Viral Binding of Human Anti-Influenza Monoclonal Antibodies

Figure 2A:
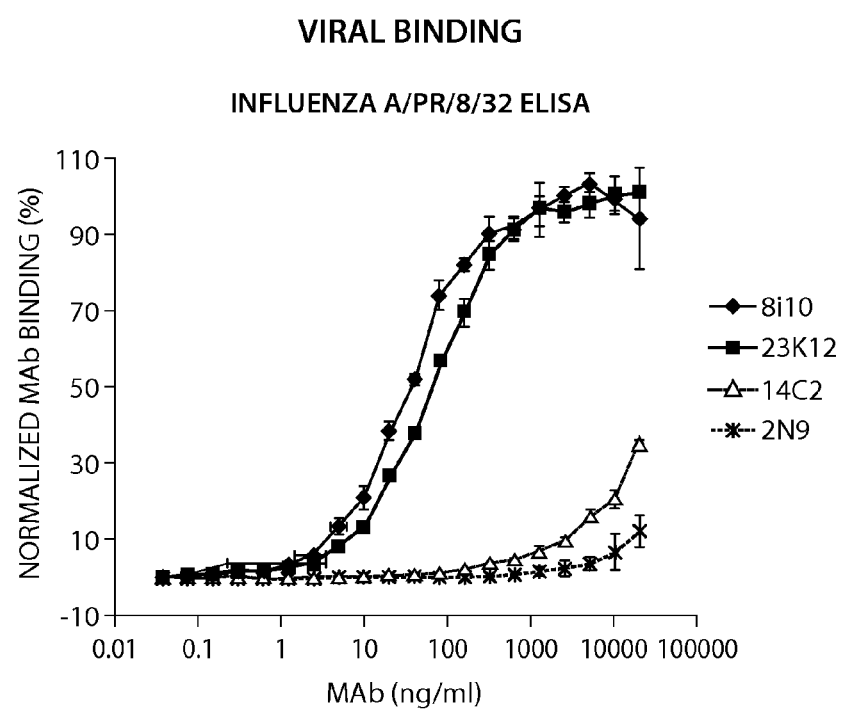
FIGS. 2A and B are graphs showing human monoclonal antibody binding to influenza A/Puerto Rico/8/32.
Figure 2B:
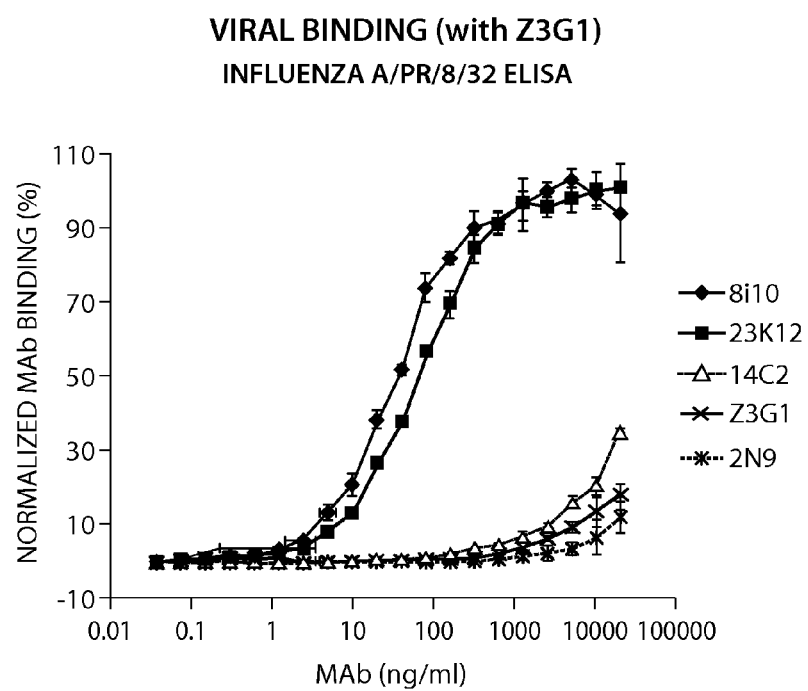

UV-inactivated influenza A virus (A/PR/8/34) (Applied Biotechnologies) was plated in 384-well MaxiSorp plates (Nunc) at 1.2 µg/ml in PBS, with 25 µl/well, and was incubated at 4° C. overnight. The plates were then washed three times with PBS, and blocked with 1% Nonfat dry milk in PBS, 50 µl/well, and then were incubated at room temp for 1 hr. After a second wash with PBS, MAbs were added at the indicated concentrations in triplicate, and the plates were incubated at room temp for 1 hour. After another wash with PBS, to each well was added 25 µl of a 1/5000 dilution of horseradish peroxidase (HRP) conjugated goat anti-human IgG Fc (Pierce) in PBS/1% Milk, and the plates were left at room temp for 1 hr. After the final PBS wash, the HRP substrate 1-Step™ Ultra-TMB-ELISA (Pierce) was added at 25 µl/well, and the reaction proceeded in the dark at room temp. The assay was stopped with 25 µl/well 1N $H_2SO_4$, and light absorbance at 450 nm (A450) was read on a SpectroMax Plus plate reader. Data are normalized to the absorbance of MAb 8I10 binding at 10 μg/ml. Results are shown in FIGS. 2A and 2B.

Example 6

Binding of Human Anti-Influenza Monoclonal Antibodies to Full-Length M2 Variants M2 variants (including those with a high pathology phenotype in vivo) were selected for analysis. See FIG. 3A for sequences.

Figures 1, 3B:
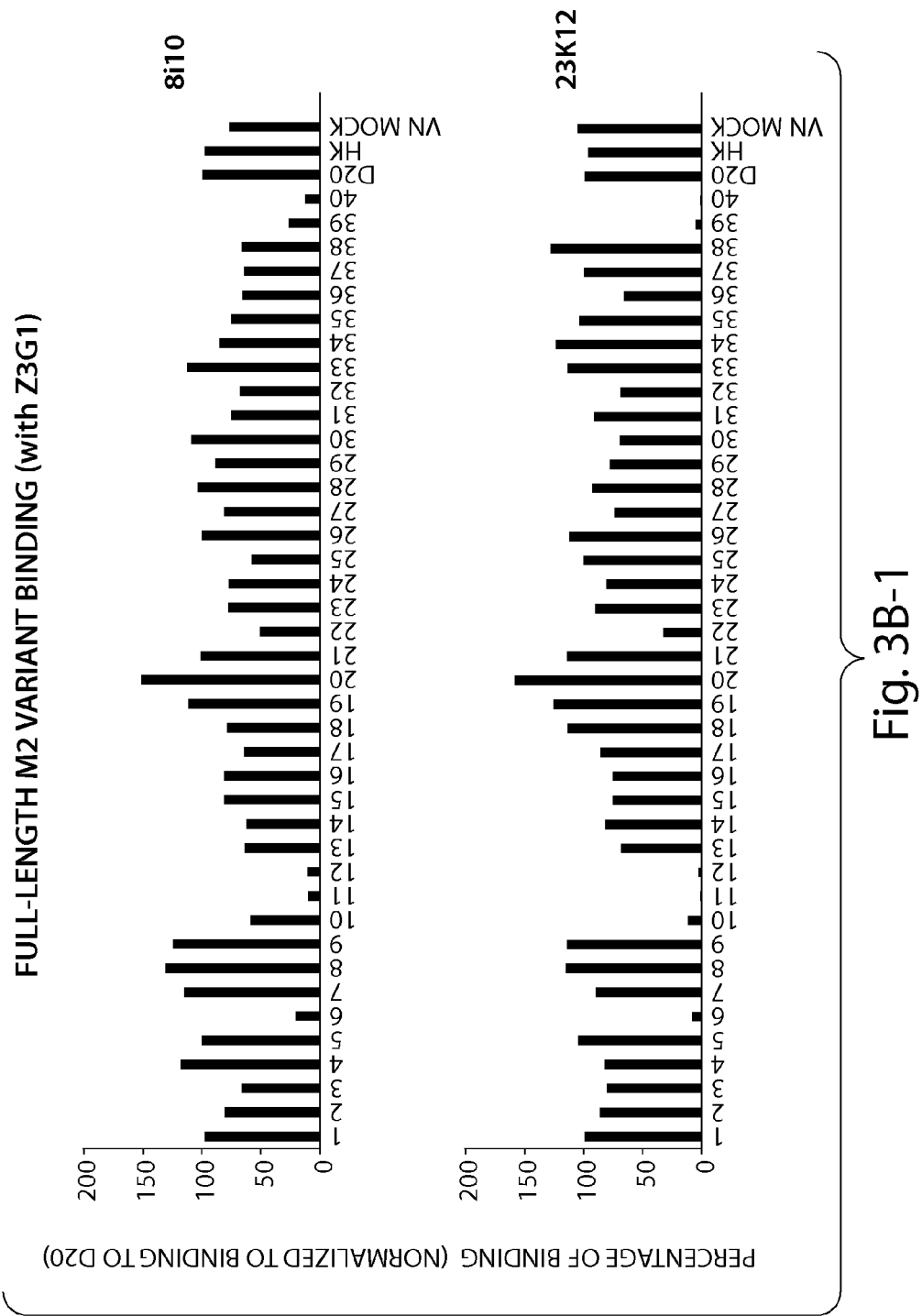
FIGS. 3B and C are bar charts showing binding of human monoclonal anti-influenza antibody binding to M2 variants shown in FIG. 3A.
Figures 2, 3B:
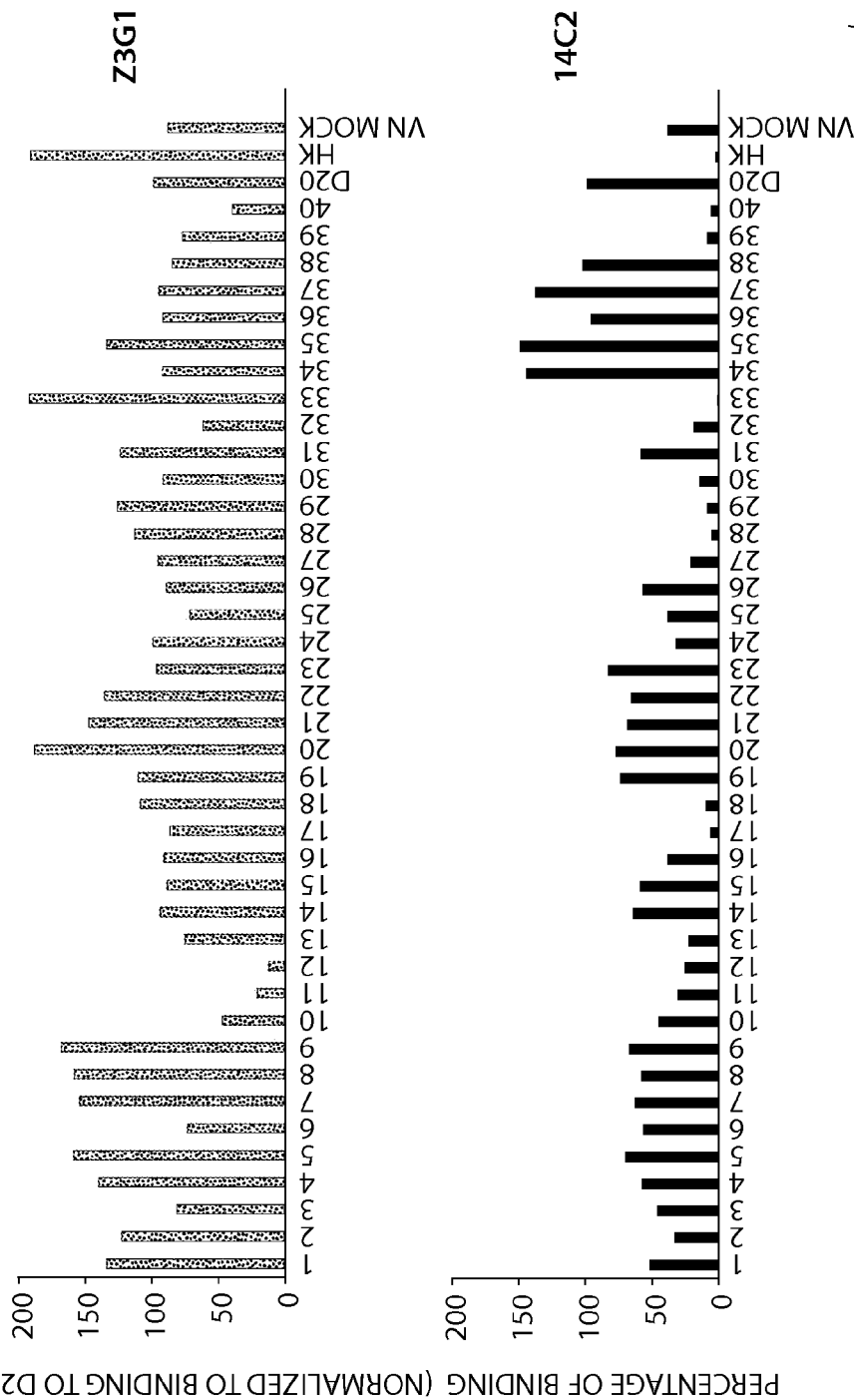
Figures 1, 3C:
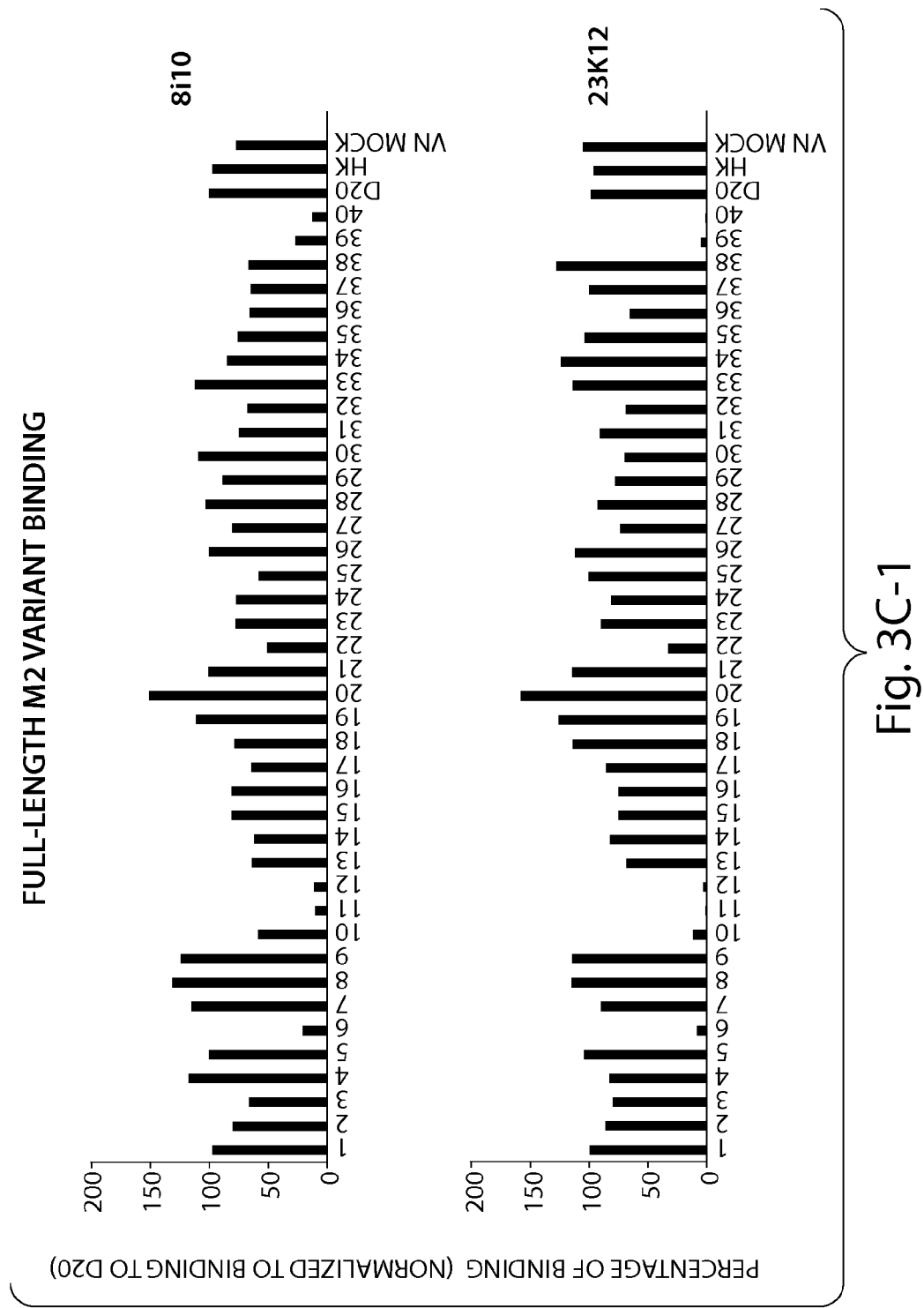
Figures 2, 3C:
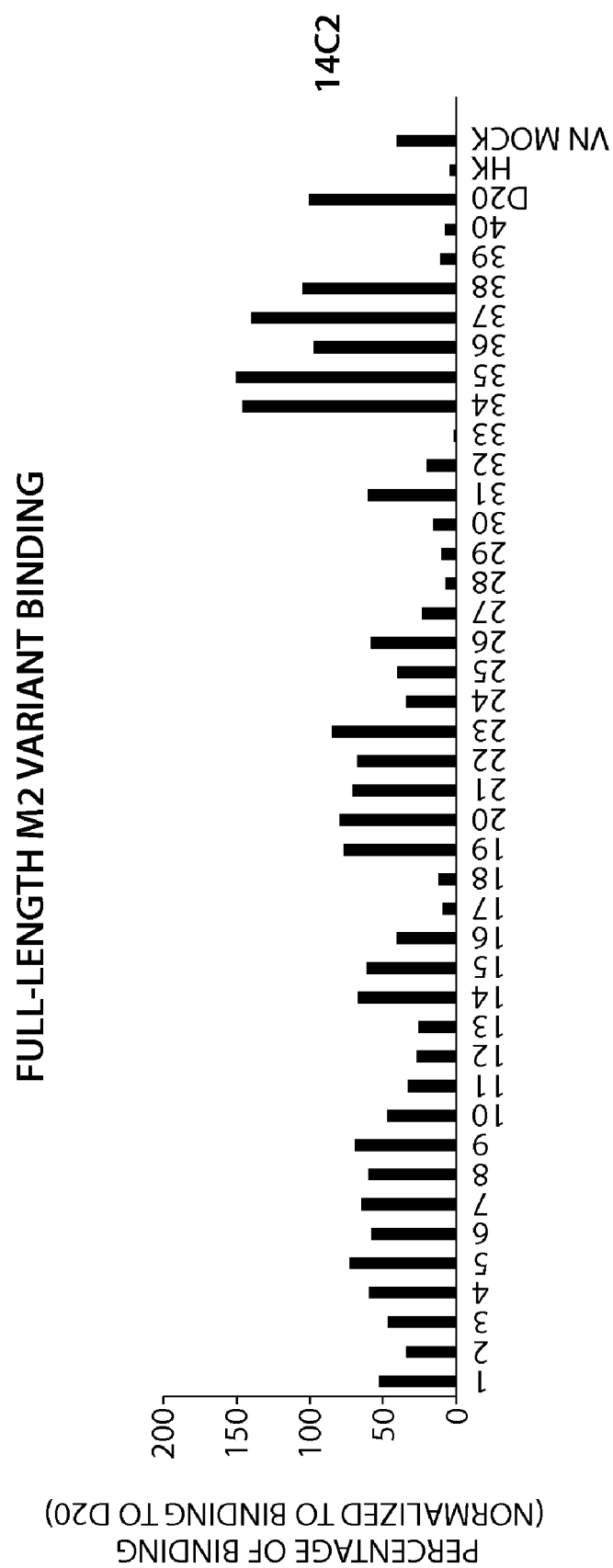
FIG. 3A is a chart showing amino acid sequences of extracellular domains of M2 variants (SEQ ID NOs 1-3, 115, and 5-40, respectively).

M2 cDNA constructs were transiently transfected in HEK293 cells and analyzed as follows: To analyze the transient transfectants by FACS, cells on 10 cm tissue culture plates were treated with 0.5 ml Cell Dissociation Buffer (Invitrogen), and harvested. Cells were washed in PBS containing 1% FBS, 0.2% $NaN_3$ (FACS buffer), and resuspended in 0.6 ml FACS buffer supplemented with 100 μg/ml rabbit IgG. Each transfectant was mixed with the indicated MAbs at 1 μg/ml in 0.2 ml FACS buffer, with $5 \times 10^5$ to $10^6$ cells per sample. Cells were washed three times with FACS buffer, and each sample was resuspended in 0.1 ml containing 1 μg/ml alexafluor (AF) 647-anti human IgG H&L (Invitrogen). Cells were again washed and flow cytometry was performed on a FACSCanto device (Becton-Dickenson). The data is expressed as a percentage of the mean fluorescence of the M2-D20 transient transfectant. Data for variant binding are representative of 2 experiments. Data for alanine mutants are average readouts from 3 separate experiments with standard error. Results are shown in FIGS. 3B and 3C.

Example 7

Alanine Scanning Mutagenesis to Evaluate M2 Binding

To evaluate the antibody binding sites, alanine was substituted at individual amino acid positions as indicated by site-directed mutagenesis.

Figure 4A:
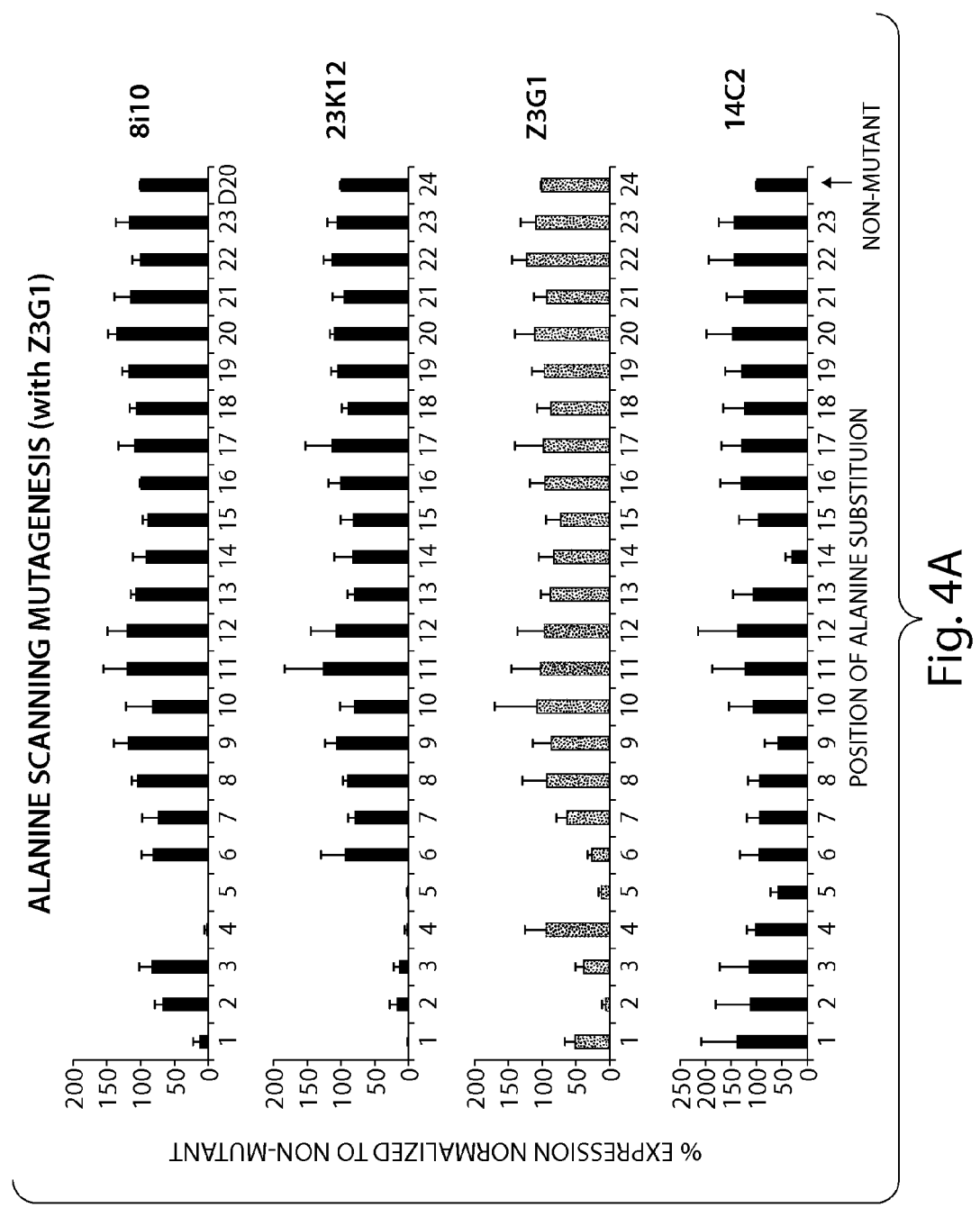
FIGS. 4A and B are bar charts showing binding of human monoclonal anti-influenza antibody binding to M2 peptides subjected to alanine scanning mutagenesis.
Figure 4B:
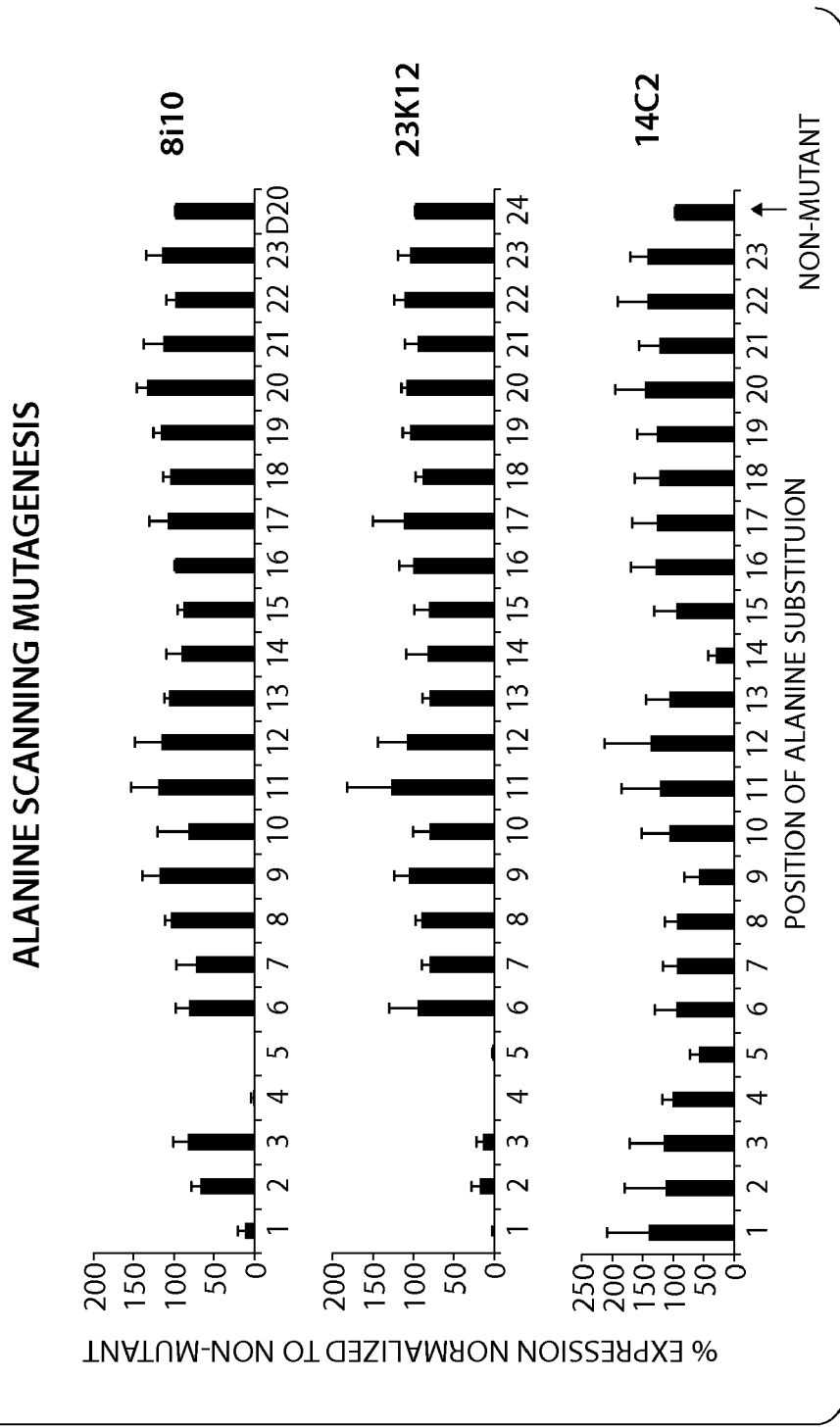

M2 cDNA constructs were transiently transfected in HEK293 cells and analyzed as described above in Example 6. Results are shown in FIGS. 4A and 4B. FIG. 8 shows that the epitope is in a highly conserved region of the amino terminus of the M2 polypeptide. As shown in FIGS. 4A, 4B and FIG. 8, the epitope includes the serine at position 2, the threonine at position 5 and the glutamic acid at position 6 of the M2 polypeptide.

Example 8

Epitope Blocking

Figure 5:
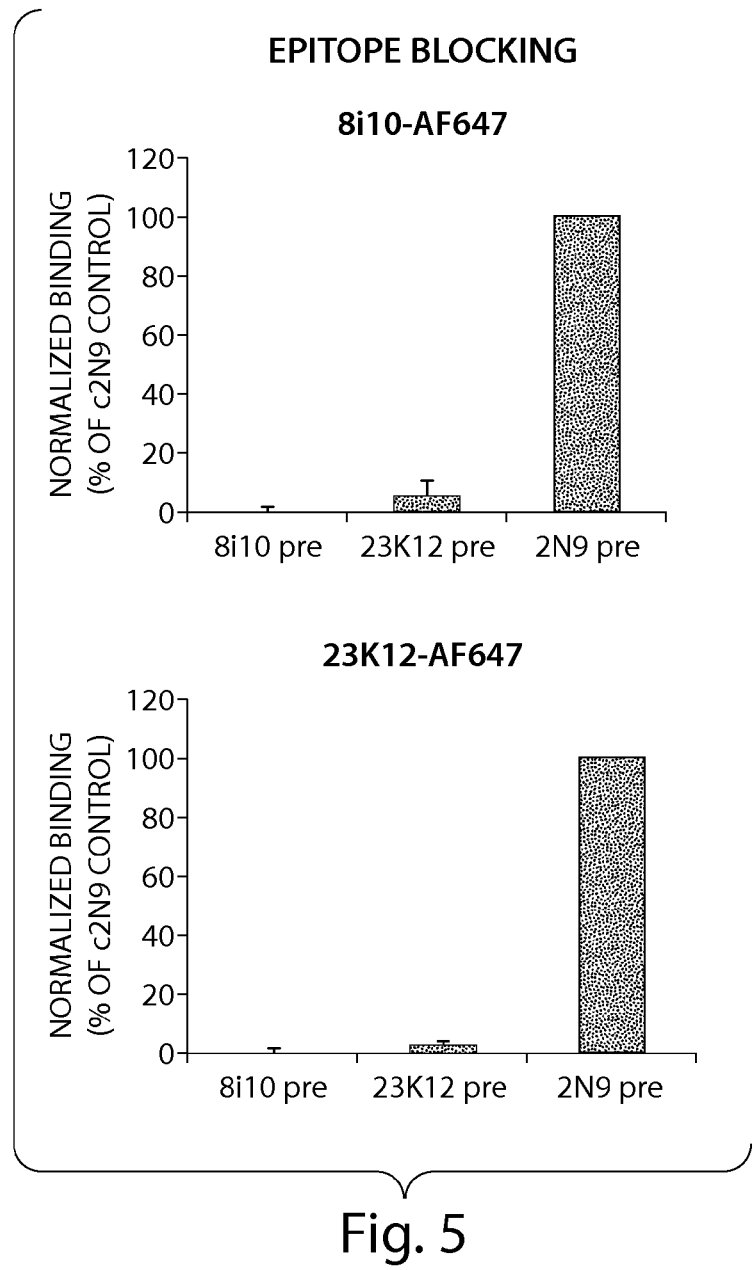
FIG. 5 is a series of bar charts showing binding of MAbs 8i10 and 23K12 to M2 protein representing influenza strain A/HK/483/1997 sequence that was stably expressed in the CHO cell line DG44.

To determine whether the MAbs 8I10 and 23K12 bind to the same site, M2 protein representing influenza strain A/HK/483/1997 sequence was stably expressed in the CHO (Chinese Hamster Ovary) cell line DG44. Cells were treated with Cell Dissociation Buffer (Invitrogen), and harvested. Cells were washed in PBS containing 1% FBS, 0.2% $NaN_3$ (FACS buffer), and resuspended at $10^7$ cells/ml in FACS buffer supplemented with 100 μg/ml rabbit IgG. The cells were pre-bound by either MAb (or the 2N9 control) at 10 μg/ml for 1 hr at 4° C., and were then washed with FACS buffer. Directly conjugated AF647-8I10 or -23K12 (labeled with the AlexaFluor® 647 Protein Labeling kit (Invitrogen) was then used to stain the three pre-blocked cell samples at 1 μg/ml for $10^6$ cells per sample. Flow cytometric analyses proceeded as before with the FACSCanto. Data are average readouts from 3 separate experiments with standard error. Results are shown in FIG. 5.

Example 9

Binding of Human Anti-Influenza Monoclonal Antibodies to M2 Variants and Truncated M2 Peptides The cross reactivity of mAbs 8i10 and 23K12 to other M2 peptide variants was assessed by ELISA. Peptide sequences are shown in FIGS. 6A and 6B. Additionally, a similar ELISA assay was used to determine binding activity to M2 truncated peptides.

In brief, each peptide was coated at 2 μg/mL to a flat bottom 384 well plate (Nunc) in 25 μL/well of PBS buffer overnight at 4° C. Plates were washed three times and blocked with 1% Milk/PBS for one hour at room temperature. After washing three times, MAb titers were added and incubated for one hour at room temperature. Diluted HRP conjugated goat anti-human immunoglobulin FC specific (Pierce) was added to each well after washing three times. Plates were incubated for one hour at room temperature and washed three times. 1-Step™ Ultra-TMB-ELISA (Pierce) was added at 25 μl/well, and the reaction proceeded in the dark at room temp. The assay was stopped with 25 μl/well 1N $H_2SO_4$, and light absorbance at 450 nm (A450) was read on a SpectroMax Plus plate reader. Results are shown in FIGS. 6A and 6B.

Example 10

In Vivo Evaluation of the Ability of Human Anti-Influenza Monoclonal Antibodies to Protect from Lethal Viral Challenge The ability of antibodies, 23K12 and 8I10, to protect mice from lethal viral challenge with a high path avian influenza strain was tested.

Figure 7:
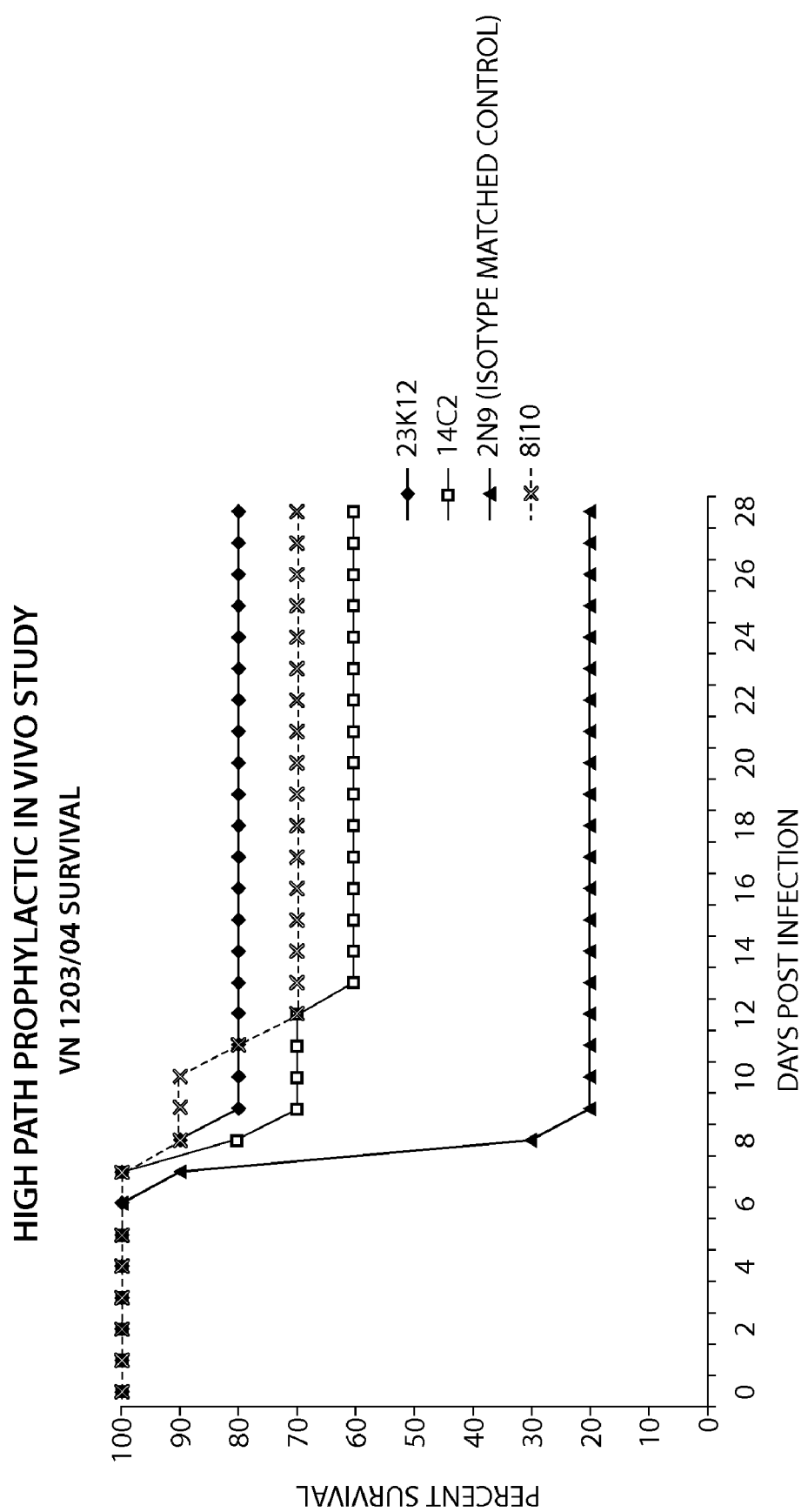
FIG. 7 is a graph showing survival of influenza infected mice treated with human anti-influenza monoclonal antibodies.

Female BALB/c mice were randomized into 5 groups of 10. One day prior (Day −1 (minus one)) and two days post infection (Day +2 (plus two)), 200 ug of antibody was given via 200 ul intra-peritoneal injection. On Day 0 (zero), an approximate LD90 (lethal dose 90) of A/Vietnam/1203/04 influenza virus, in a volume of 30 μl was given intra-nasally. Survival rate was observed from Day 1 through Day 28 post-infection. Results are shown in FIG. 7.

Other Embodiments

Although specific embodiments of the invention have been described herein for purposes of illustration, various modifications may be made without deviating from the spirit and scope of the invention. Accordingly, the invention is not limited except as by the appended claims.

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof,

What is claimed:

1. An isolated fully human monoclonal antibody, wherein said monoclonal antibody has the following characteristics
   a) binds to an epitope in the extracellular domain of the matrix 2 ectodomain (M2e) polypeptide of an influenza A virus;
   b) binds to influenza A infected cells; and
   c) binds to influenza A virus, and wherein said antibody comprises a $V_H$CDR1 comprising the amino acid sequence of SNYMS (SEQ ID NO: 103); a $V_H$ CDR2 region comprising amino acid sequence of VIYSGGSTYYADSVK (SEQ ID NO: 105), a $V_H$ CDR3 region comprising the amino acid sequence of CLSRMRGYGLDV (SEQ ID NO: 107); a $V_L$ CDR1 region comprising the amino acid sequence of RTSQSISSYLN (SEQ ID NO: 92); a $V_L$ CDR2 region comprising the amino acid sequence of AASSLQSGVPSRF (SEQ ID NO: 94); and a $V_L$ CDR3 region comprising the amino acid sequence of QQSYSMPA (SEQ ID NO: 96).

2. An isolated anti-matrix 2 ectodomain (M2e) antibody, wherein said antibody comprises a $V_H$CDR1 region comprising the amino acid sequence of SNYMS (SEQ ID NO: 103); a $V_H$ CDR2 region comprising the amino acid sequence of VIYSGGSTYYADSVK (SEQ ID NO: 105), a $V_H$ CDR3 region comprising the amino acid sequence of CLSRMRGYGLDV (SEQ ID NO: 107); a $V_L$ CDR1 region comprising the amino acid sequence of RTSQSISSYLN (SEQ ID NO: 92); a $V_L$ CDR2 region comprising the amino acid sequence of AASSLQSGVPSRF (SEQ ID NO: 94); and a $V_L$ CDR3 region comprising the amino acid sequence of QQSYSMPA (SEQ ID NO: 96); wherein the M2e is of an influenza A virus.

3. An isolated fully human monoclonal anti-matrix 2 ectodomain (M2e) antibody comprising
   a heavy chain sequence comprising the amino acid sequence of SEQ ID NO: 50 and a light chain sequence comprising the amino acid sequence SEQ ID NO: 52; wherein the M2e is of an influenza A virus.

4. A composition comprising the antibody of claim 1.

5. The composition of claim 4, further comprising an anti-viral drug, a viral entry inhibitor or a viral attachment inhibitor.

6. The composition of claim 5, wherein said anti-viral drug is a neuraminidase inhibitor, a HA inhibitor, a sialic acid inhibitor or an M2 ion channel inhibitor.

7. The composition of claim 6, wherein said neuraminidase inhibitor is zanamivir, or oseltamivir phosphate.

8. The composition of claim 4, further comprising a second anti-influenza A antibody.

9. The antibody of claim 1, wherein said antibody is operably-linked to a therapeutic agent or a detectable label.

10. A diagnostic kit comprising the antibody according to claim 1.

* * * * *

SEQUENCE LISTING

<160> NUMBER OF SEQ ID NOS: 166

<210> SEQ ID NO 1
<211> LENGTH: 24
<212> TYPE: PRT
<213> ORGANISM: Influenza A virus

<400> SEQUENCE: 1

Met Ser Leu Leu Thr Glu Val Glu Thr Pro Thr Arg Asn Glu Trp Gly
1               5                   10                  15

Cys Arg Cys Asn Asp Ser Ser Asp
            20

<210> SEQ ID NO 2
<211> LENGTH: 24
<212> TYPE: PRT
<213> ORGANISM: Influenza A virus

<400> SEQUENCE: 2

Met Ser Leu Leu Thr Glu Val Glu Thr Pro Thr Lys Asn Glu Trp Glu
1               5                   10                  15

Cys Arg Cys Asn Asp Ser Ser Asp
            20

<210> SEQ ID NO 3
<211> LENGTH: 24
<212> TYPE: PRT
<213> ORGANISM: Influenza A virus

<400> SEQUENCE: 3

Met Ser Leu Leu Thr Glu Val Glu Thr Pro Ile Arg Asn Glu Trp Glu
1               5                   10                  15

Cys Arg Cys Asn Asp Ser Ser Asp
            20

<210> SEQ ID NO 4
<211> LENGTH: 24
<212> TYPE: PRT
<213> ORGANISM: Influenza A virus

<400> SEQUENCE: 4

Met Ser Leu Leu Thr Glu Val Glu Thr Pro Ile Arg Asn Gly Trp Glu
1               5                   10                  15

Cys Lys Cys Asn Asp Ser Ser Asp
            20

<210> SEQ ID NO 5
<211> LENGTH: 24
<212> TYPE: PRT
<213> ORGANISM: Influenza A virus

<400> SEQUENCE: 5

Met Ser Leu Leu Thr Glu Val Glu Thr Pro Ile Arg Ser Glu Trp Gly
1               5                   10                  15

Cys Arg Cys Asn Asp Ser Ser Asp
            20

<210> SEQ ID NO 6
<211> LENGTH: 24

```
<212> TYPE: PRT
<213> ORGANISM: Influenza A virus

<400> SEQUENCE: 6

Met Ser Phe Leu Pro Glu Val Glu Thr Pro Ile Arg Asn Glu Trp Gly
1               5                   10                  15

Cys Arg Cys Asn Asp Ser Ser Asp
            20

<210> SEQ ID NO 7
<211> LENGTH: 24
<212> TYPE: PRT
<213> ORGANISM: Influenza A virus

<400> SEQUENCE: 7

Met Ser Leu Leu Thr Glu Val Glu Thr Pro Ile Arg Asn Glu Trp Gly
1               5                   10                  15

Cys Arg Cys Asn Asp Ser Ser Asn
            20

<210> SEQ ID NO 8
<211> LENGTH: 24
<212> TYPE: PRT
<213> ORGANISM: Influenza A virus

<400> SEQUENCE: 8

Met Ser Leu Leu Thr Glu Val Glu Thr Pro Ile Arg Lys Glu Trp Gly
1               5                   10                  15

Cys Arg Cys Asn Asp Ser Ser Asp
            20

<210> SEQ ID NO 9
<211> LENGTH: 24
<212> TYPE: PRT
<213> ORGANISM: Influenza A virus

<400> SEQUENCE: 9

Met Ser Phe Leu Thr Glu Val Glu Thr Pro Ile Arg Asn Glu Trp Gly
1               5                   10                  15

Cys Arg Cys Asn Asp Ser Ser Asp
            20

<210> SEQ ID NO 10
<211> LENGTH: 24
<212> TYPE: PRT
<213> ORGANISM: Influenza A virus

<400> SEQUENCE: 10

Met Ser Leu Pro Thr Glu Val Glu Thr Pro Ile Arg Ser Glu Trp Gly
1               5                   10                  15

Cys Arg Cys Asn Asp Ser Ser Asp
            20

<210> SEQ ID NO 11
<211> LENGTH: 24
<212> TYPE: PRT
<213> ORGANISM: Influenza A virus

<400> SEQUENCE: 11

Met Ser Leu Leu Pro Glu Val Glu Thr Pro Ile Arg Asn Glu Trp Gly
1               5                   10                  15

Cys Arg Cys Asn Asp Ser Ser Asp
            20
```

```
<210> SEQ ID NO 12
<211> LENGTH: 24
<212> TYPE: PRT
<213> ORGANISM: Influenza A virus

<400> SEQUENCE: 12

Met Ser Leu Leu Pro Glu Val Glu Thr Pro Ile Arg Asn Gly Trp Gly
1               5                   10                  15

Cys Arg Cys Asn Asp Ser Ser Asp
            20

<210> SEQ ID NO 13
<211> LENGTH: 24
<212> TYPE: PRT
<213> ORGANISM: Influenza A virus

<400> SEQUENCE: 13

Met Ser Leu Leu Thr Glu Val Glu Thr Pro Thr Arg Asn Gly Trp Glu
1               5                   10                  15

Cys Arg Cys Ser Gly Ser Ser Asp
            20

<210> SEQ ID NO 14
<211> LENGTH: 24
<212> TYPE: PRT
<213> ORGANISM: Influenza A virus

<400> SEQUENCE: 14

Met Ser Leu Leu Thr Glu Val Glu Thr Pro Ile Arg Asn Glu Trp Glu
1               5                   10                  15

Tyr Arg Cys Asn Asp Ser Ser Asp
            20

<210> SEQ ID NO 15
<211> LENGTH: 24
<212> TYPE: PRT
<213> ORGANISM: Influenza A virus

<400> SEQUENCE: 15

Met Ser Leu Leu Thr Glu Val Glu Thr Pro Ile Arg Asn Glu Trp Glu
1               5                   10                  15

Tyr Arg Cys Ser Asp Ser Ser Asp
            20

<210> SEQ ID NO 16
<211> LENGTH: 24
<212> TYPE: PRT
<213> ORGANISM: Influenza A virus

<400> SEQUENCE: 16

Met Ser Leu Leu Thr Glu Val Glu Thr Pro Thr Arg Asn Gly Trp Glu
1               5                   10                  15

Cys Arg Tyr Ser Asp Ser Ser Asp
            20

<210> SEQ ID NO 17
<211> LENGTH: 24
<212> TYPE: PRT
<213> ORGANISM: Influenza A virus

<400> SEQUENCE: 17

Met Ser Phe Leu Thr Glu Val Glu Thr Leu Thr Arg Asn Gly Trp Glu
```

```
                1               5                   10                  15
Cys Arg Cys Ser Asp Ser Ser Asp
            20

<210> SEQ ID NO 18
<211> LENGTH: 24
<212> TYPE: PRT
<213> ORGANISM: Influenza A virus

<400> SEQUENCE: 18

Met Ser Leu Leu Thr Glu Val Glu Thr Leu Thr Arg Asn Gly Trp Glu
1               5                   10                  15

Cys Lys Cys Arg Asp Ser Ser Asp
            20

<210> SEQ ID NO 19
<211> LENGTH: 24
<212> TYPE: PRT
<213> ORGANISM: Influenza A virus

<400> SEQUENCE: 19

Met Ser Leu Leu Thr Glu Val Glu Thr Pro Ile Arg Asn Glu Trp Gly
1               5                   10                  15

Cys Arg Cys Asn Asp Ser Ser Asp
            20

<210> SEQ ID NO 20
<211> LENGTH: 24
<212> TYPE: PRT
<213> ORGANISM: Influenza A virus

<400> SEQUENCE: 20

Met Ser Leu Leu Thr Glu Val Glu Thr Pro Ile Arg Ser Glu Trp Gly
1               5                   10                  15

Cys Arg Cys Asn Asp Ser Gly Asp
            20

<210> SEQ ID NO 21
<211> LENGTH: 24
<212> TYPE: PRT
<213> ORGANISM: Influenza A virus

<400> SEQUENCE: 21

Met Ser Leu Leu Thr Glu Val Glu Thr Pro Ile Arg Asn Glu Trp Glu
1               5                   10                  15

Cys Arg Cys Asn Gly Ser Ser Asp
            20

<210> SEQ ID NO 22
<211> LENGTH: 24
<212> TYPE: PRT
<213> ORGANISM: Influenza A virus

<400> SEQUENCE: 22

Met Ser Leu Pro Thr Glu Val Glu Thr Pro Ile Arg Asn Glu Trp Gly
1               5                   10                  15

Cys Arg Cys Asn Asp Ser Ser Asp
            20

<210> SEQ ID NO 23
<211> LENGTH: 24
<212> TYPE: PRT
<213> ORGANISM: Influenza A virus
```

-continued

<400> SEQUENCE: 23

Met Ser Leu Leu Thr Glu Val Glu Thr Pro Ile Arg Asn Glu Trp Gly
1               5                   10                  15

Cys Arg Cys Asn Gly Ser Ser Asp
            20

<210> SEQ ID NO 24
<211> LENGTH: 24
<212> TYPE: PRT
<213> ORGANISM: Influenza A virus

<400> SEQUENCE: 24

Met Ser Leu Leu Thr Glu Val Asp Thr Leu Thr Arg Asn Gly Trp Gly
1               5                   10                  15

Cys Arg Cys Ser Asp Ser Ser Asp
            20

<210> SEQ ID NO 25
<211> LENGTH: 24
<212> TYPE: PRT
<213> ORGANISM: Influenza A virus

<400> SEQUENCE: 25

Met Ser Leu Leu Thr Glu Val Glu Thr Leu Thr Lys Asn Gly Trp Gly
1               5                   10 15

Cys Arg Cys Ser Asp Ser Ser Asp
20

<210> SEQ ID NO 26
<211> LENGTH: 24
<212> TYPE: PRT
<213> ORGANISM: Influenza A virus

<400> SEQUENCE: 26

Met Ser Leu Leu Thr Glu Val Glu Thr Pro Thr Arg Asn Gly Trp Glu
1 5 10 15

Cys Lys Cys Ser Asp Ser Ser Asp
20

<210> SEQ ID NO 27
<211> LENGTH: 24
<212> TYPE: PRT
<213> ORGANISM: Influenza A virus

<400> SEQUENCE: 27

Met Ser Leu Leu Thr Glu Val Glu Thr His Thr Arg Asn Gly Trp Glu
1 5 10 15

Cys Lys Cys Ser Asp Ser Ser Asp
20

<210> SEQ ID NO 28
<211> LENGTH: 24
<212> TYPE: PRT
<213> ORGANISM: Influenza A virus

<400> SEQUENCE: 28

Met Ser Leu Leu Thr Glu Val Lys Thr Pro Thr Arg Asn Gly Trp Glu
1 5 10 15

Cys Lys Cys Ser Asp Ser Ser Asp
20

```
<210> SEQ ID NO 29
<211> LENGTH: 24
<212> TYPE: PRT
<213> ORGANISM: Influenza A virus

<400> SEQUENCE: 29

Met Ser Leu Leu Thr Glu Val Glu Thr Leu Thr Arg Asn Gly Trp Gly
1               5                   10                  15

Cys Arg Cys Ser Asp Ser Ser Asp
            20

<210> SEQ ID NO 30
<211> LENGTH: 24
<212> TYPE: PRT
<213> ORGANISM: Influenza A virus

<400> SEQUENCE: 30

Met Ser Leu Leu Thr Glu Val Glu Thr Pro Thr Arg Asp Gly Trp Glu
1               5                   10                  15

Cys Lys Cys Ser Asp Ser Ser Asp
            20

<210> SEQ ID NO 31
<211> LENGTH: 24
<212> TYPE: PRT
<213> ORGANISM: Influenza A virus

<400> SEQUENCE: 31

Met Ser Leu Leu Thr Glu Val Glu Thr Pro Thr Arg Asn Gly Trp Gly
1               5                   10                  15

Cys Arg Cys Ser Asp Ser Ser Asp
            20

<210> SEQ ID NO 32
<211> LENGTH: 24
<212> TYPE: PRT
<213> ORGANISM: Influenza A virus

<400> SEQUENCE: 32

Met Ser Leu Leu Thr Glu Val Glu Thr Pro Thr Arg Asn Gly Trp Glu
1               5                   10                  15

Cys Lys Cys Asn Asp Ser Ser Asp
            20

<210> SEQ ID NO 33
<211> LENGTH: 24
<212> TYPE: PRT
<213> ORGANISM: Influenza A virus

<400> SEQUENCE: 33

Met Ser Leu Leu Thr Glu Val Glu Thr Leu Thr Arg Asn Gly Trp Glu
1               5                   10                  15

Cys Lys Cys Ser Asp Ser Ser Asp
            20

<210> SEQ ID NO 34
<211> LENGTH: 24
<212> TYPE: PRT
<213> ORGANISM: Influenza A virus

<400> SEQUENCE: 34

Met Ser Leu Leu Thr Glu Val Glu Thr Pro Ile Arg Asn Glu Trp Gly
1               5                   10                  15
```

Cys Lys Cys Asn Asp Ser Ser Asp
            20

<210> SEQ ID NO 35
<211> LENGTH: 24
<212> TYPE: PRT
<213> ORGANISM: Influenza A virus

<400> SEQUENCE: 35

Met Ser Phe Leu Thr Glu Val Glu Thr Pro Ile Arg Asn Glu Trp Gly
1               5                   10                  15

Cys Arg Cys Asn Gly Ser Ser Asp
            20

<210> SEQ ID NO 36
<211> LENGTH: 24
<212> TYPE: PRT
<213> ORGANISM: Influenza A virus

<400> SEQUENCE: 36

Met Ser Leu Leu Thr Glu Val Glu Thr Pro Thr Arg Asn Gly Trp Glu
1               5                   10                  15

Cys Arg Cys Asn Asp Ser Ser Asp
            20

<210> SEQ ID NO 37
<211> LENGTH: 24
<212> TYPE: PRT
<213> ORGANISM: Influenza A virus

<400> SEQUENCE: 37

Met Ser Leu Leu Thr Glu Val Glu Thr Pro Ile Arg Lys Gly Trp Glu
1               5                   10                  15

Cys Asn Cys Ser Asp Ser Ser Asp
            20

<210> SEQ ID NO 38
<211> LENGTH: 24
<212> TYPE: PRT
<213> ORGANISM: Influenza A virus

<400> SEQUENCE: 38

Met Ser Leu Leu Thr Glu Val Glu Thr Pro Thr Arg Asn Glu Trp Glu
1               5                   10                  15

Cys Arg Cys Ser Asp Ser Ser Asp
            20

<210> SEQ ID NO 39
<211> LENGTH: 24
<212> TYPE: PRT
<213> ORGANISM: Influenza A virus

<400> SEQUENCE: 39

Met Ser Leu Leu Thr Gly Val Glu Thr His Thr Arg Asn Gly Trp Gly
1               5                   10                  15

Cys Lys Cys Ser Asp Ser Ser Asp
            20

<210> SEQ ID NO 40
<211> LENGTH: 24
<212> TYPE: PRT
<213> ORGANISM: Influenza A virus

<400> SEQUENCE: 40

```
Met Ser Leu Leu Pro Glu Val Glu Thr His Thr Arg Asn Gly Trp Gly
1               5                   10                  15

Cys Arg Cys Ser Asp Ser Ser Asp
            20
```

<210> SEQ ID NO 41
<211> LENGTH: 8
<212> TYPE: PRT
<213> ORGANISM: Influenza A virus

<400> SEQUENCE: 41

```
Ser Leu Leu Thr Glu Val Glu Thr
1               5
```

<210> SEQ ID NO 42
<211> LENGTH: 6
<212> TYPE: PRT
<213> ORGANISM: Influenza A virus

<400> SEQUENCE: 42

```
Ser Leu Leu Thr Glu Val
1               5
```

<210> SEQ ID NO 43
<211> LENGTH: 357
<212> TYPE: DNA
<213> ORGANISM: Homo sapiens

<400> SEQUENCE: 43

```
caggtgcaat tgcaggagtc gggcccagga ctggtgaagc cttcggagac cctgtccctc    60
acctgcactg tctctggttc gtccatcagt aattactact ggagctggat ccggcagtcc   120
ccagggaagg gactggagtg gattgggttt atctattacg gtggaaacac caagtacaat   180
ccctccctca gagccgcgt caccatatca caagacactt ccaagagtca ggtctccctg   240
acgatgagct ctgtgaccgc tgcggaatcg gccgtctatt tctgtgcgag agcgtcttgt   300
agtggtggtt actgtatcct tgactactgg ggccagggaa ccctggtcac cgtctcg     357
```

<210> SEQ ID NO 44
<211> LENGTH: 119
<212> TYPE: PRT
<213> ORGANISM: Homo sapiens

<400> SEQUENCE: 44

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Ser Ser Ile Ser Asn Tyr
            20                  25                  30

Tyr Trp Ser Trp Ile Arg Gln Ser Pro Gly Lys Gly Leu Glu Trp Ile
        35                  40                  45

Gly Phe Ile Tyr Tyr Gly Gly Asn Thr Lys Tyr Asn Pro Ser Leu Lys
    50                  55                  60

Ser Arg Val Thr Ile Ser Gln Asp Thr Ser Lys Ser Gln Val Ser Leu
65                  70                  75                  80

Thr Met Ser Ser Val Thr Ala Ala Glu Ser Ala Val Tyr Phe Cys Ala
                85                  90                  95

Arg Ala Ser Cys Ser Gly Gly Tyr Cys Ile Leu Asp Tyr Trp Gly Gln
            100                 105                 110

Gly Thr Leu Val Thr Val Ser
            115
```

<210> SEQ ID NO 45
<211> LENGTH: 322
<212> TYPE: DNA
<213> ORGANISM: Homo sapiens

<400> SEQUENCE: 45
gacatccaga tgacccagtc tccatcctcc ctgtctgcat ctgtaggaga cagagtcacc      60
atcacttgcc gggcgagtca gaacatttac aagtatttaa attggtatca gcagagacca     120
gggaaagccc ctaagggcct gatctctgct catccgggt tgcaaagtgg ggtcccatca     180
aggttcagtg gcagtggatc tgggacagat ttcactctca ccatcaccag tctgcaacct    240
gaagattttg caacttacta ctgtcaacag agttacagtc ccctctcac tttcggcgga     300 gggaccaggg tggagatcaa ac                                             322

<210> SEQ ID NO 46
<211> LENGTH: 107
<212> TYPE: PRT
<213> ORGANISM: Homo sapiens

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Tyr Lys Tyr
            20                  25                  30

Leu Asn Trp Tyr Gln Gln Arg Pro Gly Lys Ala Pro Lys Gly Leu Ile
        35                  40                  45

Ser Ala Ala Ser Gly Leu Gln Ser Gly Val Pro Ser Arg Phe Ser Gly
    50                  55                  60

Ser Gly Ser Gly Thr Asp Phe Thr Leu Thr Ile Thr Ser Leu Gln Pro
65                  70                  75                  80

Glu Asp Phe Ala Thr Tyr Tyr Cys Gln Gln Ser Tyr Ser Pro Pro Leu
                85                  90                  95

Thr Phe Gly Gly Gly Thr Arg Val Glu Ile Lys
            100                 105

<210> SEQ ID NO 47
<211> LENGTH: 357
<212> TYPE: DNA
<213> ORGANISM: Homo sapiens

<400> SEQUENCE: 47
caggtgcaat tgcaggagtc gggcccagga ctggtgaagc cttcggagac cctgtccctc      60
acctgcactg tctctggttc gtccatcagt aattactact ggagctggat ccggcagtcc     120
ccagggaagg gactggagtg gattgggttt atctattacg gtggaaacac caagtacaat     180
ccctccctca gagccgcgt caccatatca caagacactt ccaagagtca ggtcccctg       240 acgatgagct ctgtgaccgc tgcggaatcg ccgtctatt tctgtgcgag agcgtcttgt     300
agtggtggtt actgtatcct tgactactgg ggccaggga ccctggtcac cgtctcg        357

<210> SEQ ID NO 48
<211> LENGTH: 322
<212> TYPE: DNA
<213> ORGANISM: Homo sapiens

<400> SEQUENCE: 48
gacatccagg tgacccagtc tccatcctcc ctgtctgcat ctgtaggaga cagagtcacc      60

```
atcacttgcc gcgcgagtca gaacatttac aagtatttaa attggtatca gcagagacca      120
gggaaagccc ctaagggcct gatctctgct gcatccgggt tgcaaagtgg ggtcccatca      180
aggttcagtg gcagtggatc tgggacagat ttcactctca ccatcaccag tctgcaacct      240
gaagattttg caacttacta ctgtcaacag agttacagtc cccctctcac tttcggcgga      300
gggaccaggg tggatatcaa ac                                               322
```

```
<210> SEQ ID NO 49
<211> LENGTH: 357
<212> TYPE: DNA
<213> ORGANISM: Homo sapiens

<400> SEQUENCE: 49
gaggtgcagc tggtggagtc tgggggaggc ttggtccagc ctgggggtgtc cctgagaatc      60 tcctgtgcag cctctggatt caccgtcagt agcaactaca tgagttgggt ccgccaggct     120
ccagggaagg gctggagtg gtctcagtt atttatagtg gtggtagcac atactacgca       180
gactccgtga agggcagatt ctccttctcc agagacaact ccaagaacac agtgtttctt     240
caaatgaaca gcctgagagc cgaggacacg gctgtgtatt actgtgcgag atgtctgagc     300
aggatgcggg gttacggttt agacgtctgg ggccaaggga ccacggtcac cgtctcg       357
```

```
<210> SEQ ID NO 50
<211> LENGTH: 119
<212> TYPE: PRT
<213> ORGANISM: Homo sapiens

<400> SEQUENCE: 50

Glu Val Gln Leu Val Glu Ser Gly Gly Gly Leu Val Gln Pro Gly Gly
1               5                   10                  15

Ser Leu Arg Ile Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Ser Phe Ser Arg Asp Asn Ser Lys Asn Thr Val Phe Leu
65                  70                  75                  80

Gln Met Asn Ser Leu Arg Ala Glu Asp Thr Ala Val Tyr Tyr Cys Ala
                85                  90                  95

Arg Cys Leu Ser Arg Met Arg Gly Tyr Gly Leu Asp Val Trp Gly Gln
            100                 105                 110

Gly Thr Thr Val Thr Val Ser
        115
```

```
<210> SEQ ID NO 51
<211> LENGTH: 318
<212> TYPE: DNA
<213> ORGANISM: Homo sapiens

<400> SEQUENCE: 51
gacatccaga tgacccagtc tccatcctcc ctgtctgcat ctgtaggaga cagagtcacc      60
atcacttgcc ggacaagtca gagcattagc agctatttaa attggtatca gcagaaacca    120
gggaaagccc ctaaactcct gatctatgct gcatccagtt tgcaaagtgg ggtcccatca    180
aggttcagtg gcagtggatc tgggacagat ttcactctca ccatcagcgg tctgcaacct    240
gaagattttg caacctacta ctgtcaacag agttacagta tgcctgcctt tggccagggg    300
```
accaagctgg agatcaaa                                                318

<210> SEQ ID NO 52
<211> LENGTH: 106
<212> TYPE: PRT
<213> ORGANISM: Homo sapiens

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Gly Leu Gln Pro
65                  70                  75                  80

Glu Asp Phe Ala Thr Tyr Tyr Cys Gln Gln Ser Tyr Ser Met Pro Ala
                85                  90                  95

Phe Gly Gln Gly Thr Lys Leu Glu Ile Lys
            100                 105

<210> SEQ ID NO 53
<211> LENGTH: 291
<212> TYPE: DNA
<213> ORGANISM: Influenza A virus

<400> SEQUENCE: 53
atgagtcttc taaccgaggt cgaaacgcct atcagaaacg aatggggtg cagatgcaac     60 gattcaagtg atcctcttgt tgttgccgca agtatcattg ggatcctgca cttgatattg    120
tggattcttg atcgtctttt tttcaaatgc atttatcgtc tctttaaaca cggtctgaaa    180
agagggcctt ctacggaagg agtaccagag tctatgaggg aagaatatcg aaaggaacag    240
cagagtgctg tggatgctga cgatagtcat tttgtcaaca tagagctgga g             291

<210> SEQ ID NO 54
<211> LENGTH: 404
<212> TYPE: DNA
<213> ORGANISM: Homo sapiens

<400> SEQUENCE: 54
aagcttccac catggacatg agggtcctcg ctcagctcct ggggctcctg ctactctggc     60
tccgaggtgc cagatgtgac atccagatga cccagtctcc atcctccctg tctgcatctg    120
taggagacag agtcaccatc acttgccggg cgagtcagaa catttacaag tatttaaatt    180
ggtatcagca gagaccaggg aaagccccta agggcctgat ctctgctgca tccgggttgc    240
aaagtggggt cccatcaagg ttcagtggca gtggatctgg gacagatttc actctcacca    300
tcaccagtct gcaacctgaa gattttgcaa cttactactg tcaacagagt tacagtcccc    360
ctctcacttt cggcggaggg accagggtgg agatcaaacg tacg                     404

<210> SEQ ID NO 55
<211> LENGTH: 404
<212> TYPE: DNA
<213> ORGANISM: Artificial Sequence
<220> FEATURE:
<223> OTHER INFORMATION: anti-sense strand, orientation 3' to 5',
      sequence from Homo sapiens

```
<400> SEQUENCE: 55
ttcgaaggtg gtacctgtac tcccaggagc gagtcgagga ccccgaggac gatgagaccg    60
aggctccacg gtctacactg taggtctact gggtcagagg taggagggac agacgtagac   120
atcctctgtc tcagtggtag tgaacggccc gctcagtctt gtaaatgttc ataaatttaa   180
ccatagtcgt ctctggtccc tttcggggat tcccggacta gagacgacgt aggcccaacg   240
tttcacccca gggtagttcc aagtcaccgt cacctagacc ctgtctaaag tgagagtggt   300
agtggtcaga cgttggactt ctaaaacgtt gaatgatgac agttgtctca atgtcagggg   360
gagagtgaaa gccgcctccc tggtcccacc tctagtttgc atgc                    404
```

<210> SEQ ID NO 56
<211> LENGTH: 131
<212> TYPE: PRT
<213> ORGANISM: Homo sapiens

<400> SEQUENCE: 56

```
Met Asp Met Arg Val Leu Ala Gln Leu Leu Gly Leu Leu Leu Leu Trp
 1               5                  10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Asn Ile Tyr Lys Tyr Leu Asn Trp Tyr Gln Gln Arg Pro Gly Lys
    50                  55                  60

Ala Pro Lys Gly Leu Ile Ser Ala Ser Gly Leu Gln Ser Gly Val
65                  70                  75                  80

Pro Ser Arg Phe Ser Gly Ser Gly Ser Gly Thr Asp Phe Thr Leu Thr
                85                  90                  95

Ile Thr Ser Leu Gln Pro Glu Asp Phe Ala Thr Tyr Tyr Cys Gln Gln
            100                 105                 110

Ser Tyr Ser Pro Pro Leu Thr Phe Gly Gly Gly Thr Arg Val Glu Ile
        115                 120                 125

Lys Arg Thr
    130
```

<210> SEQ ID NO 57
<211> LENGTH: 22
<212> TYPE: PRT
<213> ORGANISM: Homo sapiens

<400> SEQUENCE: 57

```
Met Asp Met Arg Val Leu Ala Gln Leu Leu Gly Leu Leu Leu Leu Trp
 1               5                  10                  15

Leu Arg Gly Ala Arg Cys
            20
```

<210> SEQ ID NO 58
<211> LENGTH: 23
<212> TYPE: PRT
<213> ORGANISM: Homo sapiens

<400> SEQUENCE: 58

```
Asp Ile Gln Met Thr Gln Ser Pro Ser Ser Leu Ser Ala Ser Val Gly
 1               5                  10                  15

Asp Arg Val Thr Ile Thr Cys
            20
```

```
<210> SEQ ID NO 59
<211> LENGTH: 11
<212> TYPE: PRT
<213> ORGANISM: Homo sapiens

<400> SEQUENCE: 59

Arg Ala Ser Gln Asn Ile Tyr Lys Tyr Leu Asn
1               5                   10

<210> SEQ ID NO 60
<211> LENGTH: 15
<212> TYPE: PRT
<213> ORGANISM: Homo sapiens

<400> SEQUENCE: 60

Trp Tyr Gln Gln Arg Pro Gly Lys Ala Pro Lys Gly Leu Ile Ser
1               5                   10                  15

<210> SEQ ID NO 61
<211> LENGTH: 7
<212> TYPE: PRT
<213> ORGANISM: Homo sapiens

<400> SEQUENCE: 61

Ala Ala Ser Gly Leu Gln Ser
1               5

<210> SEQ ID NO 62
<211> LENGTH: 32
<212> TYPE: PRT
<213> ORGANISM: Homo sapiens

<400> SEQUENCE: 62

Gly Val Pro Ser Arg Phe Ser Gly Ser Gly Ser Gly Thr Asp Phe Thr
1               5                   10                  15

Leu Thr Ile Thr Ser Leu Gln Pro Glu Asp Phe Ala Thr Tyr Tyr Cys
            20                  25                  30

<210> SEQ ID NO 63
<211> LENGTH: 9
<212> TYPE: PRT
<213> ORGANISM: Homo sapiens

<400> SEQUENCE: 63

Gln Gln Ser Tyr Ser Pro Pro Leu Thr
1               5

<210> SEQ ID NO 64
<211> LENGTH: 10
<212> TYPE: PRT
<213> ORGANISM: Homo sapiens

<400> SEQUENCE: 64

Phe Gly Gly Gly Thr Arg Val Glu Ile Lys
1               5                   10

<210> SEQ ID NO 65
<211> LENGTH: 800
<212> TYPE: DNA
<213> ORGANISM: Homo sapiens

<400> SEQUENCE: 65
tcgaaattaa tacgactcac tatagggaga cccaagctgg ctagcgttta aacttaagct      60
tccaccatgg acatgagggt cctcgctcag ctcctggggc tcctgctact ctggctccga     120
```

```
ggtgccagat gtgacatcca gatgacccag tctccatcct ccctgtctgc atctgtagga    180
gacagagtca ccatcacttg ccgggcgagt cagaacattt acaagtattt aaattggtat    240
cagcagagac cagggaaagc ccctaagggc ctgatctctg ctgcatccgg gttgcaaagt    300
ggggtcccat caaggttcag tggcagtgga tctgggacag atttcactct caccatcacc    360
agtctgcaac ctgaagattt tgcaacttac tactgtcaac agagttacag tccccctctc    420
actttcggcg gagggaccag ggtggagatc aaacgtacgg tggctgcacc atctgtcttc    480
atcttcccgc catctgatga gcagttgaaa tctggaactg cctctgttgt gtgcctgctg    540
aataacttct atcccagaga ggccaaagta cagtggaagg tggataacgc cctccaatcg    600
ggtaactccc aggagagtgt cacagagcag gacagcaagg acagcaccta cagcctcagc    660
agcaccctga cgctgagcaa agcagactac gagaaacaca agtctacgc ctgcgaagtc     720 acccatcagg gcctgagctc gcccgtcaca aagagcttca cagggagagtgttagagg      780 gtctagaggg cccgtttaaa                                                800
```

```
<210> SEQ ID NO 66
<211> LENGTH: 800
<212> TYPE: DNA
<213> ORGANISM: Artificial Sequence
<220> FEATURE:
<223> OTHER INFORMATION: anti-sense strand, orientation 3' to 5',
      sequence from Homo sapiens

<400> SEQUENCE: 66
```

```
agctttaatt atgctgagtg atatccctct gggttcgacc gatcgcaaat ttgaattcga     60
aggtggtacc tgtactccca ggagcgagtc gaggaccccg aggacgatga gaccgaggct    120
ccacggtcta cactgtaggt ctactgggtc agaggtagga gggacagacg tagacatcct    180
ctgtctcagt ggtagtgaac ggcccgctca gtcttgtaaa tgttcataaa tttaaccata    240
gtcgtctctg gtccctttcg gggattcccg gactagagac gacgtaggcc caacgtttca    300
ccccagggta gttccaagtc accgtcacct agaccctgtc taaagtgaga gtggtagtgg    360
tcagacgttg gacttctaaa acgttgaatg atgacagttg tctcaatgtc agggggagag    420
tgaaagccgc ctccctggtc ccacctctag tttgcatgcc accgacgtgg tagacagaag    480
tagaagggcg gtagactact cgtcaacttt agaccttgac ggagacaaca cacggacgac    540
ttattgaaga tagggtctct ccggtttcat gtcaccttcc acctattgcg ggaggttagc    600
ccattgaggg tcctctcaca gtgtctcgtc ctgtcgttcc tgtcgtggat gtcggagtcg    660
tcgtgggact gcgactcgtt tcgtctgatg ctctttgtgt ttcagatgcg gacgcttcag    720
tgggtagtcc cggactcgag cgggcagtgt ttctcgaagt tgtcccctct cacaatctcc    780
cagatctccc gggcaaattt                                                800
```

```
<210> SEQ ID NO 67
<211> LENGTH: 427
<212> TYPE: DNA
<213> ORGANISM: Homo sapiens

<400> SEQUENCE: 67
```

```
aagcttccac catgaaacac ctgtggttct tccttctcct ggtggcagct cccagctggg     60
tcctgtccca ggtgcaattg caggagtcgg gcccaggact ggtgaagcct tcggagaccc    120
tgtccctcac ctgcactgtc tctggttcgt ccatcagtaa ttactactgg agctggatcc    180
ggcagtcccc agggaaggga ctggagtgga ttgggtttat ctattacggt ggaaacacca    240
agtacaatcc ctccctcaag agccgcgtca ccatatcaca agacacttcc aagagtcagg    300
```

```
tctccctgac gatgagctct gtgaccgctg cggaatcggc cgtctatttc tgtgcgagag    360
cgtcttgtag tggtggttac tgtatccttg actactgggg ccagggaacc ctggtcaccg    420
tctcgag                                                              427

<210> SEQ ID NO 68
<211> LENGTH: 427
<212> TYPE: DNA
<213> ORGANISM: Artificial Sequence
<220> FEATURE:
<223> OTHER INFORMATION: anti-sense strand, orientation 3' to 5',
      sequence from Homo sapiens

<400> SEQUENCE: 68
ttcgaaggtg gtactttgtg gacaccaaga aggaagagga ccaccgtcga gggtcgaccc     60
aggacagggt ccacgttaac gtcctcagcc cgggtcctga ccacttcgga agcctctggg    120
acagggagtg gacgtgacag agaccaagca ggtagtcatt aatgatgacc tcgacctagg    180
ccgtcagggg tcccttccct gacctcacct aacccaaata gataatgcca cctttgtggt    240
tcatgttagg gagggagttc tcggcgcagt ggtatagtgt tctgtgaagg ttctcagtcc    300
agagggactg ctactcgaga cactggcgac gccttagccg gcagataaag acacgctctc    360
gcagaacatc accaccaatg acataggaac tgatgacccc ggtcccttgg gaccagtggc    420
agagctc                                                              427

<210> SEQ ID NO 69
<211> LENGTH: 138
<212> TYPE: PRT
<213> ORGANISM: Homo sapiens

<400> SEQUENCE: 69

Met Lys His Leu Trp Phe Phe Leu Leu Leu Val Ala Ala Pro Ser Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Ser Ser Ile
        35                  40                  45

Ser Asn Tyr Tyr Trp Ser Trp Ile Arg Gln Ser Pro Gly Lys Gly Leu
    50                  55                  60

Glu Trp Ile Gly Phe Ile Tyr Tyr Gly Gly Asn Thr Lys Tyr Asn Pro
65                  70                  75                  80

Ser Leu Lys Ser Arg Val Thr Ile Ser Gln Asp Thr Ser Lys Ser Gln
                85                  90                  95

Val Ser Leu Thr Met Ser Ser Val Thr Ala Ala Glu Ser Ala Val Tyr
            100                 105                 110

Phe Cys Ala Arg Ala Ser Cys Ser Gly Gly Tyr Cys Ile Leu Asp Tyr
        115                 120                 125

Trp Gly Gln Gly Thr Leu Val Thr Val Ser
    130                 135

<210> SEQ ID NO 70
<211> LENGTH: 19
<212> TYPE: PRT
<213> ORGANISM: Homo sapiens

<400> SEQUENCE: 70

Met Lys His Leu Trp Phe Phe Leu Leu Leu Val Ala Ala Pro Ser Trp
1               5                   10                  15
```

Val Leu Ser

<210> SEQ ID NO 71
<211> LENGTH: 30
<212> TYPE: PRT
<213> ORGANISM: Homo sapiens

<400> SEQUENCE: 71

Gln Val Gln Leu Gln Glu Ser Gly Pro Gly Leu Val Lys Pro Ser Glu
1               5                   10                  15
Thr Leu Ser Leu Thr Cys Thr Val Ser Gly Ser Ile Ser
            20                  25                  30

<210> SEQ ID NO 72
<211> LENGTH: 5
<212> TYPE: PRT
<213> ORGANISM: Homo sapiens

<400> SEQUENCE: 72

Asn Tyr Tyr Trp Ser
1               5

<210> SEQ ID NO 73
<211> LENGTH: 14
<212> TYPE: PRT
<213> ORGANISM: Homo sapiens

<400> SEQUENCE: 73

Trp Ile Arg Gln Ser Pro Gly Lys Gly Leu Glu Trp Ile Gly
1               5                   10

<210> SEQ ID NO 74
<211> LENGTH: 16
<212> TYPE: PRT
<213> ORGANISM: Homo sapiens

<400> SEQUENCE: 74

Phe Ile Tyr Tyr Gly Gly Asn Thr Lys Tyr Asn Pro Ser Leu Lys Ser
1               5                   10                  15

<210> SEQ ID NO 75
<211> LENGTH: 32
<212> TYPE: PRT
<213> ORGANISM: Homo sapiens

<400> SEQUENCE: 75

Arg Val Thr Ile Ser Gln Asp Thr Ser Lys Ser Gln Val Ser Leu Thr
1               5                   10                  15
Met Ser Ser Val Thr Ala Ala Glu Ser Ala Val Tyr Phe Cys Ala Arg
            20                  25                  30

<210> SEQ ID NO 76
<211> LENGTH: 11
<212> TYPE: PRT
<213> ORGANISM: Homo sapiens

<400> SEQUENCE: 76

Ala Ser Cys Ser Gly Gly Tyr Cys Ile Leu Asp
1               5                   10

<210> SEQ ID NO 77
<211> LENGTH: 11
<212> TYPE: PRT
<213> ORGANISM: Homo sapiens -continued

<400> SEQUENCE: 77

Tyr Trp Gly Gln Gly Thr Leu Val Thr Val Ser
1               5                   10

<210> SEQ ID NO 78
<211> LENGTH: 1557
<212> TYPE: DNA
<213> ORGANISM: Homo sapiens

<400> SEQUENCE: 78

| tggcttatcg aaattaatac gactcactat agggagaccc aagctggcta gcgtttaaac | 60 |
| ttaagcttcc accatgaaac acctgtggtt cttccttctc ctggtggcag ctcccagctg | 120 |
| ggtcctgtcc caggtgcaat tgcaggagtc gggcccagga ctggtgaagc cttcggagac | 180 |
| cctgtccctc acctgcactg tctctggttc gtccatcagt aattactact ggagctggat | 240 |
| ccggcagtcc ccagggaagg gactggagtg gattgggttt atctattacg gtggaaacac | 300 |
| caagtacaat ccctccctca gagccgcgt caccatatca caagacactt ccaagagtca | 360 |
| ggtctccctg acgatgagct ctgtgaccgc tgcggaatcg ccgtctatt tctgtgcgag | 420 |
| agcgtcttgt agtggtggtt actgtatcct tgactactgg ggccagggaa ccctggtcac | 480 |
| cgtctcgaga gcctccacca agggcccatc ggtcttcccc ctggcaccct cctccaagag | 540 |
| cacctctggg ggcacagcgg ccctgggctg cctggtcaag gactacttcc ccgaaccggt | 600 |
| gacggtgtcg tggaactcag gcgccctgac cagcggcgtg cacaccttcc cggctgtcct | 660 |
| acagtcctca ggactctact ccctcagcag cgtggtgacc gtgccctcca gcagcttggg | 720 |
| cacccagacc tacatctgca acgtgaatca caagcccagc aacaccaagg tggacaagag | 780 |
| agttgagccc aaatcttgtg acaaaactca cacatgccca ccgtgcccag cacctgaact | 840 |
| cctggggga ccgtcagtct tcctcttccc cccaaaaccc aaggacaccc tcatgatctc | 900 |
| ccggacccct gaggtcacat gcgtggtggt ggacgtgagc cacgaagacc ctgaggtcaa | 960 |
| gttcaactgg tacgtggacg gcgtggaggt gcataatgcc aagacaaagc cgcgggagga | 1020 |
| gcagtacaac agcacgtacc gtgtggtcag cgtcctcacc gtcctgcacc aggactggct | 1080 |
| gaatggcaag gagtacaagt gcaaggtctc caacaaagcc ctcccagccc ccatcgagaa | 1140 |
| aaccatctcc aaagccaaag gcagccccg agaaccacag gtgtacaccc tgcccccatc | 1200 |
| ccgggaggag atgaccaaga accaggtcag cctgacctgc ctggtcaaag gcttctatcc | 1260 |
| cagcgacatc gccgtggagt gggagagcaa tgggcagccg gagaacaact acaagaccac | 1320 |
| gcctcccgtg ctggactccg acggctcctt cttcctctat agcaagctca ccgtggacaa | 1380 |
| gagcaggtgg cagcagggga acgtcttctc atgctccgtg atgcatgagg ctctgcacaa | 1440 |
| ccactacacg cagaagagcc tctccctgtc tccgggtaaa tgagttctag agggcccgtt | 1500 |
| taaacccgct gatcagcctc gactgtgcct tctagttgcc agccatctgt tgtttgc | 1557 |

<210> SEQ ID NO 79
<211> LENGTH: 1557
<212> TYPE: DNA
<213> ORGANISM: Artificial Sequence
<220> FEATURE:
<223> OTHER INFORMATION: anti-sense strand, orientation 3' to 5',
      sequence from Homo sapiens

<400> SEQUENCE: 79

| accgaatagc tttaattatg ctgagtgata tccctctggg ttcgaccgat cgcaaatttg | 60 |
| aattcgaagg tggtactttg tggacaccaa gaaggaagag gaccaccgtc gagggtcgac | 120 |

```
ccaggacagg gtccacgtta acgtcctcag cccgggtcct gaccacttcg gaagcctctg    180
ggacagggag tggacgtgac agagaccaag caggtagtca ttaatgatga cctcgaccta    240
ggccgtcagg ggtcccttcc ctgacctcac ctaacccaaa tagataatgc cacctttgtg    300
gttcatgtta gggagggagt tctcggcgca gtggtatagt gttctgtgaa ggttctcagt    360
ccagagggac tgctactcga gacactggcg acgccttagc cggcagataa agacacgctc    420
tcgcagaaca tcaccaccaa tgacatagga actgatgacc ccgtcccttt ggaccagtg    480
gcagagctct cggaggtggt tcccgggtag ccagaagggg gaccgtggga ggaggttctc    540
gtggagaccc ccgtgtcgcc gggacccgac ggaccagttc ctgatgaagg gcttggcca    600
ctgccacagc accttgagtc cgcgggactg gtcgccgcac gtgtggaagg gccgacagga    660
tgtcaggagt cctgagatga gggagtcgtc gcaccactgg cacgggaggt cgtcgaaccc    720
gtgggtctgg atgtagacgt tgcacttagt gttcgggtcg ttgtggttcc acctgttctc    780
tcaactcggg tttagaacac tgttttgagt gtgtacgggt ggcacgggtc gtggacttga    840
ggacccccct ggcagtcaga aggagaaggg gggttttggg ttcctgtggg agtactagag    900
ggcctgggga ctccagtgta cgcaccacca cctgcactcg gtgcttctgg gactccagtt    960
caagttgacc atgcacctgc cgcacctcca cgtattacgg ttctgtttcg gcgccctcct   1020
cgtcatgttg tcgtgcatgg cacaccagtc gcaggagtgg caggacgtgg tcctgaccga   1080
cttaccgttc ctcatgttca cgttccagag gttgtttcgg gagggtcggg ggtagctctt   1140
ttggtagagg tttcggtttc ccgtcggggc tcttggtgtc cacatgtggg acggggtag   1200
ggccctcctc tactggttct tggtccagtc ggactggacg gaccagtttc cgaagatagg   1260
gtcgctgtag cggcacctca ccctctcgtt acccgtcggc ctcttgttga tgttctggtg   1320
cggagggcac gacctgaggc tgccgaggaa gaaggagata tcgttcgagt ggcacctgtt   1380
ctcgtccacc gtcgtcccct tgcagaagag tacgaggcac tacgtactcc gagacgtgtt   1440
ggtgatgtgc gtcttctcgg agagggacag aggcccattt actcaagatc tcccgggcaa   1500
atttgggcga ctagtcggag ctgacacgga agatcaacgg tcggtagaca acaaacg     1557
```

<210> SEQ ID NO 80
<211> LENGTH: 11
<212> TYPE: PRT
<213> ORGANISM: Homo sapiens

<400> SEQUENCE: 80

Trp Gly Gln Gly Thr Leu Val Thr Val Ser Ser
1               5                   10

<210> SEQ ID NO 81
<211> LENGTH: 6
<212> TYPE: PRT
<213> ORGANISM: Homo sapiens

<400> SEQUENCE: 81

Cys Thr Cys Gly Ala Gly
1               5

<210> SEQ ID NO 82
<211> LENGTH: 11
<212> TYPE: PRT
<213> ORGANISM: Homo sapiens

<400> SEQUENCE: 82

Trp Gly Gln Gly Thr Leu Val Thr Val Ser Arg
1               5                   10

<210> SEQ ID NO 83
<211> LENGTH: 404
<212> TYPE: DNA
<213> ORGANISM: Homo sapiens

<400> SEQUENCE: 83
aagcttccac catggacatg agggtcctcg ctcagctcct ggggctcctg ctactctggc      60
tccgaggtgc cagatgtgac atccaggtga cccagtctcc atcctccctg tctgcatctg     120
taggagacag agtcaccatc acttgccgcg cgagtcagaa catttacaag tatttaaatt     180
ggtatcagca gagaccaggg aaagccccta agggcctgat ctctgctgca tccgggttgc     240
aaagtggggt cccatcaagg ttcagtggca gtggatctgg gacagatttc actctcacca     300
tcaccagtct gcaacctgaa gattttgcaa cttactactg tcaacagagt tacagtcccc     360
ctctcacttt cggcggaggg accagggtgg atatcaaacg tacg                      404

<210> SEQ ID NO 84
<211> LENGTH: 404
<212> TYPE: DNA
<213> ORGANISM: Artificial Sequence
<220> FEATURE:
<223> OTHER INFORMATION: anti-sense strand, orientation 3' to 5',
      sequence from Homo sapiens

<400> SEQUENCE: 84
ttcgaaggtg gtacctgtac tcccaggagc gagtcgagga ccccgaggac gatgagaccg      60
aggctccacg gtctacactg taggtccact gggtcagagg taggagggac agacgtagac     120
atcctctgtc tcagtggtag tgaacggcgc gctcagtctt gtaaatgttc ataaatttaa     180
ccatagtcgt ctctggtccc tttcggggat tcccggacta gagacgacgt aggcccaacg     240
tttcacccca gggtagttcc aagtcaccgt cacctagacc ctgtctaaag tgagagtggt     300
agtggtcaga cgttggactt ctaaaacgtt gaatgatgac agttgtctca atgtcagggg     360
gagagtgaaa gccgcctccc tggtcccacc tatagtttgc atgc                      404

<210> SEQ ID NO 85
<211> LENGTH: 427
<212> TYPE: DNA
<213> ORGANISM: Homo sapiens

<400> SEQUENCE: 85
aagcttccac catgaaacac ctgtggttct ccttctcct ggtggcagct cccagctggg       60
tcctgtccca ggtgcaattg caggagtcgg gcccaggact ggtgaagcct tcggagaccc     120
tgtccctcac ctgcactgtc tctggttcgt ccatcagtaa ttactactgg agctggatcc     180
ggcagtcccc agggaaggga ctggagtgga ttgggtttat ctattacggt ggaaacacca     240
agtacaatcc ctccctcaag agccgcgtca ccatatcaca agacacttcc aagagtcagg     300
tctccctgac gatgagctct gtgaccgctg cggaatcggc cgtctatttc tgtgcgagag     360
cgtcttgtag tggtggttac tgtatccttg actactgggg ccagggaacc ctggtcaccg     420
tctcgag                                                                427

<210> SEQ ID NO 86
<211> LENGTH: 427
<212> TYPE: DNA
<213> ORGANISM: Artificial Sequence
<220> FEATURE:
<223> OTHER INFORMATION: anti-sense strand, orientation 3' to 5',
      sequence from Homo sapiens

<400> SEQUENCE: 86

```
ttcgaaggtg gtactttgtg gacaccaaga aggaagagga ccaccgtcga gggtcgaccc    60
aggacagggt ccacgttaac gtcctcagcc cgggtcctga ccacttcgga agcctctggg   120
acagggagtg gacgtgacag agaccaagca ggtagtcatt aatgatgacc tcgacctagg   180
ccgtcagggg tcccttccct gacctcacct aacccaaata gataatgcca cctttgtggt   240
tcatgttagg gagggagttc tcggcgcagt ggtatagtgt tctgtgaagg ttctcagtcc   300
agagggactg ctactcgaga cactggcgac gccttagccg gcagataaag acacgctctc   360
gcagaacatc accaccaatg acataggaac tgatgacccc ggtcccttgg gaccagtggc   420
agagctc                                                             427
```

<210> SEQ ID NO 87
<211> LENGTH: 427
<212> TYPE: DNA
<213> ORGANISM: Homo sapiens

<400> SEQUENCE: 87

```
aagcttccac catgaaacac ctgtggttct tccttctcct ggtggcagct cccagctggg    60
tcctgtccca ggtgcaattg caggagtcgg gcccaggact ggtgaagcct tcggagaccc   120
tgtccctcac ctgcactgtc tctggttcgt ccatcagtaa ttactactgg agctggatcc   180
ggcagtcccc agggaaggga ctggagtgga ttgggtttat ctattacggt ggaaacacca   240
agtacaatcc ctccctcaag agccgcgtca ccatatcaca agacttcc aagagtcagg    300
tctccctgac gatgagctct gtgaccgctg cggaatcggc cgtctatttc tgtgcgagag   360
cgtcttgtag tggtggttac tgtatccttg actactgggg ccagggaacc ctggtcaccg   420
tctcgag                                                             427
```

<210> SEQ ID NO 88
<211> LENGTH: 401
<212> TYPE: DNA
<213> ORGANISM: Homo sapiens

<400> SEQUENCE: 88

```
aagcttccac catggacatg agggtcctcg ctcagctcct ggggctcctg ctactctggc    60
tccgaggtgc cagatgtgac atccagatga cccagtctcc atcctccctg tctgcatctg   120
taggagacag agtcaccatc acttgccgga caagtcagag cattagcagc tatttaaatt   180
ggtatcagca gaaaccaggg aaagccccta aactcctgat ctatgctgca tccagtttgc   240
aaagtggggt cccatcaagg ttcagtggca gtggatctgg gacagatttc actctcacca   300
tcagcggtct gcaacctgaa gattttgcaa cctactactg tcaacagagt tacagtatgc   360
ctgcctttgg ccaggggacc aagctggaga tcaaacgtac g                       401
```

<210> SEQ ID NO 89
<211> LENGTH: 401
<212> TYPE: DNA
<213> ORGANISM: Artificial Sequence
<220> FEATURE:
<223> OTHER INFORMATION: anti-sense strand, orientation 3' to 5',
      sequence from Homo sapiens

<400> SEQUENCE: 89

```
ttcgaaggtg gtacctgtac tcccaggagc gagtcgagga ccccgaggac gatgagaccg    60
aggctccacg gtctacactg taggtctact gggtcagagg taggagggac agacgtagac   120
```

```
atcctctgtc tcagtggtag tgaacggcct gttcagtctc gtaatcgtcg ataaatttaa      180
ccatagtcgt ctttggtccc tttcggggat tgaggacta gatacgacgt aggtcaaacg      240
tttcacccca gggtagttcc aagtcaccgt cacctagacc ctgtctaaag tgagagtggt      300
agtcgccaga cgttggactt ctaaaacgtt ggatgatgac agttgtctca atgtcatacg      360
gacggaaacc ggtcccctgg ttcgacctct agtttgcatg c                         401

<210> SEQ ID NO 90
<211> LENGTH: 401
<212> TYPE: DNA
<213> ORGANISM: Homo sapiens

<400> SEQUENCE: 90
aagcttccac catggacatg agggtcctcg ctcagctcct ggggctcctg ctactctggc       60
tccgaggtgc cagatgtgac atccagatga cccagtctcc atcctccctg tctgcatctg      120
taggagacag agtcaccatc acttgccgga caagtcagag cattagcagc tatttaaatt      180
ggtatcagca gaaaccaggg aaagccccta aactcctgat ctatgctgca tccagtttgc      240
aaagtggggt cccatcaagg ttcagtggca gtggatctgg gacagatttc actctcacca      300
tcagcggtct gcaacctgaa gattttgcaa cctactactg tcaacagagt tacagtatgc      360
ctgcctttgg ccaggggacc aagctggaga tcaaacgtac g                         401

<210> SEQ ID NO 91
<211> LENGTH: 130
<212> TYPE: PRT
<213> ORGANISM: Homo sapiens

<400> SEQUENCE: 91

Met Asp Met Arg Val Leu Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Thr Ser
        35                  40                  45

Gln Ser Ile Ser Ser Tyr Leu Asn Trp Tyr Gln Gln Lys Pro Gly Lys
    50                  55                  60

Ala Pro Lys Leu Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Gly Leu Gln Pro Glu Asp Phe Ala Thr Tyr Tyr Cys Gln Gln
            100                 105                 110

Ser Tyr Ser Met Pro Ala Phe Gly Gln Gly Thr Lys Leu Glu Ile Lys
        115                 120                 125

Arg Thr
    130

<210> SEQ ID NO 92
<211> LENGTH: 11
<212> TYPE: PRT
<213> ORGANISM: Homo sapiens

<400> SEQUENCE: 92

Arg Thr Ser Gln Ser Ile Ser Ser Tyr Leu Asn
1               5                   10

<210> SEQ ID NO 93
```

```
<211> LENGTH: 15
<212> TYPE: PRT
<213> ORGANISM: Homo sapiens

<400> SEQUENCE: 93

Trp Tyr Gln Gln Lys Pro Gly Lys Ala Pro Lys Leu Leu Ile Tyr
1               5                   10                  15

<210> SEQ ID NO 94
<211> LENGTH: 13
<212> TYPE: PRT
<213> ORGANISM: Homo sapiens

<400> SEQUENCE: 94

Ala Ala Ser Ser Leu Gln Ser Gly Val Pro Ser Arg Phe
1               5                   10

<210> SEQ ID NO 95
<211> LENGTH: 26
<212> TYPE: PRT
<213> ORGANISM: Homo sapiens

<400> SEQUENCE: 95

Ser Gly Ser Gly Ser Gly Thr Asp Phe Thr Leu Thr Ile Ser Gly Leu
1               5                   10                  15

Gln Pro Glu Asp Phe Ala Thr Tyr Tyr Cys
            20                  25

<210> SEQ ID NO 96
<211> LENGTH: 8
<212> TYPE: PRT
<213> ORGANISM: Homo sapiens

<400> SEQUENCE: 96

Gln Gln Ser Tyr Ser Met Pro Ala
1               5

<210> SEQ ID NO 97
<211> LENGTH: 427
<212> TYPE: DNA
<213> ORGANISM: Homo sapiens

<400> SEQUENCE: 97
aagcttccac catggagttg gggctgtgct gggttttcct tgttgctatt ttaaaaggtg      60
tccagtgtga ggtgcagctg gtggagtctg ggggaggctt ggtccagcct ggggggtccc     120
tgagaatctc ctgtgcagcc tctggattca ccgtcagtag caactacatg agtgggtcc     180 gccaggctcc agggaagggg ctggagtggg tctcagttat ttatagtggt ggtagcacat     240
actacgcaga ctccgtgaag ggcagattct ccttctccag agacaactcc aagaacacag     300
tgtttcttca aatgaacagc ctgagagccg aggacacggc tgtgtattac tgtgcgagat     360
gtctgagcag gatgcggggt tacggtttag acgtctgggg ccaagggacc acggtcaccg     420
tctcgag                                                                427

<210> SEQ ID NO 98
<211> LENGTH: 427
<212> TYPE: DNA
<213> ORGANISM: Artificial Sequence
<220> FEATURE:
<223> OTHER INFORMATION: anti-sense strand, orientation 3' to 5',
      sequence from Homo sapiens

<400> SEQUENCE: 98
```

```
ttcgaaggtg gtacctcaac cccgacacga cccaaaagga caacgataaa aatttttccac    60 aggtcacact ccacgtcgac cacctcagac cccctccgaa ccaggtcgga ccccccaggg   120
actcttagag gacacgtcgg agacctaagt ggcagtcatc gttgatgtac tcaacccagg   180
cggtccgagg tcccttcccc gacctcaccc agagtcaata aatatcacca ccatcgtgta   240
tgatgcgtct gaggcacttc ccgtctaaga ggaagaggtc tctgttgagg ttcttgtgtc   300
acaaagaagt ttacttgtcg gactctcggc tcctgtgccg acacataatg acacgctcta   360
cagactcgtc ctacgcccca atgccaaatc tgcagacccc ggttccctgg tgccagtggc   420
agagctc                                                              427
```

<210> SEQ ID NO 99
<211> LENGTH: 422
<212> TYPE: DNA
<213> ORGANISM: Homo sapiens

<400> SEQUENCE: 99

```
aagcttccac catggagttg gggctgtgct gggttttcct tgttgctatt ttaaaaggtg    60
tccagtgtga ggtgcagctg gtggagtctg ggggaggctt ggtccagcct ggggggtccc   120
tgagaatctc tgtgcagcct ctggattcac cgtcagtagc aactacatga gttgggtccg   180
ccaggctcca gggaagggct ggagtgggtc tcagttattt atagtggtgg tagcacatac   240
tacgcagact ccgtgaaggg agattctcct tctccagaga caactccaag aacacagtgt   300
ttcttcaaat gaacagcctg agagcgagga cacggctgtg tattactgtg cgagatgtct   360
gagcaggatg cggggttacg gtttagacgt tggggccaag ggaccacggt caccgtctcg   420
ag                                                                   422
```

<210> SEQ ID NO 100
<211> LENGTH: 138
<212> TYPE: PRT
<213> ORGANISM: Homo sapiens

<400> SEQUENCE: 100

```
Met Glu Leu Gly Leu Cys Trp Val Phe Leu Val Ala Ile Leu Lys Gly
  1               5                  10                  15

Val Gln Cys Glu Val Gln Leu Val Glu Ser Gly Gly Gly Leu Val Gln
             20                  25                  30

Pro Gly Gly Ser Leu Arg Ile Ser Cys Ala Ala Ser Gly Phe Thr Val
         35                  40                  45

Ser Ser Asn Tyr Met Ser Trp Val Arg Gln Ala Pro Gly Lys Gly Leu
     50                  55                  60

Glu Trp Val Ser Val Ile Tyr Ser Gly Gly Ser Thr Tyr Tyr Ala Asp
 65                  70                  75                  80

Ser Val Lys Gly Arg Phe Ser Phe Ser Arg Asp Asn Ser Lys Asn Thr
                 85                  90                  95

Val Phe Leu Gln Met Asn Ser Leu Arg Ala Glu Asp Thr Ala Val Tyr
            100                 105                 110

Tyr Cys Ala Arg Cys Leu Ser Arg Met Arg Gly Tyr Gly Leu Asp Val
        115                 120                 125

Trp Gly Gln Gly Thr Thr Val Thr Val Ser
    130                 135
```

<210> SEQ ID NO 101
<211> LENGTH: 19
<212> TYPE: PRT
<213> ORGANISM: Homo sapiens

```
<400> SEQUENCE: 101

Met Glu Leu Gly Leu Cys Trp Val Phe Leu Val Ala Ile Leu Lys Gly
1               5                   10                  15

Val Gln Cys

<210> SEQ ID NO 102
<211> LENGTH: 30
<212> TYPE: PRT
<213> ORGANISM: Homo sapiens

<400> SEQUENCE: 102

Glu Val Gln Leu Val Glu Ser Gly Gly Gly Leu Val Gln Pro Gly Gly
1               5                   10                  15

Ser Leu Arg Ile Ser Cys Ala Ala Ser Gly Phe Thr Val Ser
            20                  25                  30

<210> SEQ ID NO 103
<211> LENGTH: 5
<212> TYPE: PRT
<213> ORGANISM: Homo sapiens

<400> SEQUENCE: 103

Ser Asn Tyr Met Ser
1               5

<210> SEQ ID NO 104
<211> LENGTH: 14
<212> TYPE: PRT
<213> ORGANISM: Homo sapiens

<400> SEQUENCE: 104

Trp Val Arg Gln Ala Pro Gly Lys Gly Leu Glu Trp Val Ser
1               5                   10

<210> SEQ ID NO 105
<211> LENGTH: 15
<212> TYPE: PRT
<213> ORGANISM: Homo sapiens

<400> SEQUENCE: 105

Val Ile Tyr Ser Gly Gly Ser Thr Tyr Tyr Ala Asp Ser Val Lys
1               5                   10                  15

<210> SEQ ID NO 106
<211> LENGTH: 33
<212> TYPE: PRT
<213> ORGANISM: Homo sapiens

<400> SEQUENCE: 106

Gly Arg Phe Ser Phe Ser Arg Asp Asn Ser Lys Asn Thr Val Phe Leu
1               5                   10                  15

Gln Met Asn Ser Leu Arg Ala Glu Asp Thr Ala Val Tyr Tyr Cys Ala
            20                  25                  30

Arg

<210> SEQ ID NO 107
<211> LENGTH: 12
<212> TYPE: PRT
<213> ORGANISM: Homo sapiens

<400> SEQUENCE: 107

Cys Leu Ser Arg Met Arg Gly Tyr Gly Leu Asp Val
```

```
<210> SEQ ID NO 108
<211> LENGTH: 10
<212> TYPE: PRT
<213> ORGANISM: Homo sapiens

<400> SEQUENCE: 108

Trp Gly Gln Gly Thr Thr Val Thr Val Ser
1               5                   10

<210> SEQ ID NO 109
<211> LENGTH: 6
<212> TYPE: PRT
<213> ORGANISM: Homo sapiens

<400> SEQUENCE: 109

Gly Ser Ser Ile Ser Asn
1               5

<210> SEQ ID NO 110
<211> LENGTH: 9
<212> TYPE: PRT
<213> ORGANISM: Homo sapiens

<400> SEQUENCE: 110

Phe Ile Tyr Tyr Gly Gly Asn Thr Lys
1               5

<210> SEQ ID NO 111
<211> LENGTH: 6
<212> TYPE: PRT
<213> ORGANISM: Homo sapiens

<400> SEQUENCE: 111

Gly Ser Ser Ile Ser Asn
1               5

<210> SEQ ID NO 112
<211> LENGTH: 7
<212> TYPE: PRT
<213> ORGANISM: Homo sapiens

<400> SEQUENCE: 112

Gly Phe Thr Val Ser Ser Asn
1               5

<210> SEQ ID NO 113
<211> LENGTH: 9
<212> TYPE: PRT
<213> ORGANISM: Homo sapiens

<400> SEQUENCE: 113

Val Ile Tyr Ser Gly Gly Ser Thr Tyr
1               5

<210> SEQ ID NO 114
<211> LENGTH: 10
<212> TYPE: PRT
<213> ORGANISM: Homo sapiens

<400> SEQUENCE: 114

Phe Gly Gln Gly Thr Lys Leu Glu Ile Lys
1               5                   10
```

```
<210> SEQ ID NO 115
<211> LENGTH: 24
<212> TYPE: PRT
<213> ORGANISM: Influenza A virus

<400> SEQUENCE: 115

Met Ser Leu Leu Thr Glu Val Glu Thr Pro Ile Lys Asn Gly Trp Glu
1               5                   10                  15

Cys Lys Cys Asn Asp Ser Ser Asp
            20

<210> SEQ ID NO 116
<211> LENGTH: 23
<212> TYPE: PRT
<213> ORGANISM: Influenza A virus

<400> SEQUENCE: 116

Ser Leu Leu Thr Glu Val Glu Thr Pro Ile Arg Asn Glu Trp Gly Cys
1               5                   10                  15

Arg Cys Asn Asp Ser Ser Asp
            20

<210> SEQ ID NO 117
<211> LENGTH: 23
<212> TYPE: PRT
<213> ORGANISM: Influenza A virus

<400> SEQUENCE: 117

Ser Leu Leu Thr Glu Val Glu Thr Pro Ile Arg Ser Glu Trp Gly Cys
1               5                   10                  15

Arg Cys Asn Asp Ser Gly Asp
            20

<210> SEQ ID NO 118
<211> LENGTH: 23
<212> TYPE: PRT
<213> ORGANISM: Influenza A virus

<400> SEQUENCE: 118

Ser Leu Leu Thr Glu Val Glu Thr Pro Ile Arg Asn Glu Trp Glu Cys
1               5                   10                  15

Arg Cys Asn Gly Ser Ser Asp
            20

<210> SEQ ID NO 119
<211> LENGTH: 23
<212> TYPE: PRT
<213> ORGANISM: Influenza A virus

<400> SEQUENCE: 119

Ser Leu Pro Thr Glu Val Glu Thr Pro Ile Arg Asn Glu Trp Gly Cys
1               5                   10                  15

Arg Cys Asn Asp Ser Ser Asp
            20

<210> SEQ ID NO 120
<211> LENGTH: 23
<212> TYPE: PRT
<213> ORGANISM: Influenza A virus

<400> SEQUENCE: 120

Ser Leu Leu Thr Glu Val Glu Thr Pro Ile Arg Asn Glu Trp Gly Cys
1               5                   10                  15
```

Arg Cys Asn Gly Ser Ser Asp
            20

<210> SEQ ID NO 121
<211> LENGTH: 23
<212> TYPE: PRT
<213> ORGANISM: Influenza A virus

<400> SEQUENCE: 121

Ser Leu Leu Thr Glu Val Asp Thr Leu Thr Arg Asn Gly Trp Gly Cys
1               5                   10                  15

Arg Cys Ser Asp Ser Ser Asp
            20

<210> SEQ ID NO 122
<211> LENGTH: 23
<212> TYPE: PRT
<213> ORGANISM: Influenza A virus

<400> SEQUENCE: 122

Ser Leu Leu Thr Glu Val Glu Thr Pro Ile Arg Lys Glu Trp Gly Cys
1               5                   10                  15

Asn Cys Ser Asp Ser Ser Asp
            20

<210> SEQ ID NO 123
<211> LENGTH: 23
<212> TYPE: PRT
<213> ORGANISM: Influenza A virus

<400> SEQUENCE: 123

Ser Leu Leu Thr Glu Val Glu Thr Leu Ile Arg Asn Gly Trp Gly Cys
1               5                   10                  15

Arg Cys Ser Asp Ser Ser Asp
            20

<210> SEQ ID NO 124
<211> LENGTH: 23
<212> TYPE: PRT
<213> ORGANISM: Influenza A virus

<400> SEQUENCE: 124

Ser Leu Leu Thr Glu Val Glu Thr Leu Thr Lys Asn Gly Trp Gly Cys
1               5                   10                  15

Arg Cys Ser Asp Ser Ser Asp
            20

<210> SEQ ID NO 125
<211> LENGTH: 23
<212> TYPE: PRT
<213> ORGANISM: Influenza A virus

<400> SEQUENCE: 125

Ser Leu Leu Thr Glu Val Glu Thr Pro Ile Arg Ser Glu Trp Gly Cys
1               5                   10                  15

Arg Tyr Asn Asp Ser Ser Asp
            20

<210> SEQ ID NO 126
<211> LENGTH: 23
<212> TYPE: PRT
<213> ORGANISM: Influenza A virus

<400> SEQUENCE: 126

```
Ser Leu Leu Thr Glu Val Glu Thr Pro Thr Arg Asn Gly Trp Glu Cys
1               5                   10                  15

Lys Cys Ser Asp Ser Ser Asp
            20
```

<210> SEQ ID NO 127
<211> LENGTH: 23
<212> TYPE: PRT
<213> ORGANISM: Influenza A virus

<400> SEQUENCE: 127

```
Ser Leu Leu Thr Glu Val Glu Thr His Thr Arg Asn Gly Trp Glu Cys
1               5                   10                  15

Lys Cys Ser Asp Ser Ser Asp
            20
```

<210> SEQ ID NO 128
<211> LENGTH: 23
<212> TYPE: PRT
<213> ORGANISM: Influenza A virus

<400> SEQUENCE: 128

```
Ser Leu Leu Thr Glu Val Lys Thr Pro Thr Arg Asn Gly Trp Glu Cys
1               5                   10                  15

Lys Cys Ser Asp Ser Ser Asp
            20
```

<210> SEQ ID NO 129
<211> LENGTH: 23
<212> TYPE: PRT
<213> ORGANISM: Influenza A virus

<400> SEQUENCE: 129

```
Ser Leu Leu Thr Glu Val Glu Thr Leu Thr Arg Asn Gly Trp Gly Cys
1               5                   10                  15

Arg Cys Ser Asp Ser Ser Asp
            20
```

<210> SEQ ID NO 130
<211> LENGTH: 23
<212> TYPE: PRT
<213> ORGANISM: Influenza A virus

<400> SEQUENCE: 130

```
Ser Leu Leu Thr Glu Val Glu Thr Pro Thr Arg Asp Gly Trp Glu Cys
1               5                   10                  15

Lys Cys Ser Asp Ser Ser Asp
            20
```

<210> SEQ ID NO 131
<211> LENGTH: 23
<212> TYPE: PRT
<213> ORGANISM: Influenza A virus

<400> SEQUENCE: 131

```
Ser Leu Leu Thr Glu Val Glu Thr Pro Thr Arg Asn Gly Trp Gly Cys
1               5                   10                  15

Arg Cys Ser Asp Ser Ser Asp
            20
```

<210> SEQ ID NO 132
<211> LENGTH: 23

```
<212> TYPE: PRT
<213> ORGANISM: Influenza A virus

<400> SEQUENCE: 132

Ser Leu Leu Thr Glu Val Glu Thr Pro Thr Arg As

<210> SEQ ID NO 138
<211> LENGTH: 23
<212> TYPE: PRT
<213> ORGANISM: Influenza A virus

<400> SEQUENCE: 138

Ser Leu Leu Thr Glu Val Glu Thr Pro Thr Arg Asn Glu Trp Glu Cys
1 5 10 15

Arg Cys Ser Asp Ser Ser Asp
20

<210> SEQ ID NO 139
<211> LENGTH: 23
<212> TYPE: PRT
<213> ORGANISM: Influenza A virus

<400> SEQUENCE: 139

Ser Leu Leu Thr Gly Val Glu Thr His Thr Arg Asn Gly Trp Gly Cys
1 5 10 15

Lys Cys Ser Asp Ser Ser Asp
20

<210> SEQ ID NO 140
<211> LENGTH: 23
<212> TYPE: PRT
<213> ORGANISM: Influenza A virus

<400> SEQUENCE: 140

Ser Leu Leu Pro Glu Val Glu Thr His Thr Arg Asn Gly Trp Gly Cys
1 5 10 15

Arg Cys Ser Asp Ser Ser Asp
20

<210> SEQ ID NO 141
<211> LENGTH: 16
<212> TYPE: PRT
<213> ORGANISM: Influenza A virus

<400> SEQUENCE: 141

Leu Leu Thr Glu Val Glu Thr Pro Ile Arg Asn Glu Trp Gly Cys Arg
1 5 10 15

<210> SEQ ID NO 142
<211> LENGTH: 15
<212> TYPE: PRT
<213> ORGANISM: Influenza A virus

<400> SEQUENCE: 142

Leu Thr Glu Val Glu Thr Pro Ile Arg Asn Glu Trp Gly Cys Arg
1 5 10 15

<210> SEQ ID NO 143
<211> LENGTH: 12
<212> TYPE: PRT
<213> ORGANISM: Influenza A virus

<400> SEQUENCE: 143

Val Glu Thr Pro Ile Arg Asn Glu Trp Gly Cys Arg
1 5 10

<210> SEQ ID NO 144
<211> LENGTH: 17
<212> TYPE: PRT

<213> ORGANISM: Influenza A virus

<400> SEQUENCE: 144

Glu Thr Pro Ile Arg Asn Gl

```
<212> TYPE: PRT
<213> ORGANISM: Influenza A virus

<400> SEQUENCE: 151

Ser Leu Leu Thr Glu Val Glu Thr Pro Ile Arg Asn Glu Trp Gly Cys
1               5                   10                  15

<210> SEQ ID NO 152
<211> LENGTH: 15
<212> TYPE: PRT
<213> ORGANISM: Influenza A virus

<400> SEQUENCE: 152

Ser Leu Leu Thr Glu Val Glu Thr Pro Ile Arg Asn Glu Trp Gly
1               5                   10                  15

<210> SEQ ID NO 153
<211> LENGTH: 14
<212> TYPE: PRT
<213> ORGANISM: Influenza A virus

<400> SEQUENCE: 153

Ser

```
<400> SEQUENCE: 158

Ser Leu Leu Thr Glu Val Glu Thr
1               5

<210> SEQ ID NO 159
<211> LENGTH: 7
<212> TYPE: PRT
<213> ORGANISM: Influenza A virus

<400> SEQUENCE: 159

Ser Leu Leu Thr Glu Val Glu
1               5

<210> SEQ ID NO 160
<211> LENGTH: 9
<212> TYPE: PRT
<213> ORGANISM: Influenza A virus

<400> SEQUENCE: 160

Ser Leu Leu Thr Glu Val Glu Thr Pro
1               5

<210> SEQ ID NO 161
<211> LENGTH: 134
<212> TYPE: PRT
<213> ORGANISM: Homo sapiens

<400> SEQUENCE: 161

Ala Ser Thr Met Asp Met Arg Val Leu Ala Gln Leu Leu Gly Leu Leu
1               5                   10                  15

Leu Leu Trp Leu Arg Gly Ala Arg Cys Asp Ile Gln Val Thr Gln Ser
            20                  25                  30

Pro Ser Ser Leu Ser Ala Ser Val Gly Asp Arg Val Thr Ile Thr Cys
        35                  40                  45

Arg Ala Ser Gln Asn Ile Tyr Lys Tyr Leu Asn Trp Tyr Gln Gln Arg
    50                  55                  60

Pro Gly Lys Ala Pro Lys Gly Leu Ile Ser Ala Ala Ser Gly Leu Gln
65                  70                  75                  80

Ser Gly Val Pro Ser Arg Phe Ser Gly Ser Gly Ser Gly Thr Asp Phe
                85                  90                  95

Thr Leu Thr Ile Thr Ser Leu Gln Pro Glu Asp Phe Ala Thr Tyr Tyr
            100                 105                 110

Cys Gln Gln Ser Tyr Ser Pro Pro Leu Thr Phe Gly Gly Gly Thr Arg
        115                 120                 125

Val Asp Ile Lys Arg Thr
    130

<210> SEQ ID NO 162
<211> LENGTH: 134
<212> TYPE: PRT
<213> ORGANISM: Homo sapiens

<400> SEQUENCE: 162

Ala Ser Thr Met Asp Met Arg Val Leu Ala Gln Leu Leu Gly Leu Leu
1               5                   10                  15

Leu Leu Trp Leu Arg Gly Ala Arg Cys Asp Ile Gln Met Thr Gln Ser
            20                  25                  30

Pro Ser Ser Leu Ser Ala Ser Val Gly Asp Arg Val Thr Ile Thr Cys
        35                  40                  45

Arg Ala Ser Gln Asn Ile Tyr Lys Tyr Leu Asn Trp Tyr Gln Gln Arg
```

```
                50                  55                  60
Pro Gly Lys Ala Pro Lys Gly Leu Ile Ser Ala Ala Ser Gly Leu Gln
 65                  70                  75                  80

Ser Gly Val Pro Ser Arg Phe Ser Gly Ser Gly Ser Gly Thr Asp Phe
                     85                  90                  95

Thr Leu Thr Ile Thr Ser Leu Gln Pro Glu Asp Phe Ala Thr Tyr Tyr
                100                 105                 110

Cys Gln Gln Ser Tyr Ser Pro Pro Leu Thr Phe Gly Gly Gly Thr Arg
                115                 120                 125

Val Glu Ile Lys Arg Thr
                130

<210> SEQ ID NO 163
<211> LENGTH: 133
<212> TYPE: PRT
<213> ORGANISM: Homo sapiens

<400> SEQUENCE: 163

Ala Ser Thr Met Asp Met Arg Val Leu Ala Gln Leu Gly Leu Leu
 1               5                  10                  15

Leu Leu Trp Leu Arg Gly Ala Arg Cys Asp Ile Gln Met Thr Gln Ser
                 20                  25                  30

Pro Ser Ser Leu Ser Ala Ser Val Gly Asp Arg Val Thr Ile Thr Cys
                 35                  40                  45

Arg Thr Ser Gln Ser Ile Ser Ser Tyr Leu Asn Trp Tyr Gln Gln Lys
             50                  55                  60

Pro Gly Lys Ala Pro Lys Leu Leu Ile Tyr Ala Ala Ser Ser Leu Gln
 65                  70                  75                  80

Ser Gly Val Pro Ser Arg Phe Ser Gly Ser Gly Ser Gly Thr Asp Phe
                     85                  90                  95

Thr Leu Thr Ile Ser Gly Leu Gln Pro Glu Asp Phe Ala Thr Tyr Tyr
                100                 105                 110

Cys Gln Gln Ser Tyr Ser Met Pro Ala Phe Gly Gln Gly Thr Lys Leu
                115                 120                 125

Glu Ile Lys Arg Thr
            130

<210> SEQ ID NO 164
<211> LENGTH: 140
<212> TYPE: PRT
<213> ORGANISM: Homo sapiens

<400> SEQUENCE: 164

Ala Ser Thr Met Lys His Leu Trp Phe Phe Leu Leu Leu Val Ala Ala
 1               5                  10                  15

Pro Ser Trp Val Leu Ser Gln Val Gln Leu Gln Glu Ser Gly Pro Gly
                 20                  25                  30

Leu Val Lys Pro Ser Glu Thr Leu Ser Leu Thr Cys Thr Val Ser Gly
                 35                  40                  45

Ser Ser Ile Ser Asn Tyr Tyr Trp Ser Trp Ile Arg Gln Ser Pro Gly
             50                  55                  60

Lys Gly Leu Glu Trp Ile Gly Phe Ile Tyr Tyr Gly Gly Asn Thr Lys
 65                  70                  75                  80

Tyr Asn Pro Ser Leu Lys Ser Arg Val Thr Ile Ser Gln Asp Thr Ser
                 85                  90                  95

Lys Ser Gln Val Ser Leu Thr Met Ser Ser Val Thr Ala Ala Glu Ser
                100                 105                 110
```

Ala Val Tyr Phe Cys Ala Arg Ala Ser Cys Ser Gly Gly Tyr Cys Ile
            115                 120                 125

Leu Asp Tyr Trp Gly Gln Thr Leu Val Thr Val Ser
    130                 135                 140

<210> SEQ ID NO 165
<211> LENGTH: 140
<212> TYPE: PRT
<213> ORGANISM: Homo sapiens

<400> SEQUENCE: 165

Ala Ser Thr Met Glu Leu Gly Leu Cys Trp Val Phe Leu Val Ala Ile
1               5                   10                  15

Leu Lys Gly Val Gln Cys Glu Val Gln Leu Val Glu Ser Gly Gly Gly
            20                  25                  30

Leu Val Gln Pro Gly Gly Ser Leu Arg Ile Ser Cys Ala Ala Ser Gly
        35                  40                  45

Phe Thr Val Ser Ser Asn Tyr Met Ser Trp Val Arg Gln Ala Pro Gly
    50                  55                  60

Lys Gly Leu Glu Trp Val Ser Val Ile Tyr Ser Gly Gly Ser Thr Tyr
65                  70                  75                  80

Tyr Ala Asp Ser Val Lys Gly Arg Phe Ser Phe Ser Arg Asp Asn Ser
                85                  90                  95

Lys Asn Thr Val Phe Leu Gln Met Asn Ser Leu Arg Ala Glu Asp Thr
            100                 105                 110

Ala Val Tyr Tyr Cys Ala Arg Cys Leu Ser Arg Met Arg Gly Tyr Gly
        115                 120                 125

Leu Asp Val Trp Gly Gln Thr Thr Val Thr Val Ser
    130                 135                 140

<210> SEQ ID NO 166
<211> LENGTH: 140
<212> TYPE: PRT
<213> ORGANISM: Homo sapiens

<400> SEQUENCE: 166

Ala Ser Thr Met Lys His Leu Trp Phe Phe Leu Leu Leu Val Ala Ala
1               5                   10                  15

Pro Ser Trp Val Leu Ser Gln Val Gln Leu Gln Glu Ser Gly Pro Gly
            20                  25                  30

Leu Val Lys Pro Ser Glu Thr Leu Ser Leu Thr Cys Thr Val Ser Gly
        35                  40                  45

Ser Ser Ile Ser Asn Tyr Tyr Trp Ser Trp Ile Arg Gln Ser Pro Gly
    50                  55                  60

Lys Gly Leu Glu Trp Ile Gly Phe Ile Tyr Tyr Gly Gly Asn Thr Lys
65                  70                  75                  80

Tyr Asn Pro Ser Leu Lys Ser Arg Val Thr Ile Ser Gln Asp Thr Ser
                85                  90                  95

Lys Ser Gln Val Ser Leu Thr Met Ser Ser Val Thr Ala Ala Glu Ser
            100                 105                 110

Ala Val Tyr Phe Cys Ala Arg Ala Ser Cys Ser Gly Gly Tyr Cys Ile
        115                 120                 125

Leu Asp Tyr Trp Gly Gln Thr Leu Val Thr Val Ser
    130                 135                 140